US009476890B2

(12) United States Patent
Moestrup et al.

(10) Patent No.: US 9,476,890 B2
(45) Date of Patent: Oct. 25, 2016

(54) CD163-BINDING CONJUGATES

(75) Inventors: Soren Moestrup, Aarhus N (DK); Holger J. Moller, Aabyhoj (DK)

(73) Assignee: AFFINICON APS, Aarhus (DK)

(*) Notice: Subject to any disclaimer, the term of this patent is extended or adjusted under 35 U.S.C. 154(b) by 1202 days.

(21) Appl. No.: 11/943,175

(22) Filed: Nov. 20, 2007

(65) Prior Publication Data

US 2008/0242843 A1   Oct. 2, 2008

Related U.S. Application Data

(60) Continuation of application No. 10/885,784, filed on Jul. 8, 2004, now abandoned, which is a division of application No. 09/977,577, filed on Oct. 16, 2001, now abandoned.

(60) Provisional application No. 60/270,120, filed on Feb. 22, 2001.

(30) Foreign Application Priority Data

Oct. 16, 2000  (DK) .................................. 2000 01543
Jan. 11, 2001  (DK) .................................. 2001 00039

(51) Int. Cl.
| | |
|---|---|
| *C07K 16/28* | (2006.01) |
| *G01N 33/72* | (2006.01) |
| *A61K 47/48* | (2006.01) |
| *C07K 14/705* | (2006.01) |
| *C07K 14/805* | (2006.01) |
| *A61K 38/00* | (2006.01) |

(52) U.S. Cl.
CPC ....... *G01N 33/721* (2013.01); *A61K 47/48307* (2013.01); *C07K 14/70596* (2013.01); *C07K 14/805* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,061,735 A | 12/1977 | Funakoshi et al. ............. 514/21 |
| 4,103,687 A | 8/1978 | Ishii .............................. 604/500 |
| 4,769,330 A | 9/1988 | Paoletti et al. | |
| 5,155,020 A | 10/1992 | Paoletti | |
| 5,204,243 A | 4/1993 | Paoletti | |
| 5,225,336 A | 7/1993 | Paoletti | |
| 5,252,348 A | 10/1993 | Schreier et al. | |
| 5,677,427 A * | 10/1997 | Goldenberg et al. ...... 530/387.3 |
| 5,928,913 A | 7/1999 | Efstathiou et al. | |
| 5,962,667 A | 10/1999 | Jain et al. | |
| 5,972,707 A | 10/1999 | Roy et al. | |
| 5,972,899 A | 10/1999 | Zychlinsky et al. | |
| 6,025,337 A | 2/2000 | Truong et al. | |
| 6,046,314 A | 4/2000 | Gebe et al. | |
| 6,063,901 A | 5/2000 | Tryggvason et al. | |
| 6,204,054 B1 * | 3/2001 | Sutton et al. ................. 435/334 |
| 6,605,699 B1 * | 8/2003 | Ni et al. ........................ 530/350 |
| 2001/0041177 A1 * | 11/2001 | Guyre et al. ............... 424/130.1 |
| 2003/0207287 A1 * | 11/2003 | Short ................................ 435/6 |
| 2012/0258107 A1 * | 10/2012 | Graversen ........ A61K 47/48561 424/135.1 |

FOREIGN PATENT DOCUMENTS

| | | |
|---|---|---|
| CA | 9956723 | 11/1999 |
| DK | 2000 01543 | 10/2000 |
| DK | 2001 00039 | 1/2001 |
| WO | 02 32941 | 4/2012 |

OTHER PUBLICATIONS

Ritter et al., Biochemical Biophysical Research Communications 260: 466-474, 1999.*
Ritter et al., Pathobiology 67: 257-261, 1999.*
Hunt et al., Advances in Skin & Wound Care, 13, Supplement 2: 6-11, 2000.*
Natarajan et al., Am J Clin Dermatol 1: 269-275, 2000.*
Ritter et al., *Genomic Organization and Chromosomal Localization of the Human CD163 (M130) Gene: A Member of the Scavenger Receptor Cysteine-Rich Superfamily*, Biochemical and Biophysical Research Communications, vol. 260, No. 2, 1999, pp. 466-474.
El Ghmati, et al., "Identification of Haptoglobin as an Alternative Ligand for CD11b/CD18", *Journal Immunol.*, vol. 156, pp. 2542-2552, 1996.
Hogger, et al., "Identification of the Integral Membrane Protein RM3/1 on Human Monocytes as a Glucocorticoid-Inducible Member of the Scavenger Receptor Cysteine-Rich Family (CD163)", *The Journal of Immunology*, vol. 161, pp. 1883-1890, 1998.
Madsen, et al., "Haptoglobin and CD163: captor and receptor gating hemoglobin to macrophage lysosomes", *Redox Report*, vol. 6, No. 6, pp. 386-388, 2001.
Rosse, et al., "Hemolytic Anemias and Acute Blood Loss", Harrison's Principles of Internal Medicine, 14th Edition, pp. 659-672.
Sulahian, et al., "Development of an ELISA to measure soluble CD163 in biological fluids", *Journal of Immunological Methods*, vol. 252, pp. 25-31, 2001.
Buechler, et al., "Regulation of scavenger receptor CD163 expression in human monocytes and macrophages by pro- and antiinflammatory stimuli", *Journal of Leukocyte Biology*, vol. 67, pp. 97-103, Jan. 2000.
Nielsen, et al., "A Unique Loop Extension in the Serine Protease Domain of Haptoglobin is Essential for CD163 Recognition of the Haptoglobin-Hemoglobin Complex", *Journal of Biological Chemistry*, vol. 282, No. 2, pp. 1072-1079, Jan. 12, 2007.

(Continued)

*Primary Examiner* — Phillip Gambel
(74) *Attorney, Agent, or Firm* — Browdy and Neimark, P.L.L.C.

(57) ABSTRACT

The present invention relates to haptoglobin-haemoglobin (Hp-Hb) complex or a part thereof or a mimic thereof being operably linked to a substance and capable of binding a CD163 receptor. Furthermore, the invention relates to a CD163 variant, membrane bound or soluble, capable of binding at least one haptoglobin-haemoglobin (Hp-Hb) complex, and the use of the Hp-Hb complex and the CD163 receptor for therapy.

14 Claims, 16 Drawing Sheets

(56) References Cited

OTHER PUBLICATIONS

Figure 1:
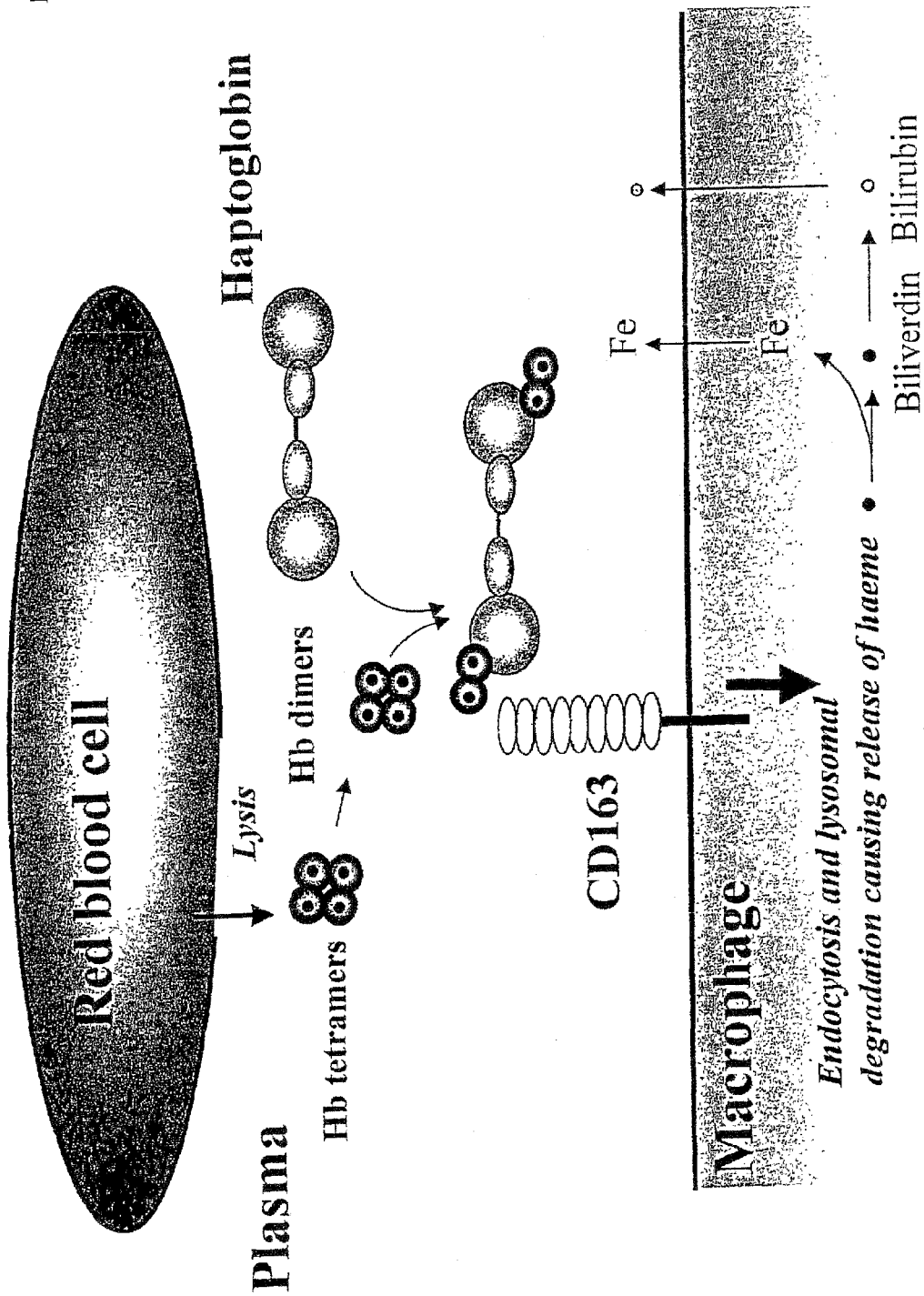

Okuda, et al, "Expression of haptoglobin receptors in human hepatoma cells", Biochimica Et Biophysica Acta, vol. 1136, pp. 143-149, 1992.

Van den Heuvel, et al., "Regulation of CD163 on human macrophages: cross-linking of CD163 induces signaling and activation", Journal of Leukocyte Biology, vol. 66, pp. 858-866, Nov. 1999.

Wagner, et al., Abstract Only, "Haptoglobin phenotyping by newly developed monoclonal antibodies. Demonstration of haptoglobin uptake into peripheral blood neutrophils and monocytes", Journal of Immunology, vol. 156(5), pp. 1989-1996, 1996.

Andris-Widhopf, J., Rader, C., Steinberger, P., Fuller, R., and Barbas, C. F., III, "Methods for the generation of chicken monoclonal antibody fragments by phage display", J Immunol Methods 242(1-2), 159-181 (Aug. 28, 2000).

Birn, H. et al., "Characterization of an epithelial ~460-kDa protein that facilitates endocytosis of intrinsic factor-vitamin $B_{12}$ and binds receptor-associated protein", J. Biol. Chem. 272, 26497-26504 (Oct. 1997).

Chander, R. et al., "Artificial viral envelopes containing recombinant human immunodeficiency virus (HIV) gp160", Life Sci. 50, 481-489 (1992).

Dubensky et al., "Direct transfection of viral and plasmid DNA into the liver or spleen of mice", Proc. Natl. Acad. Sci. USA 81, 7529-7533 (Dec. 1984).

Epstein, A. L. et al., "Biology of the human malignant lymphomas. IV. Functional characterization of ten diffuse histiocytic lymphoma cell lines", Cancer 42, 2379-2391 (Nov. 1978).

Ferry et al., "Retroviral-mediated gene transfer into hepatocytes in vivo", Proc. Natl. Acad. Sci. USA 88, 8377-8381 (Oct. 1991).

Ghmati et al., Identification of haptoglobin as an alternative ligand for CD11b/CD18, J. Immunol. 156, 2542-2552 (Apr. 1, 1996).

Hatzoglu et al., "Hepatic gene transfer in animals using retroviruses containing the promoter from the gene for phosphoenolpyruvate carboxykinase", J. Biol. Chem. 265, 17285-17293 (Oct. 5, 1990).

Hiebert et al., "E1A-dependent trans-activation of the human *MYC* promoter is mediated by the E2F factor", Proc. Natl. Acad. Sci. USA 86, 3594-3598 (May 1989).

Horn, I. R., Moestrup, S. K., van den Berg, B. M., Pannekoek, H., Nielsen, M. S., and van Zonneveld, A. J., "Analysis of the binding of pro-urokinase and urokinase-plasminogen activator inhibitor-1 complex to the low density lipoprotein receptor-related protein using a Fab fragment selected from a phage-displayed Fab Library", J. Biol. Chem. 270(20), 11770-11775 (May 1995).

Kaneda et al., "Increased expression of DNA cointroduced with nuclear protein in adult rat liver", Science 243, 375-378 (Jan. 20, 1989).

Kang, A. S., Burton, D. R., and Lerner, R. A., "Combinatorial immunoglobulin libraries in phage λ", Methods: A Companion to Methods in Enzymology 2(2), 111-118 (Apr. 1991).

Kozyraki, R., Fyfe, J., Kristiansen, M., Gerdes, C., Jacobsen, C., Cui, S., Christensen, E. I., Aminoff, M., de la Chapelle, A., Krahe, R., Verroust, P. J., and Moestrup, S. K., "The intrinsic factor-vitamin $B_{12}$ receptor, cubilin, is a high-affinity apolipoprotein A-I receptor facilitating endocytosis of high-density lipoprotein", Nat. Med. 5(6), 656-61 (Jun. 1999).

Kristiansen, M., Kozyraki, R., Jacobsen, C., Nexo, E., Verroust, P.J., and Moestrup, S.K., "Molecular dissection of the intrinsic factor-vitamin $B_{12}$ receptor, cubilin, discloses regions important for membrane association and ligand binding", J. Biol. Chem. 274, 20540-20544 (Jul. 16, 1999).

Kristiansen, M., Graversen, J.H., Jacobsen, C., Sonne, O., Hoffman, H., Alex Law, S.K., and Moestrup, S.K., "Identification of the hemoglobin scavenger receptor", Nature 409, 198-201 (Jan. 2001).

Alex Law, S. K. et al., "A new macrophage differentiation antigen which is a member of the scavenger receptor superfamily", Eur. J. Immunol. 23, 2320-2325 (Sep. 1993).

Marks, J. D., Hoogenboom, H. R., Bonnert, T. P., McCafferty, J., Griffiths, A. D., and Winter, G., "By-passing immunization. Human antibodies from V-gene libraries displayed on phage", J. Mol. Biol. 222(3), 581-597 (Sep. 1991).

Moestrup, S. K., Christensen, E. I., Sottrup-Jensen, L. & Gliemann, J., "Binding and receptor-mediated endocytosis of pregnancy zone protein-proteinase complex in rat macrophages", Biochim. Biophys. Acta 930, 297-303 (Oct. 1, 1987).

Moestrup, S. K., Kaltoft, K., Sottrup-Jensen, L. & Gliemann, J., "The human $\alpha_2$-macroglobulin receptor contains high affinity calcium binding sites important for receptor conformation and ligand recognition", J. Biol. Chem. 265, 12623-12628 (Jul. 1990).

Moestrup, S. K. & Gliemann, J., "Analysis of ligand recognition by the purified $\alpha_2$-macroglobulin receptor (low density lipoprotein receptor-related protein)", J. Biol. Chem. 266, 14011-14017 (Jul. 1991).

Moestrup, S. K. et al., "$\beta_2$-glycoprotein-I (apolipoprotein H) and $\beta_2$-glycoprotein-I-phospholipid complex harbor a recognition site for the endocytic receptor megalin", J. Clin. Invest. 102, 902-909 (Sep. 1998).

Morishita R. et al., "Novel in vitro gene transfer method for study of local modulators in vascular smooth muscle cells", Hypertension 21, 894-899 (Jun. 1993).

Nabel, E. G. et al., "Recombinant gene expression in vivo within endothelial cells of the arterial wall", Science 244, 1342-1344 (Jun. 1989).

Pulford, K., Micklem, K., Alex Law, S. K. & Mason, D. Y., "CD163 (M130 antigen) workshop panel report", in Leukocyte Typing VI. (eds. Kishimoto, T. et al.) 1089-1091 (Garland Publishing Inc., New York, 1997).

Ritter et al., "The scavenger receptor CD163: regulation, promoter structure and genomic organization", Pathobiology 67, 257-261 (1999).

Schreier, H. et al., "Targeting of liposomes to cells expressing CD4 using glycosylphosphatidylinositol-anchored gp120", J. Biol. Chem. 269, 9090-9098 (Mar. 1994).

Schreier, H., "The new frontier: gene and oligonucleotide therapy", Pharm. Acta Helv. 68, 145-159 (Jan. 1994).

Schreier H. et al., "(Patho)physiologic pathways to drug targeting: artificial viral envelopes", J. Mol. Recognit. 8, 59-62 (Jan.-Apr. 1995).

Sizemore, D. R. et al., "Attenuated *Shigella* as a DNA delivery vehicle for DNA-mediated immunization", Science 270, 299-302 (Oct. 1995).

Stecenko, A. A. et al., "Fusion of artificial viral envelopes containing respiratory syncytial virus (RSV) attachment (G) and fusion (F) glycoproteins with Hep-2-cells", Pharm. Pharmacol. Lett. 1, 127-129 (1992).

Van den Heuvel, M.M. et al., "Regulation of CD163 on human macrophages: cross-linking of CD163 induces signaling and activation", J. Leukoc. Bil. 66, 858-866 (Nov. 1999).

Wejman, J. C., Hovsepian, D., Wall, J. S., Hainfeld, J. F. & Greer, J., "Structure and assembly of haptoglobin polymers by electron microscopy", J. Mol. Biol. 174, 343-368 (Apr. 5, 1984).

Bowen, et al., Cell Surface Receptors and Their Ligands: In Vitro Analysis of CD6-CD166 Interactions, Proteins: Structure, Function and Genetics, 2000, pp. 420-428, vol. 40.

Bowen, et al., Cloning, Mapping, and Characterization of Activated Leukocyte-Cell Adhesion Molecule (ALCAM), a CD6 ligand, J. Exp. Med., Jun. 1995, pp. 2213-2220, vol. 181.

Freeman, et al., An ancient, highly conserved family of cysteine-rich protein domains revealed by cloning type I and type II murine macrophage scavenger receptors, Proc. Natl. Acad. Sci. USA, Nov. 1990, pp. 8810-8814, vol. 87.

Gebe, et al., Molecular cloning, genomic organization and cell-binding characteristics of mouse Spalpha, Immunology, 2000, pp. 78-86, vol. 99.

(56) References Cited

OTHER PUBLICATIONS

Gebe, et al., Molecular Cloning, Mapping to Human Chromosome 1 q21-q23, and Cell Binding Characteristics of Spalpha, a New Member of the Scavenger Receptor Cysteine-rich (SRCR) Family of Proteins, J. Biol. Chem., 1997, pp. 6151-6158, vol. 272.

Graversen, at al., CD163:a signal receptor scavenging haptoglobin-hemoglobin complexes from plasma, The International Journal of Biochemistry & Cell Biology, 2002, pp. 309-314, vol. 34.

Martinez, at al., The Conserved Scavenger Receptor Cysteine-Rich Superfamily in Therapy and Diagnosis, Pharmacological Reviews, 2011, pp. 967-1000, vol. 63, No. 4.

Patel, et al., Identification and Characterization of a 100-kD Ligand for CD6 on Human Thymic Epithelial Cells, J. Exp. Med., Apr. 1995, pp. 1563-1568, vol. 181.

Raman, Chander, CD5, An Important Regulator of Lymphocyte Selection and Immune Tolerance, Immunologic Research, 2002, pp. 255-263, vol. 26.

Raman, et al., Regulation of Casein Kinase 2 by Direct Interaction with Cell Surface Receptor CD5, The Journal of Biological Chemistry, Jul. 24, 1998, pp. 19183-19189, vol. 273, No. 30.

Resnick, at al., The SRCR superfamily: a family reminiscent of the Ig superfamily, TIBS, Jan. 1994, pp. 5-8, vol. 19.

* cited by examiner

Figure 4a

```
sp|P00737|HPT1_HUMAN     MSALGAVIALLLWGQLFAVDSGNDVTDIADDGCPKPPEIAHGYVEHSVRYQCKNYYKLRT  60
sp|P00738|HPT2_HUMAN     MSALGAVIALLLWGQLFAVDSGNDVTDIADDGCPKPPEIAHGYVEHSVRYQCKNYYKLRT  60
sp|P50417|HPT_ATEGE      MSALGAVIALLLWGQLFAVDSGNDVTDIADDGCPKPPEIANGYVEHLVRYQCKKYYRLRT  60
tr|Q60574|Q60574         MRALGAVVTLLLWGQLFAVELGNDAMDFEDDSCPKPPEIANGYVEHLVRYRCRQFYRLRA  60
tr|Q61646|Q61646         MRALGAVVTLLLWGQLFAVELGNDAMDFEDDSCPKPPEIANGYVEHLVRYRCRQFYRLRA  60
sp|Q62558|HPT_MUSSA      MRALGAVVTLLLWGQLFAAELGNDAMDFEDDSCPKPPEIANGYVEHLVRYRCRQFYRLRT  60
sp|P06866|HPT_RAT        MRALGAVVTLLLWGQLFAVELGNDATDIEDDSCPKPPEIANGYVEHLVRYRCRQFYKLQT  60
tr|O35086|O35086         MRALGAVVTLLLWGQLFAVDLSNDAMDTADDSCPKPPEIENGYVEHLVRYRC-QHYRLRT  59
sp|P19006|HPT_CANFA      ----------------EDTGSEATNNTEVSLPKPPVIENGYVEHMIRYQCKPFYKLHT  42
                                          :  ..: .  :  .  **** * :***** :**:*  .*:*::

sp|P00737|HPT1_HUMAN     EGDGVYTLN---------------------------------------------------  69
sp|P00738|HPT2_HUMAN     EGDGVYTLNDKKQWINKAVGDKLPECEADDGCPKPPEIAHGYVEHSVRYQCKNYYKLRTE 120
sp|P50417|HPT_ATEGE      EGDGVYTLN---------------------------------------------------  69
tr|Q60574|Q60574         EGDGVYTLN---------------------------------------------------  69
tr|Q61646|Q61646         EGDGVYTLN---------------------------------------------------  69
sp|Q62558|HPT_MUSSA      EGDGVYTLN---------------------------------------------------  69
sp|P06866|HPT_RAT        EGDGIYTLN---------------------------------------------------  69
tr|O35086|O35086         EGDGVYTLN---------------------------------------------------  68
sp|P19006|HPT_CANFA      EGDGVYTLN---------------------------------------------------  51
                         ****:****

sp|P00737|HPT1_HUMAN     --------NEKQWINKAVGDKLPECEAVCGKPKNPANPVQRILGGHLDAKGSFPWQAKMV 121
sp|P00738|HPT2_HUMAN     GDGVYTLNNNEKQWINKAVGDKLPECEAVCGKPKNPANPVQRILGGHLDAKGSFPWQAKMV 180
sp|P50417|HPT_ATEGE      --------NEKQWTNKAVGDKLPECEAVCGKPKNPANPVQRILGGHLDAKGSFPWQAKMV 121
tr|Q60574|Q60574         --------DEKQWMNTVAGEKLPECEAVCGKPKHPVDQVQRIIGGSMDAKGSFPWQAKMI 121
tr|Q61646|Q61646         --------DEKQWVNTVAGEKLPECEAVCGKPKHPVDQVQRIIGGSMDAKGSFPWQAKMI 121
sp|Q62558|HPT_MUSSA      --------DEKQWVNTAAGEKLPECEAVCGKPKHPVVQVQRIIGGSMDAKGSFPWQAKMI 121
sp|P06866|HPT_RAT        --------SEKQWVNPAAGDKLPKCEAVCGKPKHPVDQVQRIIGGSMDAKGSFPWQAKMI 121
tr|O35086|O35086         --------SEKQWVNTAAGERLPECEAVCGKPKHPVDQVQRIIGGSLDAKGSFPWQAKMV 120
sp|P19006|HPT_CANFA      --------SEKHWTNKAVGEKLPECEAVCGKPKNPVDQVQRIMGGSVDAKGSFPWQAKMV 103
                                 .**:*  *  ..*::**;**********:*.  ****:**  :*********** ;

sp|P00737|HPT1_HUMAN     SHHNLTTGATLINEQWLLTTAKNLFLNHSENATAKDIAPTLTLYVGKKQLVEIEKVVLHP 181
sp|P00738|HPT2_HUMAN     SHHNLTTGATLINEQWLLTTAKNLFLNHSENATAKDIAPTLTLYVGKKQLVEIEKVVLHP 240
sp|P50417|HPT_ATEGE      SRHNLTTGATLINEQWLLTTAKNLFLNHSENATAKDIAPTLTLYVGKNQLVEIEKVVLYP 181
tr|Q60574|Q60574         SRHGLTTGATLISDQWLLTTAKNLFLNHSETASGKDIAPTLTLYVGKNQLVEIEKVILHP 181
tr|Q61646|Q61646         SRHGLTTGATLISDQWLLTTAKNLFLNHSETASAKDITPTLTLYVGKNQLVEIEKVVLHP 181
sp|Q62558|HPT_MUSSA      SRHGLTTGATLISDQWLLTTAKNLFLNHSETASAKDIAPTLTLYVGKNQLVEIEKVVLHP 181
sp|P06866|HPT_RAT        SRHGLTTGATLISDQWLLTTAQNLFLNHSENATAKDIAPTLTLYVGKNQLVEIEKVVLHP 181
tr|O35086|O35086         SRHELITGATLISDQWLLTTAKNLFLNHSEDATSKDIAPTLKLYVGKMQPVEIEKVVIHP 180
sp|P19006|HPT_CANFA      SHHNLTSGATLINEQWLLTTAKNLFLGHKDDAKANDIAPTLKLYVGKNQLVEVEKVVLHP 163
                         *:*  * :***.:***:**.*.: *...::*.*****  *.***:;:* sp|P00737|HPT1_HUMAN     NYSQVDIGLIKLKQKVSVNERVMPICLPSKDYAEVGRVGYVSGWGRNANFKFTDHLKYVM 241
sp|P00738|HPT2_HUMAN     NYSQVDIGLIKLKQKVSVNERVMPICLPSKDYAEVGRVGYVSGWGRNANFKFTDHLKYVM 300
sp|P50417|HPT_ATEGE      NYSQVDIGLIKLKDKVPVNERVMPICLPSKDYAEVGRVGYVSGWGRNANFKFTDHLKYVM 241
tr|Q60574|Q60574         NHSVVDIGLIKLKQRVLVTERVMPICLPSKDYVAPGRVGYVSGWGRNQDFRFTDRLKYVM 241
tr|Q61646|Q61646         NHSVVDIGLIKLKQRVLVTERVMPICLPSKDYIAPGRVGYVSGWGRNANFRFTDRLKYVM 241
sp|Q62558|HPT_MUSSA      NHSVVDIGLIKLKQRVLVTERVMPICLPSKDYVAPGRVGYLSGWGRNVNFRFTERFKYVM 241
sp|P06866|HPT_RAT        ERSVVDIGLIKLKQKVLVTEKVMPICLPSKDYVAPGRMGYVSGWGRNVNFRFTERLKYVM 241
tr|O35086|O35086         NRSVVDIGVIKLRQKVPVNERVMPICLPSKDYIAPGRMGYVSGWGRNANFRFTDRLKYVM 240
sp|P19006|HPT_CANFA      DYSKVDIGLIKLKQKVPIDERVMPICLPSKDYAEVGRIGYVSGWGRNSNFNFTELLKYVM 223
                         :  **:*:::*  : *:*******   :*****  :** *:  :**** sp|P00737|HPT1_HUMAN     LPVADQDQCIRHYEGSTVPEKKTPKSPVGVQPILNEHTFCAGMSKYQEDTCYGDAGSAFA 301
sp|P00738|HPT2_HUMAN     LPVADQDQCIRHYEGSTVPEKKTPKSPVGVQPILNEHTFCAGMSKYQEDTCYGDAGSAFA 360
sp|P50417|HPT_ATEGE      LPVADQYQCVKHYEGSTVPEKKTPKSPVGQQPILNEHTFCAGMSKYQEDTCYGDAGSAFA 301
tr|Q60574|Q60574         LPVADQDKCVVHYEKSTVPEKKNFTSPVGVQPILNEHTFCAGLTKYEEDTCYGDAGSAFA 301
tr|Q61646|Q61646         LPVADQDKCVVHYENSTVPEKKNLTSPVGVQPILNEHTFCAGLTKYEEDTCYGDAGSAFA 301
sp|Q62558|HPT_MUSSA      LPVADQDKCVVHYENSTVPEKKNFTSPVGVQPILNEHTFCVGLSRYQEDTCYGDAGSAFA 301
sp|P06866|HPT_RAT        LPVADQEKCELHYEKSTVPEKKGAVTPVGVQPILNKHTFCAGLTKYEEDTCYGDAGSAFA 301
tr|O35086|O35086         LPVADQDSCMLHYEGSTVPEKEGSKSSVGVQPILNEHTFCAGMTKYQEDTCYGDAGSAFA 300
sp|P19006|HPT_CANFA      LPVADQDKCVQHYEGSTVPEKKSPKSPVGVQPILNEHTFCAGMSKFQEDTCYGDAGSAFA 283
                         ******  .* *** ******:   :.** *****:****.*::::*************
```

Figure 4b

```
sp|P00737|HPT1_HUMAN    VHDLEEDTWYATGILSFDKSCAVAEYGVYVKVTSIQDWVQKTIAEN  347
sp|P00738|HPT2_HUMAN    VHDLEEDTWYATGILSFDKSCAVAEYGVYVKVTSIQDWVQKTIAEN  406
sp|P50417|HPT_ATEGE     VHDLEEDTWYAAGILSFDKSCGVAEYGVYVKATSIQDWVQKTIAEN  347
tr|Q60574|Q60574        IHDMEEDTWYAAGILSFDKSCAVAEYGVYVRATDLKDWVQETMAKN  347
tr|Q61646|Q61646        IHDMEEDTWYAAGILSFDKSCAVAEYGVYVRATDLKDWVQETMAKN  347
sp|Q62558|HPT_MUSSA     IHDMEEDTWXAAGILSFDKSCAVAEYGVYVRATDLKDWVQETMAKK  347
sp|P06866|HPT_RAT       VHDTEEDTWYAAGILSFDKSCAVAEYGVYVKATDLKDWVQETMAKN  347
tr|O35086|O35086        IHDLEQDTWYAAGILSFDKSCSVAEYGVYVKVNSFLDWIQETMAKN  346
sp|P19006|HPT_CANFA     VHDQDEDTWYAAGILSFDKSCTVAEYGVYVKVPSVLAWVQETIAGN  329
                        :**  ::***  *:********* *******:.  ..  *:*:*:*  :
```

Figure 5a

```
CD163                     MVLLEDSGSADFRRHFVNLSPFTITVVLLLSACFVTSSLGGTDKELRLVDGENKCSGRVE 60
CD163 cyt. Var 1          MVLLEDSGSADFRRHFVNLSPFTITVVLLLSACFVTSSLGGTDKELRLVDGENKCSGRVE 60
CD163 cyt. var 2          MVLLEDSGSADFRRHFVNLSPFTITVVLLLSACFVTSSLGGTDKELRLVDGENKCSGRVE 60
CD163 ext. cell. Var.     MVLLEDSGSADFRRHFVNLSPFTITVVLLLSACFVTSSLGGTDKELRLVDGENKCSGRVE 60
                          ************************************************************ tr|Q07898|Q07898          VKVQEEWGTVCNNGWSMEAVSVICNQLGCPTAIKAPGWANSSAGSGRIWMDHVSCRGNES 120
tr|Q07901|Q07901          VKVQEEWGTVCNNGWSMEAVSVICNQLGCPTAIKAPGWANSSAGSGRIWMDHVSCRGNES 120
tr|Q07900|Q07900          VKVQEEWGTVCNNGWSMEAVSVICNQLGCPTAIKAPGWANSSAGSGRIWMDHVSCRGNES 120
tr|Q07899|Q07899          VKVQEEWGTVCNNGWSMEAVSVICNQLGCPTAIKAPGWANSSAGSGRIWMDHVSCRGNES 120
                          ************************************************************ tr|Q07898|Q07898          ALWDCKHDGWGKHSNCTHQQDAGVTCSDGSNLEMRLTRGGNMCSGRIEIKFQGRWGTVCD 180
tr|Q07901|Q07901          ALWDCKHDGWGKHSNCTHQQDAGVTCSDGSNLEMRLTRGGNMCSGRIEIKFQGRWGTVCD 180
tr|Q07900|Q07900          ALWDCKHDGWGKHSNCTHQQDAGVTCSDGSNLEMRLTRGGNMCSGRIEIKFQGRWGTVCD 180
tr|Q07899|Q07899          ALWDCKHDGWGKHSNCTHQQDAGVTCSDGSNLEMRLTRGGNMCSGRIEIKFQGRWGTVCD 180
                          ************************************************************ tr|Q07898|Q07898          DNFNIDHASVICRQLECGSAVSFSGSSNFGEGSGPIWFDDLICNGNESALWNCKHQGWGK 240
tr|Q07901|Q07901          DNFNIDHASVICRQLECGSAVSFSGSSNFGEGSGPIWFDDLICNGNESALWNCKHQGWGK 240
tr|Q07900|Q07900          DNFNIDHASVICRQLECGSAVSFSGSSNFGEGSGPIWFDDLICNGNESALWNCKHQGWGK 240
tr|Q07899|Q07899          DNFNIDHASVICRQLECGSAVSFSGSSNFGEGSGPIWFDDLICNGNESALWNCKHQGWGK 240
                          ************************************************************ tr|Q07898|Q07898          HNCDHAEDAGVICSKGADLSLRLVDGVTECSGRLEVRFQGEWGTICDDGWDSYDAAVACK 300
tr|Q07901|Q07901          HNCDHAEDAGVICSKGADLSLRLVDGVTECSGRLEVRFQGEWGTICDDGWDSYDAAVACK 300
tr|Q07900|Q07900          HNCDHAEDAGVICSKGADLSLRLVDGVTECSGRLEVRFQGEWGTICDDGWDSYDAAVACK 300
tr|Q07899|Q07899          HNCDHAEDAGVICSKGADLSLRLVDGVTECSGRLEVRFQGEWGTICDDGWDSYDAAVACK 300
                          ************************************************************ tr|Q07898|Q07898          QLGCPTAVTAIGRVNASKGFGHIWLDSVSCQGHEPAVWQCKHHEWGKHYCNHNEDAGVTC 360
tr|Q07901|Q07901          QLGCPTAVTAIGRVNASKGFGHIWLDSVSCQGHEPAVWQCKHHEWGKHYCNHNEDAGVTC 360
tr|Q07900|Q07900          QLGCPTAVTAIGRVNASKGFGHIWLDSVSCQGHEPAVWQCKHHEWGKHYCNHNEDAGVTC 360
tr|Q07899|Q07899          QLGCPTAVTAIGRVNASKGFGHIWLDSVSCQGHEPAVWQCKHHEWGKHYCNHNEDAGVTC 360
                          ************************************************************ tr|Q07898|Q07898          SDGSDLELRLRGGGSRCAGTVEVEIQRLLGKVCDRGWGLKEADVVCRQLGCGSALKTSYQ 420
tr|Q07901|Q07901          SDGSDLELRLRGGGSRCAGTVEVEIQRLLGKVCDRGWGLKEADVVCRQLGCGSALKTSYQ 420
tr|Q07900|Q07900          SDGSDLELRLRGGGSRCAGTVEVEIQRLLGKVCDRGWGLKEADVVCRQLGCGSALKTSYQ 420
tr|Q07899|Q07899          SDGSDLELRLRGGGSRCAGTVEVEIQRLLGKVCDRGWGLKEADVVCRQLGCGSALKTSYQ 420
                          ************************************************************ tr|Q07898|Q07898          VYSKIQATNTWLFLSSCNGNETSLWDCKNWQWGGLTCDHYEEAKITCSAHREPRLVGGDI 480
tr|Q07901|Q07901          VYSKIQATNTWLFLSSCNGNETSLWDCKNWQWGGLTCDHYEEAKITCSAHREPRLVGGDI 480
tr|Q07900|Q07900          VYSKIQATNTWLFLSSCNGNETSLWDCKNWQWGGLTCDHYEEAKITCSAHREPRLVGGDI 480
tr|Q07899|Q07899          VYSKIQATNTWLFLSSCNGNETSLWDCKNWQWGGLTCDHYEEAKITCSAHREPRLVGGDI 480
                          ************************************************************ tr|Q07898|Q07898          PCSGRVEVKHGDTWGSICDSDFSLEAASVLCRELQCGTVVSILGGAHFGEGNGQIWAEEF 540
tr|Q07901|Q07901          PCSGRVEVKHGDTWGSICDSDFSLEAASVLCRELQCGTVVSILGGAHFGEGNGQIWAEEF 540
tr|Q07900|Q07900          PCSGRVEVKHGDTWGSICDSDFSLEAASVLCRELQCGTVVSILGGAHFGEGNGQIWAEEF 540
tr|Q07899|Q07899          PCSGRVEVKHGDTWGSICDSDFSLEAASVLCRELQCGTVVSILGGAHFGEGNGQIWAEEF 540
                          ************************************************************ tr|Q07898|Q07898          QCEGHESHLSLCPVAPRPEGTCSHSRDVGVVCS--------------------------- 573
tr|Q07901|Q07901          QCEGHESHLSLCPVAPRPEGTCSHSRDVGVVCSSKTQKTSLIGSYTVKGTGLGSHSCLFL 600
tr|Q07900|Q07900          QCEGHESHLSLCPVAPRPEGTCSHSRDVGVVCS--------------------------- 573
tr|Q07899|Q07899          QCEGHESHLSLCPVAPRPEGTCSHSRDVGVVCS--------------------------- 573
                          ******************************** tr|Q07898|Q07898          ------RYTEIRLVNGKTPCEGRVELKTLGAWGSLCNSHWDIEDAHVLCQQLKCGVALST 627
tr|Q07901|Q07901          KPCLLPGYTEIRLVNGKTPCEGRVELKTLGAWGSLCNSHWDIEDAHVLCQQLKCGVALST 660
tr|Q07900|Q07900          ------RYTEIRLVNGKTPCEGRVELKTLGAWGSLCNSHWDIEDAHVLCQQLKCGVALST 627
tr|Q07899|Q07899          ------RYTEIRLVNGKTPCEGRVELKTLGAWGSLCNSHWDIEDAHVLCQQLKCGVALST 627
                          ************************************************************
```

Figure 5b

```
tr|Q07898|Q07898    PGGARFGKGNGQIWRHMFHCTGTEQHMGDCPVTALGASLCPSEQVASVICSGNQSQTLSS  687
tr|Q07901|Q07901    PGGARFGKGNGQIWRHMFHCTGTEQHMGDCPVTALGASLCPSEQVASVICSGNQSQTLSS  720
tr|Q07900|Q07900    PGGARFGKGNGQIWRHMFHCTGTEQHMGDCPVTALGASLCPSEQVASVICSGNQSQTLSS  687
tr|Q07899|Q07899    PGGARFGKGNGQIWRHMFHCTGTEQHMGDCPVTALGASLCPSEQVASVICSGNQSQTLSS  687
                    ************************************************************ tr|Q07898|Q07898    CNSSSLGPTRPTIPEESAVACIESGQLRLVNGGGRCAGRVEIYHEGSWGTICDDSWDLSD  747
tr|Q07901|Q07901    CNSSSLGPTRPTIPEESAVACIESGQLRLVNGGGRCAGRVEIYHEGSWGTICDDSWDLSD  780
tr|Q07900|Q07900    CNSSSLGPTRPTIPEESAVACIESGQLRLVNGGGRCAGRVEIYHEGSWGTICDDSWDLSD  747
tr|Q07899|Q07899    CNSSSLGPTRPTIPEESAVACIESGQLRLVNGGGRCAGRVEIYHEGSWGTICDDSWDLSD  747
                    ************************************************************ tr|Q07898|Q07898    AHVVCRQLGCGEAINATGSAHFGEGTGPIWLDEMKCNGKESRIWQCHSHGWGQQNCRHKE  807
tr|Q07901|Q07901    AHVVCRQLGCGEAINATGSAHFGEGTGPIWLDEMKCNGKESRIWQCHSHGWGQQNCRHKE  840
tr|Q07900|Q07900    AHVVCRQLGCGEAINATGSAHFGEGTGPIWLDEMKCNGKESRIWQCHSHGWGQQNCRHKE  807
tr|Q07899|Q07899    AHVVCRQLGCGEAINATGSAHFGEGTGPIWLDEMKCNGKESRIWQCHSHGWGQQNCRHKE  807
                    ************************************************************ tr|Q07898|Q07898    DAGVICSEFMSLRLTSEASREACAGRLEVFYNGAWGTVGKSSMSETTVGVVCRQLGCADK  867
tr|Q07901|Q07901    DAGVICSEFMSLRLTSEASREACAGRLEVFYNGAWGTVGKSSMSETTVGVVCRQLGCADK  900
tr|Q07900|Q07900    DAGVICSEFMSLRLTSEASREACAGRLEVFYNGAWGTVGKSSMSETTVGVVCRQLGCADK  867
tr|Q07899|Q07899    DAGVICSEFMSLRLTSEASREACAGRLEVFYNGAWGTVGKSSMSETTVGVVCRQLGCADK  867
                    ************************************************************ tr|Q07898|Q07898    GKINPASLDKAMSIPMWVDNVQCPKGPDTLWQCPSSPWEKRLASPSEETWITCDNKIRLQ  927
tr|Q07901|Q07901    GKINPASLDKAMSIPMWVDNVQCPKGPDTLWQCPSSPWEKRLASPSEETWITCDNKIRLQ  960
tr|Q07900|Q07900    GKINPASLDKAMSIPMWVDNVQCPKGPDTLWQCPSSPWEKRLASPSEETWITCDNKIRLQ  927
tr|Q07899|Q07899    GKINPASLDKAMSIPMWVDNVQCPKGPDTLWQCPSSPWEKRLASPSEETWITCDNKIRLQ  927
                    ************************************************************ tr|Q07898|Q07898    EGPTSCSGRVEIWHGGSWGTVCDDSWDLDDAQVVCQQLGCGPALKAFKEAEFGQGTGPIW  987
tr|Q07901|Q07901    EGPTSCSGRVEIWHGGSWGTVCDDSWDLDDAQVVCQQLGCGPALKAFKEAEFGQGTGPIW  1020
tr|Q07900|Q07900    EGPTSCSGRVEIWHGGSWGTVCDDSWDLDDAQVVCQQLGCGPALKAFKEAEFGQGTGPIW  987
tr|Q07899|Q07899    EGPTSCSGRVEIWHGGSWGTVCDDSWDLDDAQVVCQQLGCGPALKAFKEAEFGQGTGPIW  987
                    ************************************************************ tr|Q07898|Q07898    LNEVKCKGNESSLWDCPARRWGHSECGHKEDAAVNCTDISVQKTPQKATTGRSSRQSSFI  1047
tr|Q07901|Q07901    LNEVKCKGNESSLWDCPARRWGHSECGHKEDAAVNCTDISVQKTPQKATTGRSSRQSSFI  1080
tr|Q07900|Q07900    LNEVKCKGNESSLWDCPARRWGHSECGHKEDAAVNCTDISVQKTPQKATTGRSSRQSSFI  1047
tr|Q07899|Q07899    LNEVKCKGNESSLWDCPARRWGHSECGHKEDAAVNCTDISVQKTPQKATTGRSSRQSSFI  1047
                    ************************************************************ tr|Q07898|Q07898    AVGILGVVLLAIFVALFFLTKKRRQRQRLAVSSRGENLVHQIQYREMNSCLNADDLDLMN  1107
tr|Q07901|Q07901    AVGILGVVLLAIFVALFFLTKKRRQRQRLAVSSRGENLVHQIQYREMNSCLNADDLDLMN  1140
tr|Q07900|Q07900    AVGILGVVLLAIFVALFFLTKKRRQRQRLAVSSRGENLVHQIQYREMNSCLNADDLDLMN  1107
tr|Q07899|Q07899    AVGILGVVLLAIFVALFFLTKKRRQRQRLAVSSRGENLVHQIQYREMNSCLNADDLDLMN  1107
                    ************************************************************ tr|Q07898|Q07898    SSG----GHSEPH-------------------------------------  1116
tr|Q07901|Q07901    SSG----GHSEPH-------------------------------------  1149
tr|Q07900|Q07900    SSGLWVLGGSIAQGFRSVAAVEAQTFYFDKQLKKSKNVIGSLDAYNGQE   1156
tr|Q07899|Q07899    SSE-----NSHESADFSAAELISVSKFLPISGMEKEAILSHTEKENGNL   1151
                    **       *
```

Figure 6A
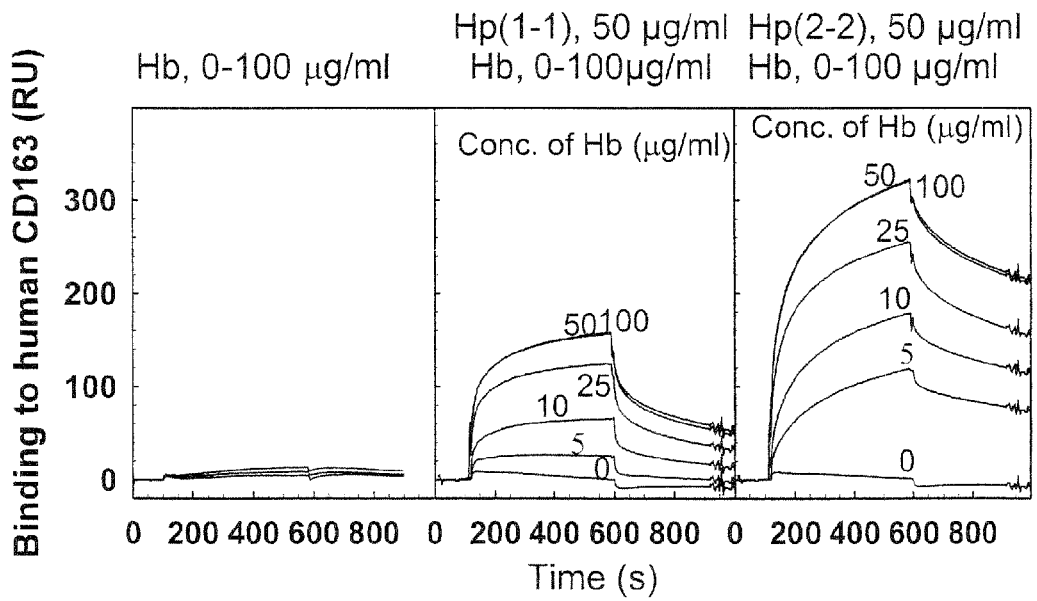
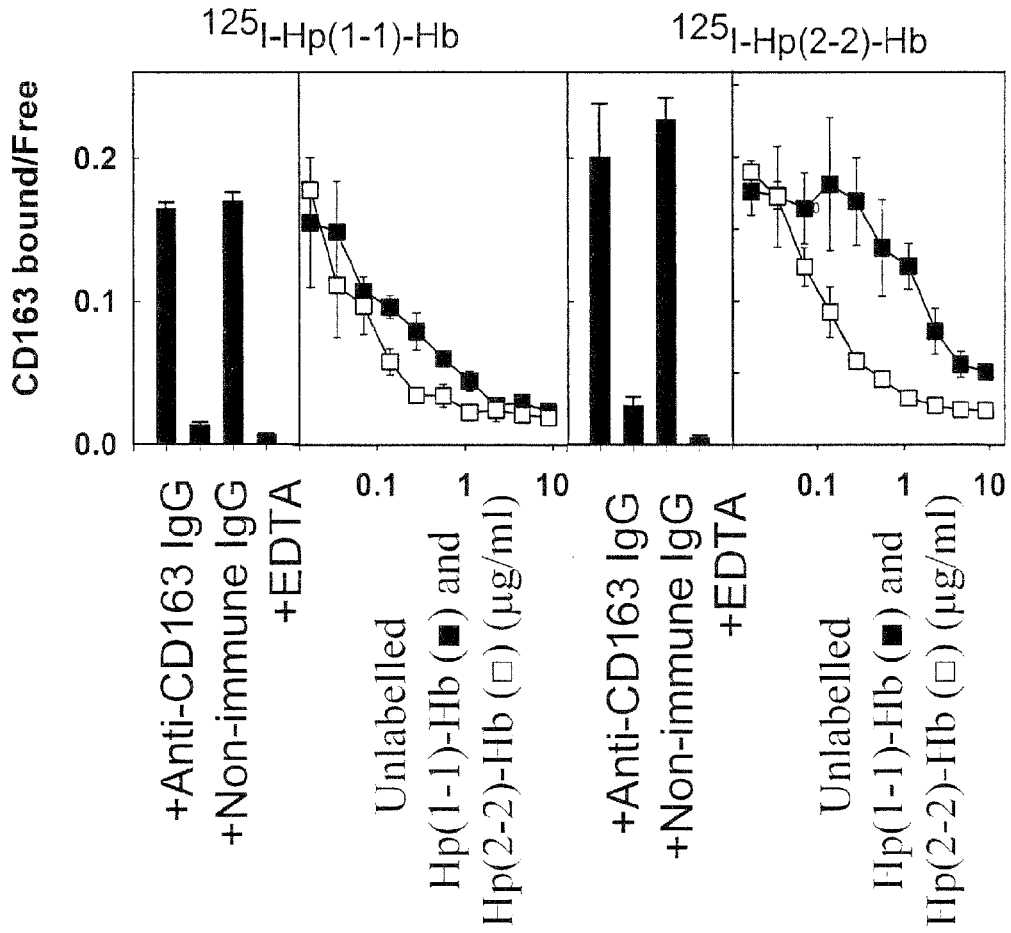
Figure 6B

Figure 7A
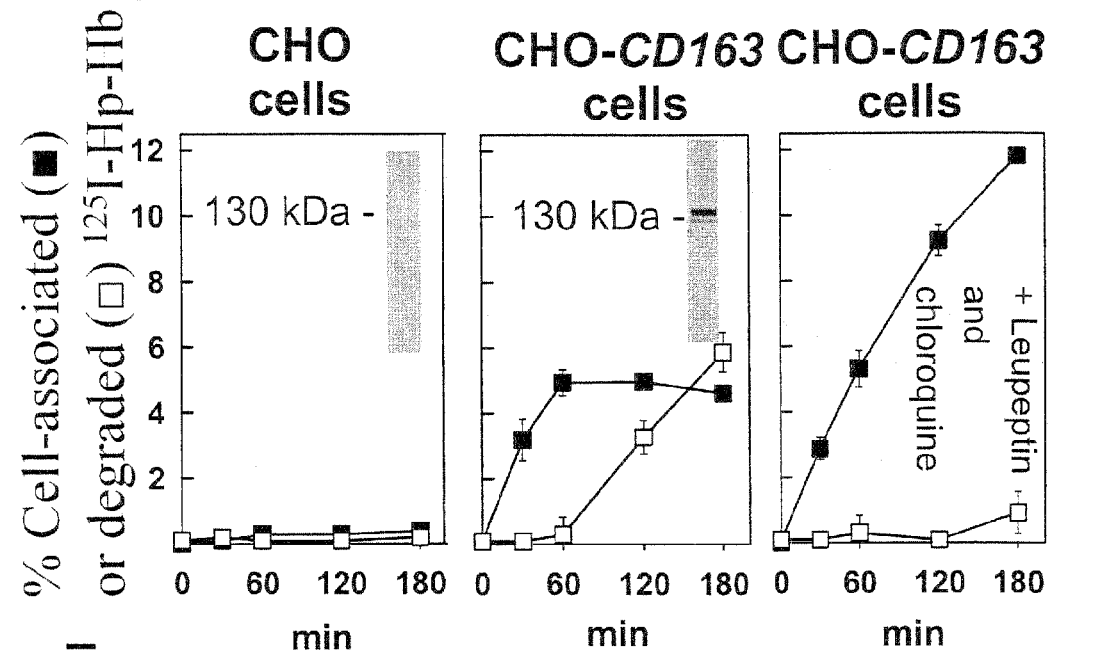
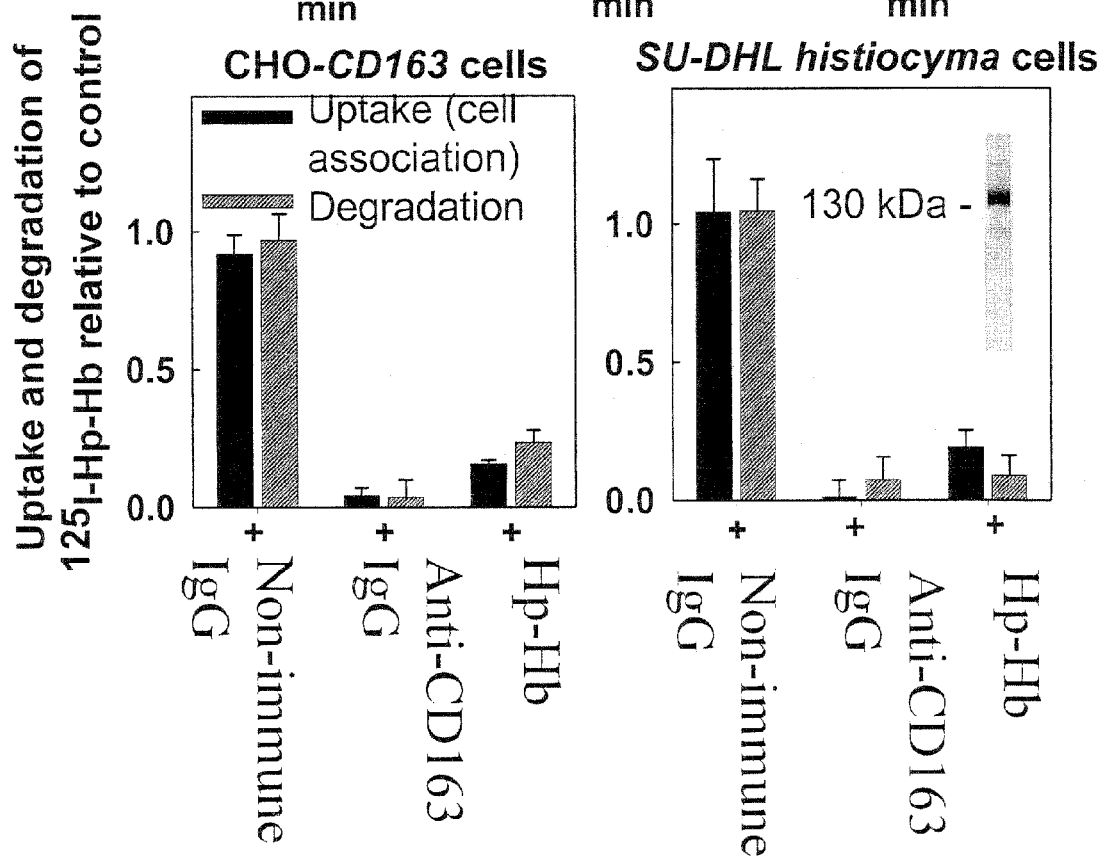
Figure 7B

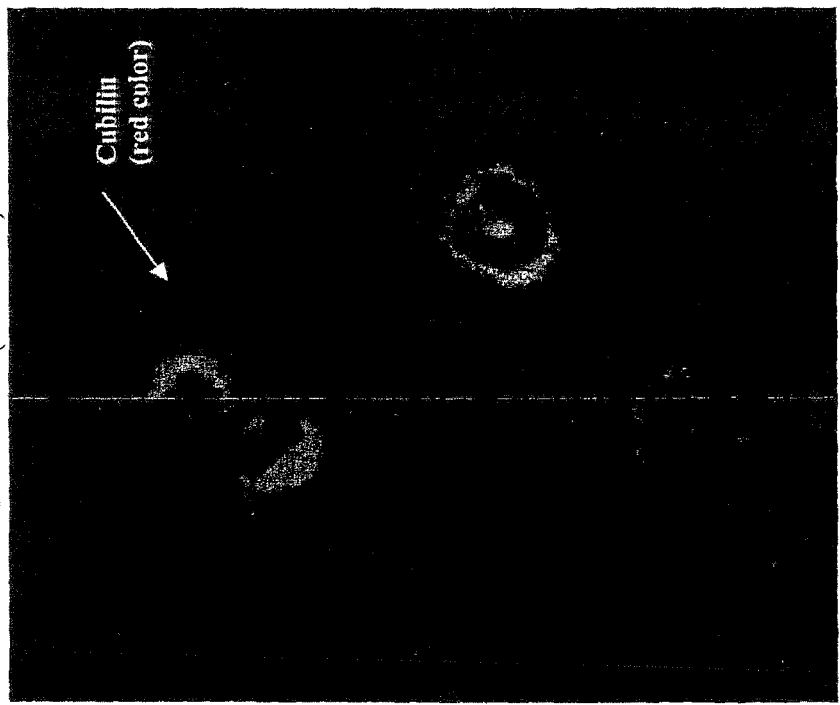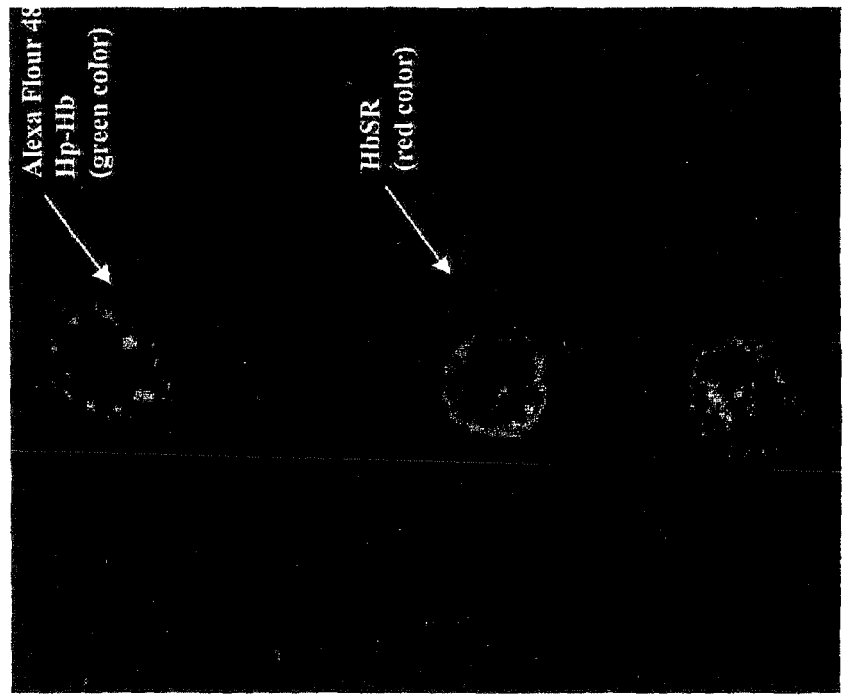

Binding of Hp(1-1)-Hb to immobilized HbSR purified from placenta or recombinant HbSR derivative corresponding to SRCR domain 1-6

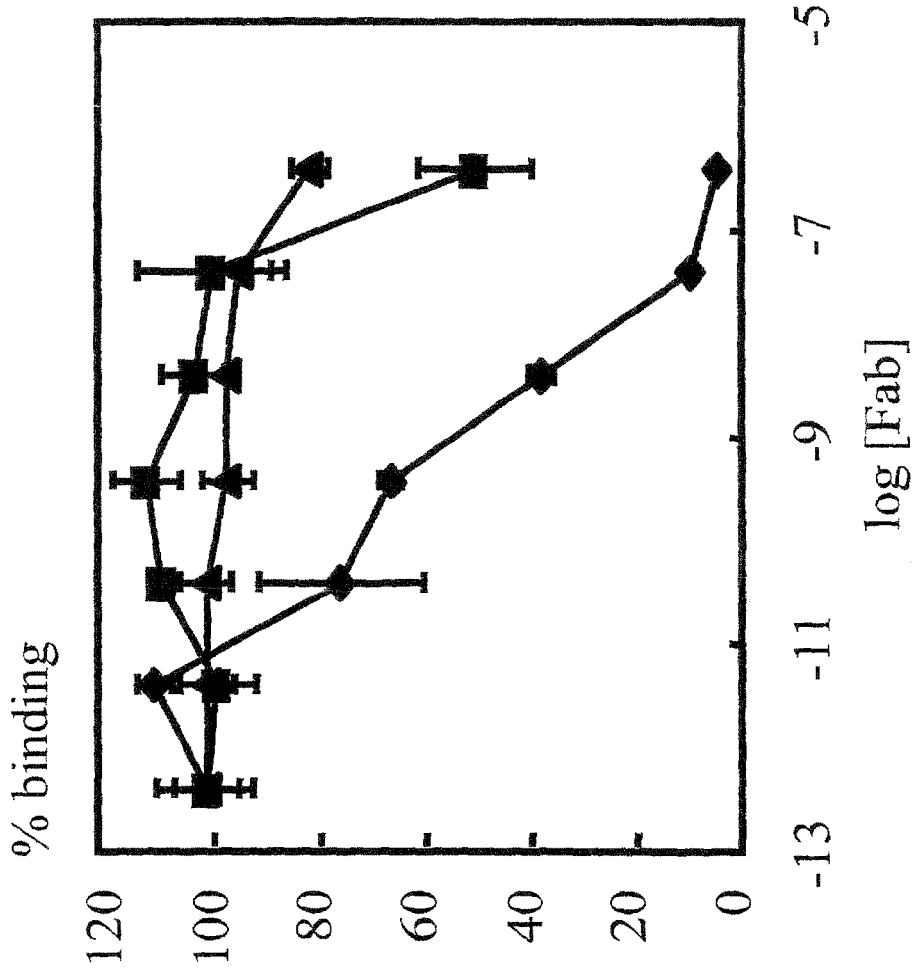

SEQUENCE LISTING

<160> NUMBER OF SEQ ID NOS: 27

<210> SEQ ID NO 1
<211> LENGTH: 347
<212> TYPE: PRT
<213> ORGANISM: Homo sapiens

<400> SEQUENCE: 1

```
Met Ser Ala Leu Gly Ala Val Ile Ala Leu Leu Leu Trp Gly Gln Leu
1               5                   10                  15

Phe Ala Val Asp Ser Gly Asn Asp Val Thr Asp Ile Ala Asp Asp Gly
            20                  25                  30

Cys Pro Lys Pro Glu Ile Ala His Gly Tyr Val Glu His Ser Val
        35                  40                  45

Arg Tyr Gln Cys Lys Asn Tyr Tyr Lys Leu Arg Thr Glu Gly Asp Gly
    50                  55                  60

Val Tyr Thr Leu Asn Asn Glu Lys Gln Trp Ile Asn Lys Ala Val Gly
65                  70                  75                  80

Asp Lys Leu Pro Glu Cys Glu Ala Val Cys Gly Lys Pro Lys Asn Pro
                85                  90                  95

Ala Asn Pro Val Gln Arg Ile Leu Gly Gly His Leu Asp Ala Lys Gly
            100                 105                 110

Ser Phe Pro Trp Gln Ala Lys Met Val Ser His His Asn Leu Thr Thr
        115                 120                 125

Gly Ala Thr Leu Ile Asn Glu Gln Trp Leu Leu Thr Thr Ala Lys Asn
130                 135                 140

Leu Phe Leu Asn His Ser Glu Asn Ala Thr Ala Lys Asp Ile Ala Pro
145                 150                 155                 160

Thr Leu Thr Leu Tyr Val Gly Lys Lys Gln Leu Val Glu Ile Glu Lys
                165                 170                 175

Val Val Leu His Pro Asn Tyr Ser Gln Val Asp Ile Gly Leu Ile Lys
            180                 185                 190

Leu Lys Gln Lys Val Ser Val Asn Glu Arg Val Met Pro Ile Cys Leu
        195                 200                 205

Pro Ser Lys Asp Tyr Ala Glu Val Gly Arg Val Gly Tyr Val Ser Gly
    210                 215                 220

Trp Gly Arg Asn Ala Asn Phe Lys Phe Thr Asp His Leu Lys Tyr Val
225                 230                 235                 240

Met Leu Pro Val Ala Asp Gln Asp Gln Cys Ile Arg His Tyr Glu Gly
                245                 250                 255

Ser Thr Val Pro Glu Lys Lys Thr Pro Lys Ser Pro Val Gly Val Gln
            260                 265                 270

Pro Ile Leu Asn Glu His Thr Phe Cys Ala Gly Met Ser Lys Tyr Gln
        275                 280                 285

Glu Asp Thr Cys Tyr Gly Asp Ala Gly Ser Ala Phe Ala Val His Asp
    290                 295                 300

Leu Glu Glu Asp Thr Trp Tyr Ala Thr Gly Ile Leu Ser Phe Asp Lys
305                 310                 315                 320

Ser Cys Ala Val Ala Glu Tyr Gly Val Tyr Val Lys Val Thr Ser Ile
                325                 330                 335

Gln Asp Trp Val Gln Lys Thr Ile Ala Glu Asn
            340                 345
```

<210> SEQ ID NO 2
<211> LENGTH: 406
<212> TYPE: PRT
<213> ORGANISM: Homo sapiens

<400> SEQUENCE: 2

```
Met Ser Ala Leu Gly Ala Val Ile Ala Leu Leu Leu Trp Gly Gln Leu
1               5                   10                  15
```

Phe Ala Val Asp Ser Gly Asn Asp Val Thr Asp Ile Ala Asp Asp Gly
                    20                  25                  30

Cys Pro Lys Pro Pro Glu Ile Ala His Gly Tyr Val Glu His Ser Val
                35                  40                  45

Arg Tyr Gln Cys Lys Asn Tyr Tyr Lys Leu Arg Thr Glu Gly Asp Gly
 50                  55                  60

Val Tyr Thr Leu Asn Asp Lys Lys Gln Trp Ile Asn Lys Ala Val Gly
 65                  70                  75                  80

Asp Lys Leu Pro Glu Cys Glu Ala Asp Gly Cys Pro Lys Pro Pro
                    85                  90                  95

Glu Ile Ala His Gly Tyr Val Glu His Ser Val Arg Tyr Gln Cys Lys
                100                 105                 110

Asn Tyr Tyr Lys Leu Arg Thr Glu Gly Asp Gly Val Tyr Thr Leu Asn
                115                 120                 125

Asn Glu Lys Gln Trp Ile Asn Lys Ala Val Gly Asp Lys Leu Pro Glu
                130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
                180                 185                 190

Asn Glu Gln Trp Leu Leu Thr Thr Ala Lys Asn Leu Phe Leu Asn His
                195                 200                 205

Ser Glu Asn Ala Thr Ala Lys Asp Ile Ala Pro Thr Leu Thr Leu Tyr
                210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
                260                 265                 270

Ala Glu Val Gly Arg Val Gly Tyr Val Ser Gly Trp Gly Arg Asn Ala
                275                 280                 285

Asn Phe Lys Phe Thr Asp His Leu Lys Tyr Val Met Leu Pro Val Ala
                290                 295                 300

Asp Gln Asp Gln Cys Ile Arg His Tyr Glu Gly Ser Thr Val Pro Glu
305                 310                 315                 320

Lys Lys Thr Pro Lys Ser Pro Val Gly Val Gln Pro Ile Leu Asn Glu
                325                 330                 335

His Thr Phe Cys Ala Gly Met Ser Lys Tyr Gln Glu Asp Thr Cys Tyr
                340                 345                 350

Gly Asp Ala Gly Ser Ala Phe Ala Val His Asp Leu Glu Glu Asp Thr
                355                 360                 365

Trp Tyr Ala Thr Gly Ile Leu Ser Phe Asp Lys Ser Cys Ala Val Ala
                370                 375                 380

Glu Tyr Gly Val Tyr Val Lys Val Thr Ser Ile Gln Asp Trp Val Gln
385                 390                 395                 400

Lys Thr Ile Ala Glu Asn
                405

<210> SEQ ID NO 3
<211> LENGTH: 347

```
<212> TYPE: PRT
<213> ORGANISM: Ateles geoffroyi

<400> SEQUENCE: 3

Met Ser Ala Leu Gly Ala Val Ile Ala Leu Leu Trp Gly Gln Leu
1               5                   10                  15

Phe Ala Val Asp Ser Gly Asn Asp Val Thr Asp Ile Ala Asp Gly
                20                  25                  30

Cys Pro Lys Pro Pro Glu Ile Ala Asn Gly Tyr Val Glu His Leu Val
            35                  40                  45

Arg Tyr Gln Cys Lys Lys Tyr Tyr Arg Leu Arg Thr Glu Gly Asp Gly
        50                  55                  60

Val Tyr Thr Leu Asn Asn Glu Lys Gln Trp Thr Asn Lys Ala Val Gly
65                  70                  75                  80

Asp Lys Leu Pro Glu Cys Glu Ala Val Cys Gly Lys Pro Lys Asn Pro
                85                  90                  95

Ala Asn Pro Val Gln Arg Ile Leu Gly Gly His Leu Asp Ala Lys Gly
            100                 105                 110

Ser Phe Pro Trp Gln Ala Lys Met Val Ser Arg His Asn Leu Thr Thr
        115                 120                 125

Gly Ala Thr Leu Ile Asn Glu Gln Trp Leu Leu Thr Thr Ala Lys Asn
    130                 135                 140

Leu Phe Leu Asn His Ser Glu Asn Ala Thr Ala Lys Asp Ile Ala Pro
145                 150                 155                 160

Thr Leu Thr Leu Tyr Val Gly Lys Asn Gln Leu Val Glu Ile Glu Lys
                165                 170                 175

Val Val Leu Tyr Pro Asn Tyr Ser Gln Val Asp Ile Gly Leu Ile Lys
            180                 185                 190

Leu Lys Asp Lys Val Pro Val Asn Glu Arg Val Met Pro Ile Cys Leu
        195                 200                 205

Pro Ser Lys Asp Tyr Ala Glu Val Gly Arg Val Gly Tyr Val Ser Gly
    210                 215                 220

Trp Gly Arg Asn Ala Asn Phe Lys Phe Thr Asp His Leu Lys Tyr Val
225                 230                 235                 240

Met Leu Pro Val Ala Asp Gln Tyr Gln Cys Val Lys His Tyr Glu Gly
                245                 250                 255

Ser Thr Val Pro Glu Lys Lys Thr Pro Lys Ser Pro Val Gly Gln Gln
            260                 265                 270

Pro Ile Leu Asn Glu His Thr Phe Cys Ala Gly Met Ser Lys Tyr Gln
        275                 280                 285

Glu Asp Thr Cys Tyr Gly Asp Ala Gly Ser Ala Phe Ala Val His Asp
    290                 295                 300

Leu Glu Glu Asp Thr Trp Tyr Ala Ala Gly Ile Leu Ser Phe Asp Lys
305                 310                 315                 320

Ser Cys Gly Val Ala Gly Tyr Gly Val Tyr Val Lys Ala Thr Ser Ile
                325                 330                 335

Gln Asp Trp Val Gln Lys Thr Ile Ala Glu Asn
            340                 345

<210> SEQ ID NO 4
<211> LENGTH: 347
<212> TYPE: PRT
<213> ORGANISM: Mus caroli

<400> SEQUENCE: 4
```

```
Met Arg Ala Leu Gly Ala Val Val Thr Leu Leu Trp Gly Gln Leu
 1               5                  10                  15

Phe Ala Val Glu Leu Gly Asn Asp Ala Met Asp Phe Glu Asp Asp Ser
             20                  25                  30

Cys Pro Lys Pro Pro Glu Ile Ala Asn Gly Tyr Val Glu His Leu Val
             35                  40                  45

Arg Tyr Arg Cys Arg Gln Phe Tyr Arg Leu Arg Ala Glu Gly Asp Gly
 50                  55                  60

Val Tyr Thr Leu Asn Asp Glu Lys Gln Trp Met Asn Thr Val Ala Gly
 65                  70                  75                  80

Glu Lys Leu Pro Glu Cys Glu Ala Val Cys Gly Lys Pro Lys His Pro
             85                  90                  95

Val Asp Gln Val Gln Arg Ile Ile Gly Gly Ser Met Asp Ala Lys Gly
             100                 105                 110

Ser Phe Pro Trp Gln Ala Lys Met Ile Ser Arg His Gly Leu Thr Thr
             115                 120                 125

Gly Ala Thr Leu Ile Ser Asp Gln Trp Leu Leu Thr Thr Ala Lys Asn
 130                 135                 140

Leu Phe Leu Asn His Ser Glu Thr Ala Ser Gly Lys Asp Ile Ala Pro
145                 150                 155                 160

Thr Leu Thr Leu Tyr Val Gly Lys Asn Gln Leu Val Glu Ile Glu Lys
             165                 170                 175

Val Ile Leu His Pro Asn His Ser Val Val Asp Ile Gly Leu Ile Lys
             180                 185                 190

Leu Lys Gln Arg Val Leu Val Thr Glu Arg Val Met Pro Ile Cys Leu
             195                 200                 205

Pro Ser Lys Asp Tyr Val Ala Pro Gly Arg Val Gly Tyr Val Ser Gly
 210                 215                 220

Trp Gly Arg Asn Gln Asp Phe Arg Phe Thr Asp Arg Leu Lys Tyr Val
225                 230                 235                 240

Met Leu Pro Val Ala Asp Gln Asp Lys Cys Val Val His Tyr Glu Lys
             245                 250                 255

Ser Thr Val Pro Glu Lys Lys Asn Phe Thr Ser Pro Val Gly Val Gln
             260                 265                 270

Pro Ile Leu Asn Glu His Thr Phe Cys Ala Gly Leu Thr Lys Tyr Glu
             275                 280                 285

Glu Asp Thr Cys Tyr Gly Asp Ala Gly Ser Ala Phe Ala Ile His Asp
             290                 295                 300

Met Glu Glu Asp Thr Trp Tyr Ala Ala Gly Ile Leu Ser Phe Asp Lys
305                 310                 315                 320

Ser Cys Ala Val Ala Glu Tyr Gly Val Tyr Val Arg Ala Thr Asp Leu
             325                 330                 335

Lys Asp Trp Val Gln Glu Thr Met Ala Lys Asn
             340                 345

<210> SEQ ID NO 5
<211> LENGTH: 347
<212> TYPE: PRT
<213> ORGANISM: Mus musculus

<400> SEQUENCE: 5

Met Arg Ala Leu Gly Ala Val Val Thr Leu Leu Trp Gly Gln Leu
 1               5                  10                  15

Phe Ala Val Glu Leu Gly Asn Asp Ala Met Asp Phe Glu Asp Asp Ser
             20                  25                  30
```

```
Cys Pro Lys Pro Pro Glu Ile Ala Asn Gly Tyr Val Glu His Leu Val
        35                  40                  45

Arg Tyr Arg Cys Arg Gln Phe Tyr Arg Leu Arg Ala Glu Gly Asp Gly
    50                  55                  60

Val Tyr Thr Leu Asn Asp Glu Lys Gln Trp Val Asn Thr Val Ala Gly
65                  70                  75                  80

Glu Lys Leu Pro Glu Cys Glu Ala Val Cys Gly Lys Pro Lys His Pro
                85                  90                  95

Val Asp Gln Val Gln Arg Ile Ile Gly Gly Ser Met Asp Ala Lys Gly
            100                 105                 110

Ser Phe Pro Trp Gln Ala Lys Met Ile Ser Arg His Gly Leu Thr Thr
        115                 120                 125

Gly Ala Thr Leu Ile Ser Asp Gln Trp Leu Leu Thr Thr Ala Lys Asn
    130                 135                 140

Leu Phe Leu Asn His Ser Glu Thr Ala Ser Ala Lys Asp Ile Thr Pro
145                 150                 155                 160

Thr Leu Thr Leu Tyr Val Gly Lys Asn Gln Leu Val Glu Ile Glu Lys
                165                 170                 175

Val Val Leu His Pro Asn His Ser Val Val Asp Ile Gly Leu Ile Lys
            180                 185                 190

Leu Lys Gln Arg Val Leu Val Thr Glu Arg Val Met Pro Ile Cys Leu
        195                 200                 205

Pro Ser Lys Asp Tyr Ile Ala Pro Gly Arg Val Gly Tyr Val Ser Gly
    210                 215                 220

Trp Gly Arg Asn Ala Asn Phe Arg Phe Thr Asp Arg Leu Lys Tyr Val
225                 230                 235                 240

Met Leu Pro Val Ala Asp Gln Asp Lys Cys Val Val His Tyr Glu Asn
                245                 250                 255

Ser Thr Val Pro Glu Lys Lys Asn Leu Thr Ser Pro Val Gly Val Gln
            260                 265                 270

Pro Ile Leu Asn Glu His Thr Phe Cys Ala Gly Leu Thr Lys Tyr Gln
        275                 280                 285

Glu Asp Thr Cys Tyr Gly Asp Ala Gly Ser Ala Phe Ala Ile His Asp
    290                 295                 300

Met Glu Glu Asp Thr Trp Tyr Ala Ala Gly Ile Leu Ser Phe Asp Lys
305                 310                 315                 320

Ser Cys Ala Val Ala Glu Tyr Gly Val Tyr Val Arg Ala Thr Asp Leu
                325                 330                 335

Lys Asp Trp Val Gln Glu Thr Met Ala Lys Asn
            340                 345

<210> SEQ ID NO 6
<211> LENGTH: 347
<212> TYPE: PRT
<213> ORGANISM: Mus saxicola
<220> FEATURE:
<221> NAME/KEY: misc_feature
<222> LOCATION: (311)..(311)
<223> OTHER INFORMATION: Xaa is unknown

<400> SEQUENCE: 6

Met Arg Ala Leu Gly Ala Val Val Thr Leu Leu Leu Trp Gly Gln Leu
1               5                   10                  15

Phe Ala Ala Glu Leu Gly Asn Asp Ala Met Asp Phe Glu Asp Asp Ser
            20                  25                  30
```

```
Cys Pro Lys Pro Pro Glu Ile Ala Asn Gly Tyr Val Glu His Leu Val
            35                  40                  45

Arg Tyr Arg Cys Arg Gln Phe Tyr Arg Leu Arg Thr Glu Gly Asp Gly
 50                  55                  60

Val Tyr Thr Leu Asn Asp Glu Lys Gln Trp Val Asn Thr Ala Ala Gly
 65                  70                  75                  80

Glu Lys Leu Pro Glu Cys Glu Ala Val Cys Gly Lys Pro Lys His Pro
                 85                  90                  95

Val Val Gln Val Gln Arg Ile Ile Gly Gly Ser Met Asp Ala Lys Gly
                100                 105                 110

Ser Phe Pro Trp Gln Ala Lys Met Ile Ser Arg His Gly Leu Thr Thr
            115                 120                 125

Gly Ala Thr Leu Ile Ser Asp Gln Trp Leu Leu Thr Thr Ala Lys Asn
130                 135                 140

Leu Phe Leu Asn His Ser Glu Thr Ala Ser Ala Lys Asp Ile Ala Pro
145                 150                 155                 160

Thr Leu Thr Leu Tyr Val Gly Lys Asn Gln Leu Val Glu Ile Glu Lys
                165                 170                 175

Val Val Leu His Pro Asn His Ser Val Val Asp Ile Gly Leu Ile Lys
            180                 185                 190

Leu Lys Gln Arg Val Leu Val Thr Glu Arg Val Met Pro Ile Cys Leu
        195                 200                 205

Pro Ser Lys Asp Tyr Val Ala Pro Gly Arg Val Gly Tyr Leu Ser Gly
    210                 215                 220

Trp Gly Arg Asn Val Asn Phe Arg Phe Thr Glu Arg Phe Lys Tyr Val
225                 230                 235                 240

Met Leu Pro Val Ala Asp Gln Asp Lys Cys Val Val His Tyr Glu Asn
                245                 250                 255

Ser Thr Val Pro Glu Lys Lys Asn Phe Thr Ser Pro Val Gly Val Gln
            260                 265                 270

Pro Ile Leu Asn Glu His Thr Phe Cys Val Gly Leu Ser Arg Tyr Gln
        275                 280                 285

Glu Asp Thr Cys Tyr Gly Asp Ala Gly Ser Ala Phe Ala Ile His Asp
    290                 295                 300

Met Glu Glu Asp Thr Trp Xaa Ala Ala Gly Ile Leu Ser Phe Asp Lys
305                 310                 315                 320

Ser Cys Ala Val Ala Glu Tyr Gly Val Tyr Val Arg Ala Thr Asp Leu
                325                 330                 335

Lys Asp Trp Val Gln Glu Thr Met Ala Lys Lys
            340                 345

<210> SEQ ID NO 7
<211> LENGTH: 347
<212> TYPE: PRT
<213> ORGANISM: Rattus norvegicus

<400> SEQUENCE: 7

Met Arg Ala Leu Gly Ala Val Val Thr Leu Leu Leu Trp Gly Gln Leu
1               5                   10                  15

Phe Ala Val Glu Leu Gly Asn Asp Ala Thr Asp Ile Glu Asp Asp Ser
            20                  25                  30

Cys Pro Lys Pro Pro Glu Ile Ala Asn Gly Tyr Val Glu His Leu Val
            35                  40                  45

Arg Tyr Arg Cys Arg Gln Phe Tyr Lys Leu Gln Thr Glu Gly Asp Gly
 50                  55                  60
```

Ile Tyr Thr Leu Asn Ser Glu Lys Gln Trp Val Asn Pro Ala Ala Gly
65                  70                  75                  80

Asp Lys Leu Pro Lys Cys Glu Ala Val Cys Gly Lys Pro Lys His Pro
                85                  90                  95

Val Asp Gln Val Gln Arg Ile Ile Gly Gly Ser Met Asp Ala Lys Gly
            100                 105                 110

Ser Phe Pro Trp Gln Ala Lys Met Ile Ser Arg His Gly Leu Thr Thr
        115                 120                 125

Gly Ala Thr Leu Ile Ser Asp Gln Trp Leu Leu Thr Thr Ala Gln Asn
130                 135                 140

Leu Phe Leu Asn His Ser Glu Asn Ala Thr Ala Lys Asp Ile Ala Pro
145                 150                 155                 160

Thr Leu Thr Leu Tyr Val Gly Lys Asn Gln Leu Val Glu Ile Glu Lys
                165                 170                 175

Val Val Leu His Pro Glu Arg Ser Val Val Asp Ile Gly Leu Ile Lys
            180                 185                 190

Leu Lys Gln Lys Val Leu Val Thr Glu Lys Val Met Pro Ile Cys Leu
        195                 200                 205

Pro Ser Lys Asp Tyr Val Ala Pro Gly Arg Met Gly Tyr Val Ser Gly
210                 215                 220

Trp Gly Arg Asn Val Asn Phe Arg Phe Thr Glu Arg Leu Lys Tyr Val
225                 230                 235                 240

Met Leu Pro Val Ala Asp Gln Glu Lys Cys Glu Leu His Tyr Glu Lys
                245                 250                 255

Ser Thr Val Pro Glu Lys Lys Gly Ala Val Thr Pro Val Gly Val Gln
            260                 265                 270

Pro Ile Leu Asn Lys His Thr Phe Cys Ala Gly Leu Thr Lys Tyr Glu
        275                 280                 285

Glu Asp Thr Cys Tyr Gly Asp Ala Gly Ser Ala Phe Ala Val His Asp
290                 295                 300

Thr Glu Glu Asp Thr Trp Tyr Ala Ala Gly Ile Leu Ser Phe Asp Lys
305                 310                 315                 320

Ser Cys Ala Val Ala Glu Tyr Gly Val Tyr Val Lys Ala Thr Asp Leu
                325                 330                 335

Lys Asp Trp Val Gln Glu Thr Met Ala Lys Asn
            340                 345

<210> SEQ ID NO 8
<211> LENGTH: 346
<212> TYPE: PRT
<213> ORGANISM: Mesocricetus auratus

<400> SEQUENCE: 8

Met Arg Ala Leu Gly Ala Val Val Thr Leu Leu Leu Trp Gly Gln Leu
1               5                   10                  15

Phe Ala Val Asp Leu Ser Asn Asp Ala Met Asp Thr Ala Asp Asp Ser
            20                  25                  30

Cys Pro Lys Pro Pro Glu Ile Glu Asn Gly Tyr Val Glu His Leu Val
        35                  40                  45

Arg Tyr Arg Cys Gln His Tyr Arg Leu Arg Thr Glu Gly Asp Gly Val
    50                  55                  60

Tyr Thr Leu Asn Ser Glu Lys Gln Trp Val Asn Thr Ala Ala Gly Glu
65                  70                  75                  80

Arg Leu Pro Glu Cys Glu Ala Val Cys Gly Lys Pro Lys His Pro Val

```
                    85                  90                  95
Asp Gln Val Gln Arg Ile Ile Gly Gly Ser Leu Asp Ala Lys Gly Ser
                100                 105                 110

Phe Pro Trp Gln Ala Lys Met Val Ser Arg His Glu Leu Ile Thr Gly
            115                 120                 125

Ala Thr Leu Ile Ser Asp Gln Trp Leu Leu Thr Thr Ala Lys Asn Leu
        130                 135                 140

Phe Leu Asn His Ser Glu Asp Ala Thr Ser Lys Asp Ile Ala Pro Thr
145                 150                 155                 160

Leu Lys Leu Tyr Val Gly Lys Met Gln Pro Val Glu Ile Glu Lys Val
                165                 170                 175

Val Ile His Pro Asn Arg Ser Val Val Asp Ile Gly Val Ile Lys Leu
            180                 185                 190

Arg Gln Lys Val Pro Val Asn Glu Arg Val Met Pro Ile Cys Leu Pro
        195                 200                 205

Ser Lys Asp Tyr Ile Ala Pro Gly Arg Met Gly Tyr Val Ser Gly Trp
210                 215                 220

Gly Arg Asn Ala Asn Phe Arg Phe Thr Asp Arg Leu Lys Tyr Val Met
225                 230                 235                 240

Leu Pro Val Ala Asp Gln Asp Ser Cys Met Leu His Tyr Glu Gly Ser
                245                 250                 255

Thr Val Pro Glu Lys Glu Gly Ser Lys Ser Ser Val Gly Val Gln Pro
            260                 265                 270

Ile Leu Asn Glu His Thr Phe Cys Ala Gly Met Thr Lys Tyr Gln Glu
        275                 280                 285

Asp Thr Cys Tyr Gly Asp Ala Gly Ser Ala Phe Ala Ile His Asp Leu
        290                 295                 300

Glu Gln Asp Thr Trp Tyr Ala Ala Gly Ile Leu Ser Phe Asp Lys Ser
305                 310                 315                 320

Cys Ser Val Ala Glu Tyr Gly Val Tyr Val Lys Val Asn Ser Phe Leu
                325                 330                 335

Asp Trp Ile Gln Glu Thr Met Ala Lys Asn
                340                 345

<210> SEQ ID NO 9
<211> LENGTH: 329
<212> TYPE: PRT
<213> ORGANISM: Canis familiaris

<400> SEQUENCE: 9

Glu Asp Thr Gly Ser Glu Ala Thr Asn Thr Glu Val Ser Leu Pro
1               5                   10                  15

Lys Pro Pro Val Ile Glu Asn Gly Tyr Val Glu His Met Ile Arg Tyr
                20                  25                  30

Gln Cys Lys Pro Phe Tyr Lys Leu His Thr Glu Gly Asp Gly Val Tyr
            35                  40                  45

Thr Leu Asn Ser Glu Lys His Trp Thr Asn Lys Ala Val Gly Glu Lys
        50                  55                  60

Leu Pro Glu Cys Glu Ala Val Cys Gly Lys Pro Lys Asn Pro Val Asp
65                  70                  75                  80

Gln Val Gln Arg Ile Met Gly Gly Ser Val Asp Ala Lys Gly Ser Phe
                85                  90                  95

Pro Trp Gln Ala Lys Met Val Ser His Asn Leu Thr Ser Gly Ala
            100                 105                 110
```

-continued

```
Thr Leu Ile Asn Glu Gln Trp Leu Thr Thr Ala Lys Asn Leu Phe
            115                 120                 125
Leu Gly His Lys Asp Asp Ala Lys Ala Asn Asp Ile Ala Pro Thr Leu
        130                 135                 140
Lys Leu Tyr Val Gly Lys Asn Gln Leu Val Glu Val Glu Lys Val Val
145                 150                 155                 160
Leu His Pro Asp Tyr Ser Lys Val Asp Ile Gly Leu Ile Lys Leu Lys
                165                 170                 175
Gln Lys Val Pro Ile Asp Glu Arg Val Met Pro Ile Cys Leu Pro Ser
            180                 185                 190
Lys Asp Tyr Ala Glu Val Gly Arg Ile Gly Tyr Val Ser Gly Trp Gly
        195                 200                 205
Arg Asn Ser Asn Phe Asn Phe Thr Glu Leu Leu Lys Tyr Val Met Leu
210                 215                 220
Pro Val Ala Asp Gln Asp Lys Cys Val Gln His Tyr Glu Gly Ser Thr
225                 230                 235                 240
Val Pro Glu Lys Lys Ser Pro Lys Ser Pro Val Gly Val Gln Pro Ile
                245                 250                 255
Leu Asn Glu His Thr Phe Cys Ala Gly Met Ser Lys Phe Gln Glu Asp
            260                 265                 270
Thr Cys Tyr Gly Asp Ala Gly Ser Ala Phe Ala Val His Asp Gln Asp
        275                 280                 285
Glu Asp Thr Trp Tyr Ala Ala Gly Ile Leu Ser Phe Asp Lys Ser Cys
    290                 295                 300
Thr Val Ala Glu Tyr Gly Val Tyr Val Lys Val Pro Ser Val Leu Ala
305                 310                 315                 320
Trp Val Gln Glu Thr Ile Ala Gly Asn
                325

<210> SEQ ID NO 10
<211> LENGTH: 1116
<212> TYPE: PRT
<213> ORGANISM: Homo sapiens

<400> SEQUENCE: 10

Met Val Leu Leu Glu Asp Ser Gly Ser Ala Asp Phe Arg Arg His Phe
1               5                   10                  15
Val Asn Leu Ser Pro Phe Thr Ile Thr Val Val Leu Leu Leu Ser Ala
            20                  25                  30
Cys Phe Val Thr Ser Ser Leu Gly Gly Thr Asp Lys Glu Leu Arg Leu
        35                  40                  45
Val Asp Gly Glu Asn Lys Cys Ser Gly Arg Val Glu Val Lys Val Gln
    50                  55                  60
Glu Glu Trp Gly Thr Val Cys Asn Asn Gly Trp Ser Met Glu Ala Val
65                  70                  75                  80
Ser Val Ile Cys Asn Gln Leu Gly Cys Pro Thr Ala Ile Lys Ala Pro
                85                  90                  95
Gly Trp Ala Asn Ser Ser Ala Gly Ser Gly Arg Ile Trp Met Asp His
            100                 105                 110
Val Ser Cys Arg Gly Asn Glu Ser Ala Leu Trp Asp Cys Lys His Asp
        115                 120                 125
Gly Trp Gly Lys His Ser Asn Cys Thr His Gln Gln Asp Ala Gly Val
    130                 135                 140
Thr Cys Ser Asp Gly Ser Asn Leu Glu Met Arg Leu Thr Arg Gly Gly
145                 150                 155                 160
```

-continued

```
Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
        195                 200                 205

Phe Gly Glu Gly Ser Gly Pro Ile Trp Phe Asp Asp Leu Ile Cys Asn
    210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
        275                 280                 285

Gly Trp Asp Ser Tyr Asp Ala Ala Val Ala Cys Lys Gln Leu Gly Cys
    290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
            340                 345                 350

Asn Glu Asp Ala Gly Val Thr Cys Ser Asp Gly Ser Asp Leu Glu Leu
        355                 360                 365

Arg Leu Arg Gly Gly Gly Ser Arg Cys Ala Gly Thr Val Glu Val Glu
    370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
        435                 440                 445

Asn Trp Gln Trp Gly Gly Leu Thr Cys Asp His Tyr Glu Glu Ala Lys
    450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
            500                 505                 510

Glu Leu Gln Cys Gly Thr Val Val Ser Ile Leu Gly Gly Ala His Phe
        515                 520                 525

Gly Glu Gly Asn Gly Gln Ile Trp Ala Glu Glu Phe Gln Cys Glu Gly
    530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Arg Tyr Thr
                565                 570                 575
```

```
Glu Ile Arg Leu Val Asn Gly Lys Thr Pro Cys Glu Gly Arg Val Glu
            580                 585                 590

Leu Lys Thr Leu Gly Ala Trp Gly Ser Leu Cys Asn Ser His Trp Asp
        595                 600                 605

Ile Glu Asp Ala His Val Leu Cys Gln Gln Leu Lys Cys Gly Val Ala
            610                 615                 620

Leu Ser Thr Pro Gly Gly Ala Arg Phe Gly Lys Gly Asn Gly Gln Ile
625                 630                 635                 640

Trp Arg His Met Phe His Cys Thr Gly Thr Glu Gln His Met Gly Asp
            645                 650                 655

Cys Pro Val Thr Ala Leu Gly Ala Ser Leu Cys Pro Ser Glu Gln Val
            660                 665                 670

Ala Ser Val Ile Cys Ser Gly Asn Gln Ser Gln Thr Leu Ser Ser Cys
            675                 680                 685

Asn Ser Ser Ser Leu Gly Pro Thr Arg Pro Thr Ile Pro Glu Glu Ser
            690                 695                 700

Ala Val Ala Cys Ile Glu Ser Gly Gln Leu Arg Leu Val Asn Gly Gly
705                 710                 715                 720

Gly Arg Cys Ala Gly Arg Val Glu Ile Tyr His Glu Gly Ser Trp Gly
                725                 730                 735

Thr Ile Cys Asp Asp Ser Trp Asp Leu Ser Asp Ala His Val Val Cys
            740                 745                 750

Arg Gln Leu Gly Cys Gly Glu Ala Ile Asn Ala Thr Gly Ser Ala His
            755                 760                 765

Phe Gly Glu Gly Thr Gly Pro Ile Trp Leu Asp Glu Met Lys Cys Asn
770                 775                 780

Gly Lys Glu Ser Arg Ile Trp Gln Cys His Ser His Gly Trp Gly Gln
785                 790                 795                 800

Gln Asn Cys Arg His Lys Glu Asp Ala Gly Val Ile Cys Ser Glu Phe
            805                 810                 815

Met Ser Leu Arg Leu Thr Ser Glu Ala Ser Arg Glu Ala Cys Ala Gly
            820                 825                 830

Arg Leu Glu Val Phe Tyr Asn Gly Ala Trp Gly Thr Val Gly Lys Ser
            835                 840                 845

Ser Met Ser Glu Thr Thr Val Gly Val Val Cys Arg Gln Leu Gly Cys
850                 855                 860

Ala Asp Lys Gly Lys Ile Asn Pro Ala Ser Leu Asp Lys Ala Met Ser
865                 870                 875                 880

Ile Pro Met Trp Val Asp Asn Val Gln Cys Pro Lys Gly Pro Asp Thr
            885                 890                 895

Leu Trp Gln Cys Pro Ser Ser Pro Trp Glu Lys Arg Leu Ala Ser Pro
            900                 905                 910

Ser Glu Glu Thr Trp Ile Thr Cys Asp Asn Lys Ile Arg Leu Gln Glu
            915                 920                 925

Gly Pro Thr Ser Cys Ser Gly Arg Val Glu Ile Trp His Gly Gly Ser
            930                 935                 940

Trp Gly Thr Val Cys Asp Asp Ser Trp Asp Leu Asp Asp Ala Gln Val
945                 950                 955                 960

Val Cys Gln Gln Leu Gly Cys Gly Pro Ala Leu Lys Ala Phe Lys Glu
                965                 970                 975

Ala Glu Phe Gly Gln Gly Thr Gly Pro Ile Trp Leu Asn Glu Val Lys
            980                 985                 990

Cys Lys Gly Asn Glu Ser Ser Leu Trp Asp Cys Pro Ala Arg Arg Trp
```

```
              995                 1000                1005
Gly His Ser Glu Cys Gly His Lys Glu Asp Ala Ala Val Asn Cys
    1010                1015                1020

Thr Asp Ile Ser Val Gln Lys Thr Pro Gln Lys Ala Thr Thr Gly
    1025                1030                1035

Arg Ser Ser Arg Gln Ser Ser Phe Ile Ala Val Gly Ile Leu Gly
    1040                1045                1050

Val Val Leu Leu Ala Ile Phe Val Ala Leu Phe Phe Leu Thr Lys
    1055                1060                1065

Lys Arg Arg Gln Arg Gln Arg Leu Ala Val Ser Ser Arg Gly Glu
    1070                1075                1080

Asn Leu Val His Gln Ile Gln Tyr Arg Glu Met Asn Ser Cys Leu
    1085                1090                1095

Asn Ala Asp Asp Leu Asp Leu Met Asn Ser Ser Gly Gly His Ser
    1100                1105                1110

Glu Pro His
    1115

<210> SEQ ID NO 11
<211> LENGTH: 1149
<212> TYPE: PRT
<213> ORGANISM: Homo sapiens

<400> SEQUENCE: 11

Met Val Leu Leu Glu Asp Ser Gly Ser Ala Asp Phe Arg Arg His Phe
1               5                   10                  15

Val Asn Leu Ser Pro Phe Thr Ile Thr Val Val Leu Leu Leu Ser Ala
                20                  25                  30

Cys Phe Val Thr Ser Ser Leu Gly Gly Thr Asp Lys Glu Leu Arg Leu
        35                  40                  45

Val Asp Gly Glu Asn Lys Cys Ser Gly Arg Val Glu Val Lys Val Gln
    50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
        100                 105                 110

Val Ser Cys Arg Gly Asn Glu Ser Ala Leu Trp Asp Cys Lys His Asp
    115                 120                 125

Gly Trp Gly Lys His Ser Asn Cys Thr His Gln Gln Asp Ala Gly Val
130                 135                 140

Thr Cys Ser Asp Gly Ser Asn Leu Glu Met Arg Leu Thr Arg Gly Gly
145                 150                 155                 160

Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
        180                 185                 190

Arg Gln Leu Glu Cys Gly Ser Ala Val Ser Phe Ser Gly Ser Ser Asn
    195                 200                 205

Phe Gly Glu Gly Ser Gly Pro Ile Trp Phe Asp Asp Leu Ile Cys Asn
210                 215                 220

Gly Asn Glu Ser Ala Leu Trp Asn Cys Lys His Gln Gly Trp Gly Lys
225                 230                 235                 240
```

-continued

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
        275                 280                 285

Gly Trp Asp Ser Tyr Asp Ala Val Ala Cys Lys Gln Leu Gly Cys
    290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
            340                 345                 350

Asn Glu Asp Ala Gly Val Thr Cys Ser Asp Gly Ser Asp Leu Glu Leu
        355                 360                 365

Arg Leu Arg Gly Gly Gly Ser Arg Cys Ala Gly Thr Val Glu Val Glu
    370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
        435                 440                 445

Asn Trp Gln Trp Gly Gly Leu Thr Cys Asp His Tyr Glu Glu Ala Lys
    450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
            500                 505                 510

Glu Leu Gln Cys Gly Thr Val Val Ser Ile Leu Gly Gly Ala His Phe
        515                 520                 525

Gly Glu Gly Asn Gly Gln Ile Trp Ala Glu Glu Phe Gln Cys Glu Gly
    530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Ser Lys Thr
                565                 570                 575

Gln Lys Thr Ser Leu Ile Gly Ser Tyr Thr Val Lys Gly Thr Gly Leu
            580                 585                 590

Gly Ser His Ser Cys Leu Phe Leu Lys Pro Cys Leu Leu Pro Gly Tyr
        595                 600                 605

Thr Glu Ile Arg Leu Val Asn Gly Lys Thr Pro Cys Glu Gly Arg Val
    610                 615                 620

Glu Leu Lys Thr Leu Gly Ala Trp Gly Ser Leu Cys Asn Ser His Trp
625                 630                 635                 640

Asp Ile Glu Asp Ala His Val Leu Cys Gln Gln Leu Lys Cys Gly Val
                645                 650                 655

Ala Leu Ser Thr Pro Gly Gly Ala Arg Phe Gly Lys Gly Asn Gly Gln

```
                      660                665                 670
    Ile Trp Arg His Met Phe His Cys Thr Gly Thr Glu Gln His Met Gly
                      675                680                 685
    Asp Cys Pro Val Thr Ala Leu Gly Ala Ser Leu Cys Pro Ser Glu Gln
                      690                695                 700
    Val Ala Ser Val Ile Cys Ser Gly Asn Gln Ser Gln Thr Leu Ser Ser
    705                710                715                 720
    Cys Asn Ser Ser Leu Gly Pro Thr Arg Pro Thr Ile Pro Glu Glu
                      725                730                 735
    Ser Ala Val Ala Cys Ile Glu Ser Gly Gln Leu Arg Leu Val Asn Gly
                      740                745                 750
    Gly Gly Arg Cys Ala Gly Arg Val Glu Ile Tyr His Glu Gly Ser Trp
                      755                760                 765
    Gly Thr Ile Cys Asp Asp Ser Trp Asp Leu Ser Asp Ala His Val Val
                      770                775                 780
    Cys Arg Gln Leu Gly Cys Gly Glu Ala Ile Asn Ala Thr Gly Ser Ala
    785                790                795                 800
    His Phe Gly Glu Gly Thr Gly Pro Ile Trp Leu Asp Glu Met Lys Cys
                      805                810                 815
    Asn Gly Lys Glu Ser Arg Ile Trp Gln Cys His Ser His Gly Trp Gly
                      820                825                 830
    Gln Gln Asn Cys Arg His Lys Glu Asp Ala Gly Val Ile Cys Ser Glu
                      835                840                 845
    Phe Met Ser Leu Arg Leu Thr Ser Glu Ala Ser Arg Glu Ala Cys Ala
    850                855                860
    Gly Arg Leu Glu Val Phe Tyr Asn Gly Ala Trp Gly Thr Val Gly Lys
    865                870                875                 880
    Ser Ser Met Ser Glu Thr Thr Val Gly Val Val Cys Arg Gln Leu Gly
                      885                890                 895
    Cys Ala Asp Lys Gly Lys Ile Asn Pro Ala Ser Leu Asp Lys Ala Met
                      900                905                 910
    Ser Ile Pro Met Trp Val Asp Asn Val Gln Cys Pro Lys Gly Pro Asp
                      915                920                 925
    Thr Leu Trp Gln Cys Pro Ser Ser Pro Trp Glu Lys Arg Leu Ala Ser
                      930                935                 940
    Pro Ser Glu Glu Thr Trp Ile Thr Cys Asp Asn Lys Ile Arg Leu Gln
    945                950                955                 960
    Glu Gly Pro Thr Ser Cys Ser Gly Arg Val Glu Ile Trp His Gly Gly
                      965                970                 975
    Ser Trp Gly Thr Val Cys Asp Asp Ser Trp Asp Leu Asp Asp Ala Gln
                      980                985                 990
    Val Val Cys Gln Gln Leu Gly Cys Gly Pro Ala Leu Lys Ala Phe Lys
                      995                1000                1005
    Glu Ala Glu Phe Gly Gln Gly Thr Gly Pro Ile Trp Leu Asn Glu
                      1010               1015                1020
    Val Lys Cys Lys Gly Asn Glu Ser Ser Leu Trp Asp Cys Pro Ala
                      1025               1030                1035
    Arg Arg Trp Gly His Ser Glu Cys Gly His Lys Glu Asp Ala Ala
                      1040               1045                1050
    Val Asn Cys Thr Asp Ile Ser Val Gln Lys Thr Pro Gln Lys Ala
                      1055               1060                1065
    Thr Thr Gly Arg Ser Ser Arg Gln Ser Ser Phe Ile Ala Val Gly
                      1070               1075                1080
```

Ile Leu Gly Val Val Leu Leu Ala Ile Phe Val Ala Leu Phe Phe
    1085                1090                1095

Leu Thr Lys Lys Arg Arg Gln Arg Gln Arg Leu Ala Val Ser Ser
    1100                1105                1110

Arg Gly Glu Asn Leu Val His Gln Ile Gln Tyr Arg Glu Met Asn
    1115                1120                1125

Ser Cys Leu Asn Ala Asp Asp Leu Asp Leu Met Asn Ser Ser Gly
    1130                1135                1140

Gly His Ser Glu Pro His
    1145

<210> SEQ ID NO 12
<211> LENGTH: 1156
<212> TYPE: PRT
<213> ORGANISM: Homo sapiens

<400> SEQUENCE: 12

Met Val Leu Leu Glu Asp Ser Gly Ser Ala Asp Phe Arg Arg His Phe
1               5                   10                  15

Val Asn Leu Ser Pro Phe Thr Ile Thr Val Leu Leu Ser Ala
            20                  25                  30

Cys Phe Val Thr Ser Ser Leu Gly Gly Thr Asp Lys Glu Leu Arg Leu
            35                  40                  45

Val Asp Gly Glu Asn Lys Cys Ser Gly Arg Val Glu Val Lys Val Gln
        50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
            100                 105                 110

Val Ser Cys Arg Gly Asn Glu Ser Ala Leu Trp Asp Cys Lys His Asp
            115                 120                 125

Gly Trp Gly Lys His Ser Asn Cys Thr His Gln Gln Asp Ala Gly Val
        130                 135                 140

Thr Cys Ser Asp Gly Ser Asn Leu Glu Met Arg Leu Thr Arg Gly Gly
145                 150                 155                 160

Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
            195                 200                 205

Phe Gly Glu Gly Ser Gly Pro Ile Trp Phe Asp Asp Leu Ile Cys Asn
        210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
            275                 280                 285

Gly Trp Asp Ser Tyr Asp Ala Ala Val Ala Cys Lys Gln Leu Gly Cys

```
            290                 295                 300
Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
                340                 345                 350

Asn Glu Asp Ala Gly Val Thr Cys Ser Asp Gly Ser Asp Leu Glu Leu
            355                 360                 365

Arg Leu Arg Gly Gly Ser Arg Cys Ala Gly Thr Val Glu Val Glu
370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
                420                 425                 430

Phe Leu Ser Ser Cys Asn Gly Asn Glu Thr Ser Leu Trp Asp Cys Lys
            435                 440                 445

Asn Trp Gln Trp Gly Gly Leu Thr Cys Asp His Tyr Glu Glu Ala Lys
450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
                500                 505                 510

Glu Leu Gln Cys Gly Thr Val Val Ser Ile Leu Gly Gly Ala His Phe
            515                 520                 525

Gly Glu Gly Asn Gly Gln Ile Trp Ala Glu Glu Phe Gln Cys Glu Gly
530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Arg Tyr Thr
                565                 570                 575

Glu Ile Arg Leu Val Asn Gly Lys Thr Pro Cys Glu Gly Arg Val Glu
                580                 585                 590

Leu Lys Thr Leu Gly Ala Trp Gly Ser Leu Cys Asn Ser His Trp Asp
            595                 600                 605

Ile Glu Asp Ala His Val Leu Cys Gln Gln Leu Lys Cys Gly Val Ala
610                 615                 620

Leu Ser Thr Pro Gly Gly Ala Arg Phe Gly Lys Gly Asn Gly Gln Ile
625                 630                 635                 640

Trp Arg His Met Phe His Cys Thr Gly Thr Glu Gln His Met Gly Asp
                645                 650                 655

Cys Pro Val Thr Ala Leu Gly Ala Ser Leu Cys Pro Ser Glu Gln Val
                660                 665                 670

Ala Ser Val Ile Cys Ser Gly Asn Gln Ser Gln Thr Leu Ser Ser Cys
            675                 680                 685

Asn Ser Ser Ser Leu Gly Pro Thr Arg Pro Thr Ile Pro Glu Glu Ser
690                 695                 700

Ala Val Ala Cys Ile Glu Ser Gly Gln Leu Arg Leu Val Asn Gly Gly
705                 710                 715                 720
```

```
Gly Arg Cys Ala Gly Arg Val Glu Ile Tyr His Gly Ser Trp Gly
            725                 730                 735

Thr Ile Cys Asp Asp Ser Trp Asp Leu Ser Asp Ala His Val Val Cys
            740                 745                 750

Arg Gln Leu Gly Cys Gly Glu Ala Ile Asn Ala Thr Gly Ser Ala His
            755                 760                 765

Phe Gly Glu Gly Thr Gly Pro Ile Trp Leu Asp Glu Met Lys Cys Asn
            770                 775                 780

Gly Lys Glu Ser Arg Ile Trp Gln Cys His Ser His Gly Trp Gly Gln
785                 790                 795                 800

Gln Asn Cys Arg His Lys Glu Asp Ala Gly Val Ile Cys Ser Glu Phe
            805                 810                 815

Met Ser Leu Arg Leu Thr Ser Glu Ala Ser Arg Glu Ala Cys Ala Gly
            820                 825                 830

Arg Leu Glu Val Phe Tyr Asn Gly Ala Trp Gly Thr Val Gly Lys Ser
            835                 840                 845

Ser Met Ser Glu Thr Thr Val Gly Val Val Cys Arg Gln Leu Gly Cys
            850                 855                 860

Ala Asp Lys Gly Lys Ile Asn Pro Ala Ser Leu Asp Lys Ala Met Ser
865                 870                 875                 880

Ile Pro Met Trp Val Asp Asn Val Gln Cys Pro Lys Gly Pro Asp Thr
            885                 890                 895

Leu Trp Gln Cys Pro Ser Ser Pro Trp Glu Lys Arg Leu Ala Ser Pro
            900                 905                 910

Ser Glu Glu Thr Trp Ile Thr Cys Asp Asn Lys Ile Arg Leu Gln Glu
            915                 920                 925

Gly Pro Thr Ser Cys Ser Gly Arg Val Glu Ile Trp His Gly Gly Ser
            930                 935                 940

Trp Gly Thr Val Cys Asp Asp Ser Trp Asp Leu Asp Asp Ala Gln Val
945                 950                 955                 960

Val Cys Gln Gln Leu Gly Cys Gly Pro Ala Leu Lys Ala Phe Lys Glu
            965                 970                 975

Ala Glu Phe Gly Gln Gly Thr Gly Pro Ile Trp Leu Asn Glu Val Lys
            980                 985                 990

Cys Lys Gly Asn Glu Ser Ser Leu Trp Asp Cys Pro Ala Arg Arg Trp
            995                 1000                1005

Gly His Ser Glu Cys Gly His Lys Glu Asp Ala Ala Val Asn Cys
            1010                1015                1020

Thr Asp Ile Ser Val Gln Lys Thr Pro Gln Lys Ala Thr Thr Gly
            1025                1030                1035

Arg Ser Ser Arg Gln Ser Ser Phe Ile Ala Val Gly Ile Leu Gly
            1040                1045                1050

Val Val Leu Leu Ala Ile Phe Val Ala Leu Phe Phe Leu Thr Lys
            1055                1060                1065

Lys Arg Arg Gln Arg Gln Arg Leu Ala Val Ser Ser Arg Gly Glu
            1070                1075                1080

Asn Leu Val His Gln Ile Gln Tyr Arg Glu Met Asn Ser Cys Leu
            1085                1090                1095

Asn Ala Asp Asp Leu Asp Leu Met Asn Ser Ser Gly Leu Trp Val
            1100                1105                1110

Leu Gly Gly Ser Ile Ala Gln Gly Phe Arg Ser Val Ala Ala Val
            1115                1120                1125
```

Glu Ala Gln Thr Phe Tyr Phe Asp Lys Gln Leu Lys Lys Ser Lys
1130                1135                1140

Asn Val Ile Gly Ser Leu Asp Ala Tyr Asn Gly Gln Glu
1145                1150                1155

<210> SEQ ID NO 13
<211> LENGTH: 1151
<212> TYPE: PRT
<213> ORGANISM: Homo sapiens

<400> SEQUENCE: 13

Met Val Leu Leu Glu Asp Ser Gly Ser Ala Asp Phe Arg Arg His Phe
1               5                   10                  15

Val Asn Leu Ser Pro Phe Thr Ile Thr Val Leu Leu Leu Ser Ala
            20                  25                  30

Cys Phe Val Thr Ser Ser Leu Gly Gly Thr Asp Lys Glu Leu Arg Leu
        35                  40                  45

Val Asp Gly Glu Asn Lys Cys Ser Gly Arg Val Glu Val Lys Val Gln
    50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
            100                 105                 110

Val Ser Cys Arg Gly Asn Glu Ser Ala Leu Trp Asp Cys Lys His Asp
        115                 120                 125

Gly Trp Gly Lys His Ser Asn Cys Thr His Gln Gln Asp Ala Gly Val
    130                 135                 140

Thr Cys Ser Asp Gly Ser Asn Leu Glu Met Arg Leu Thr Arg Gly Gly
145                 150                 155                 160

Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
        195                 200                 205

Phe Gly Glu Gly Ser Gly Pro Ile Trp Phe Asp Asp Leu Ile Cys Asn
    210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
        275                 280                 285

Gly Trp Asp Ser Tyr Asp Ala Ala Val Ala Cys Lys Gln Leu Gly Cys
    290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
            340                 345                 350

```
Asn Glu Asp Ala Gly Val Thr Cys Ser Asp Gly Ser Asp Leu Glu Leu
        355                 360                 365

Arg Leu Arg Gly Gly Gly Ser Arg Cys Ala Gly Thr Val Glu Val Glu
        370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
        435                 440                 445

Asn Trp Gln Trp Gly Gly Leu Thr Cys Asp His Tyr Glu Glu Ala Lys
        450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
            500                 505                 510

Glu Leu Gln Cys Gly Thr Val Val Ser Ile Leu Gly Gly Ala His Phe
        515                 520                 525

Gly Glu Gly Asn Gly Gln Ile Trp Ala Glu Glu Phe Gln Cys Glu Gly
        530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Arg Tyr Thr
                565                 570                 575

Glu Ile Arg Leu Val Asn Gly Lys Thr Pro Cys Glu Gly Arg Val Glu
            580                 585                 590

Leu Lys Thr Leu Gly Ala Trp Gly Ser Leu Cys Asn Ser His Trp Asp
        595                 600                 605

Ile Glu Asp Ala His Val Leu Cys Gln Gln Leu Lys Cys Gly Val Ala
        610                 615                 620

Leu Ser Thr Pro Gly Gly Ala Arg Phe Gly Lys Gly Asn Gly Gln Ile
625                 630                 635                 640

Trp Arg His Met Phe His Cys Thr Gly Thr Glu Gln His Met Gly Asp
                645                 650                 655

Cys Pro Val Thr Ala Leu Gly Ala Ser Leu Cys Pro Ser Glu Gln Val
            660                 665                 670

Ala Ser Val Ile Cys Ser Gly Asn Gln Ser Gln Thr Leu Ser Ser Cys
        675                 680                 685

Asn Ser Ser Ser Leu Gly Pro Thr Arg Pro Thr Ile Pro Glu Glu Ser
        690                 695                 700

Ala Val Ala Cys Ile Glu Ser Gly Gln Leu Arg Leu Val Asn Gly Gly
705                 710                 715                 720

Gly Arg Cys Ala Gly Arg Val Glu Ile Tyr His Glu Gly Ser Trp Gly
                725                 730                 735

Thr Ile Cys Asp Asp Ser Trp Asp Leu Ser Asp Ala His Val Val Cys
            740                 745                 750

Arg Gln Leu Gly Cys Gly Glu Ala Ile Asn Ala Thr Gly Ser Ala His
        755                 760                 765
```

Phe Gly Glu Gly Thr Gly Pro Ile Trp Leu Asp Glu Met Lys Cys Asn
770                 775                 780

Gly Lys Glu Ser Arg Ile Trp Gln Cys His Ser His Gly Trp Gly Gln
785                 790                 795                 800

Gln Asn Cys Arg His Lys Glu Asp Ala Gly Val Ile Cys Ser Glu Phe
            805                 810                 815

Met Ser Leu Arg Leu Thr Ser Glu Ala Ser Arg Glu Ala Cys Ala Gly
                820                 825                 830

Arg Leu Glu Val Phe Tyr Asn Gly Ala Trp Gly Thr Val Gly Lys Ser
                    835                 840                 845

Ser Met Ser Glu Thr Thr Val Gly Val Val Cys Arg Gln Leu Gly Cys
850                 855                 860

Ala Asp Lys Gly Lys Ile Asn Pro Ala Ser Leu Asp Lys Ala Met Ser
865                 870                 875                 880

Ile Pro Met Trp Val Asp Asn Val Gln Cys Pro Lys Gly Pro Asp Thr
                    885                 890                 895

Leu Trp Gln Cys Pro Ser Ser Pro Trp Glu Lys Arg Leu Ala Ser Pro
                900                 905                 910

Ser Glu Glu Thr Trp Ile Thr Cys Asp Asn Lys Ile Arg Leu Gln Glu
                915                 920                 925

Gly Pro Thr Ser Cys Ser Gly Arg Val Glu Ile Trp His Gly Gly Ser
930                 935                 940

Trp Gly Thr Val Cys Asp Asp Ser Trp Asp Leu Asp Asp Ala Gln Val
945                 950                 955                 960

Val Cys Gln Gln Leu Gly Cys Gly Pro Ala Leu Lys Ala Phe Lys Glu
                965                 970                 975

Ala Glu Phe Gly Gln Gly Thr Gly Pro Ile Trp Leu Asn Glu Val Lys
                980                 985                 990

Cys Lys Gly Asn Glu Ser Ser Leu Trp Asp Cys Pro Ala Arg Arg Trp
                995                 1000                1005

Gly His Ser Glu Cys Gly His Lys Glu Asp Ala Ala Val Asn Cys
        1010                1015                1020

Thr Asp Ile Ser Val Gln Lys Thr Pro Gln Lys Ala Thr Thr Gly
        1025                1030                1035

Arg Ser Ser Arg Gln Ser Ser Phe Ile Ala Val Gly Ile Leu Gly
        1040                1045                1050

Val Val Leu Leu Ala Ile Phe Val Ala Leu Phe Phe Leu Thr Lys
        1055                1060                1065

Lys Arg Arg Gln Arg Gln Arg Leu Ala Val Ser Ser Arg Gly Glu
        1070                1075                1080

Asn Leu Val His Gln Ile Gln Tyr Arg Glu Met Asn Ser Cys Leu
        1085                1090                1095

Asn Ala Asp Asp Leu Asp Leu Met Asn Ser Ser Glu Asn Ser His
        1100                1105                1110

Glu Ser Ala Asp Phe Ser Ala Ala Glu Leu Ile Ser Val Ser Lys
        1115                1120                1125

Phe Leu Pro Ile Ser Gly Met Glu Lys Glu Ala Ile Leu Ser His
        1130                1135                1140

Thr Glu Lys Glu Asn Gly Asn Leu
        1145                1150

<210> SEQ ID NO 14
<211> LENGTH: 141
<212> TYPE: PRT

<213> ORGANISM: Homo sapiens

<400> SEQUENCE: 14

Val Leu Ser Pro Ala Asp Lys Thr Asn Val Lys Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 15
<211> LENGTH: 146
<212> TYPE: PRT
<213> ORGANISM: Homo sapiens

<400> SEQUENCE: 15

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 16
<211> LENGTH: 146
<212> TYPE: PRT
<213> ORGANISM: Homo sapiens

<400> SEQUENCE: 16

Val His Leu Thr Pro Glu Glu Lys Thr Ala Val Asn Ala Leu Trp Gly
1               5                   10                  15

Lys Val Asn Val Asp Ala Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Ser Pro Asp Ala Val Met Gly Asn Pro Lys Val Lys Ala His Gly
 50                  55                  60

Lys Lys Val Leu Gly Ala Phe Ser Asp Gly Leu Ala His Leu Asp Asn
65                  70                  75                  80

Leu Lys Gly Thr Phe Ser Gln Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala Arg Asn Phe Gly Lys Glu Phe Thr Pro Gln Met Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 17
<211> LENGTH: 146
<212> TYPE: PRT
<213> ORGANISM: Homo sapiens

<400> SEQUENCE: 17

Gly His Phe Thr Glu Glu Asp Lys Ala Thr Ile Thr Ser Leu Trp Gly
1               5                   10                  15

Lys Val Asn Val Glu Asp Ala Gly Gly Glu Thr Leu Gly Arg Leu Leu
            20                  25                  30

Val Val Tyr Pro Trp Thr Gln Arg Phe Phe Asp Ser Phe Gly Asn Leu
        35                  40                  45

Ser Ser Ala Ser Ala Ile Met Gly Asn Pro Lys Val Lys Ala His Gly
 50                  55                  60

Lys Lys Val Leu Thr Ser Leu Gly Asp Ala Ile Lys His Leu Asp Asp
65                  70                  75                  80

Leu Lys Gly Thr Phe Ala Gln Leu Ser Glu Leu His Cys Asp Lys Leu
                85                  90                  95

His Val Asp Pro Glu Asn Phe Lys Leu Leu Gly Asn Val Leu Val Thr
            100                 105                 110

Val Leu Ala Ile His Phe Gly Lys Glu Phe Thr Pro Glu Val Gln Ala
        115                 120                 125

Ser Trp Gln Lys Met Val Thr Ala Val Ala Ser Ala Leu Ser Ser Arg
    130                 135                 140

Tyr His
145

<210> SEQ ID NO 18
<211> LENGTH: 141
<212> TYPE: PRT
<213> ORGANISM: Homo sapiens

<400> SEQUENCE: 18

Ala Leu Ser Ala Glu Asp Arg Ala Leu Val Arg Ala Leu Trp Lys Lys
1               5                   10                  15

Leu Gly Ser Asn Val Gly Val Tyr Thr Thr Glu Ala Leu Glu Arg Thr
            20                  25                  30

```
Phe Leu Ala Phe Pro Ala Thr Lys Thr Tyr Phe Ser His Leu Asp Leu
            35                  40                  45

Ser Pro Gly Ser Ser Gln Val Arg Ala His Gly Gln Lys Val Ala Asp
 50                  55                  60

Ala Leu Ser Leu Ala Val Glu Arg Leu Asp Asp Leu Pro His Ala Leu
 65                  70                  75                  80

Ser Ala Leu Ser His Leu His Ala Cys Gln Leu Arg Val Asp Pro Ala
                85                  90                  95

Ser Phe Gln Leu Leu Gly His Cys Leu Leu Val Thr Leu Ala Arg His
                100                 105                 110

Tyr Pro Gly Asp Phe Ser Pro Ala Leu Gln Ala Ser Leu Asp Lys Phe
            115                 120                 125

Leu Ser His Val Ile Ser Ala Leu Val Ser Glu Tyr Arg
        130                 135                 140

<210> SEQ ID NO 19
<211> LENGTH: 141
<212> TYPE: PRT
<213> ORGANISM: Homo sapiens

<400> SEQUENCE: 19

Ser Leu Thr Lys Thr Glu Arg Thr Ile Ile Val Ser Met Trp Ala Lys
1               5                   10                  15

Ile Ser Thr Gln Ala Asp Thr Ile Gly Thr Glu Thr Leu Glu Arg Leu
            20                  25                  30

Phe Leu Ser His Pro Gln Thr Lys Thr Tyr Phe Pro His Phe Asp Leu
            35                  40                  45

His Pro Gly Ser Ala Gln Leu Arg Ala His Gly Ser Lys Val Val Ala
 50                  55                  60

Ala Val Gly Asp Ala Val Lys Ser Ile Asp Asp Ile Gly Gly Ala Leu
 65                  70                  75                  80

Ser Lys Leu Ser Glu Leu His Ala Tyr Ile Leu Arg Val Asp Pro Val
                85                  90                  95

Asn Phe Lys Leu Leu Ser His Cys Leu Leu Val Thr Leu Ala Ala Arg
                100                 105                 110

Phe Pro Ala Asp Phe Thr Ala Glu Ala His Ala Ala Trp Asp Lys Phe
            115                 120                 125

Leu Ser Val Val Ser Ser Val Leu Thr Glu Lys Tyr Arg
        130                 135                 140

<210> SEQ ID NO 20
<211> LENGTH: 146
<212> TYPE: PRT
<213> ORGANISM: Homo sapiens

<400> SEQUENCE: 20

Val His Phe Thr Ala Glu Glu Lys Ala Ala Val Thr Ser Leu Trp Ser
1               5                   10                  15

Lys Met Asn Val Glu Glu Ala Gly Gly Glu Ala Leu Gly Arg Leu Leu
            20                  25                  30

Val Val Tyr Pro Trp Thr Gln Arg Phe Phe Asp Ser Phe Gly Asn Leu
            35                  40                  45

Ser Ser Pro Ser Ala Ile Leu Gly Asn Pro Lys Val Lys Ala His Gly
 50                  55                  60

Lys Lys Val Leu Thr Ser Phe Gly Asp Ala Ile Lys Asn Met Asp Asn
 65                  70                  75                  80
```

Leu Lys Pro Ala Phe Ala Lys Leu Ser Glu Leu His Cys Asp Lys Leu
                85                  90                  95

His Val Asp Pro Glu Asn Phe Lys Leu Leu Gly Asn Val Met Val Ile
                100                 105                 110

Ile Leu Ala Thr His Phe Gly Lys Glu Phe Thr Pro Gly Val Gln Ala
                115                 120                 125

Ala Trp Gln Lys Leu Val Ser Ala Val Ala Ile Ala Leu Ala His Lys
        130                 135                 140

Tyr His
145

<210> SEQ ID NO 21
<211> LENGTH: 147
<212> TYPE: PRT
<213> ORGANISM: Homo sapiens
<220> FEATURE:
<221> NAME/KEY: misc_feature
<222> LOCATION: (15)..(15)
<223> OTHER INFORMATION: Xaa is unknown

<400> SEQUENCE: 21

Met Val His Leu Thr Pro Val Glu Lys Ser Ala Val Thr Ala Xaa Trp
1               5                   10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
                35                  40                  45

Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
                100                 105                 110

Cys Val Leu Ala His His Phe Gly Lys Glu Phe Thr Pro Pro Val Gln
                115                 120                 125

Ala Ala Tyr Gln Lys Val Val Ala Gly Val Ala Asn Ala Leu Ala His
        130                 135                 140

Lys Tyr His
145

<210> SEQ ID NO 22
<211> LENGTH: 25
<212> TYPE: DNA
<213> ORGANISM: Artificial Sequence
<220> FEATURE:
<223> OTHER INFORMATION: SRCR domain 1-6 forward primer

<400> SEQUENCE: 22
caagcttgga acagacaagg agctg                                         25

<210> SEQ ID NO 23
<211> LENGTH: 26
<212> TYPE: DNA
<213> ORGANISM: Artificial Sequence
<220> FEATURE:
<223> OTHER INFORMATION: SRCR domain 1-6 reverse primer

<400> SEQUENCE: 23

```
cctcgagtcc tgagcagatt acagag                                                    26

<210> SEQ ID NO 24
<211> LENGTH: 25
<212> TYPE: DNA
<213> ORGANISM: Artificial Sequence
<220> FEATURE:
<223> OTHER INFORMATION: SRCR domain 5-9 forward primer

<400> SEQUENCE: 24
caagcttcac agggaaccca gactg                                                     25

<210> SEQ ID NO 25
<211> LENGTH: 25
<212> TYPE: DNA
<213> ORGANISM: Artificial Sequence
<220> FEATURE:
<223> OTHER INFORMATION: SRCR domain 5-9 reverse primer

<400> SEQUENCE: 25
cctcgagatc tgtgcaattc actgc                                                     25

<210> SEQ ID NO 26
<211> LENGTH: 3703
<212> TYPE: DNA
<213> ORGANISM: Homo sapiens
<220> FEATURE:
<221> NAME/KEY: misc_feature
<223> OTHER INFORMATION: cDNA (Genbank Z22968.1) for Human CD163
<220> FEATURE:
<221> NAME/KEY: CDS
<222> LOCATION: (102)..(3452)

<400> SEQUENCE: 26
gaattcttag ttgttttctt tagaagaaca tttctaggga ataatacaag aagatttagg              60
aatcattgaa gttataaatc tttggaatga gcaaactcag a atg gtg cta ctt gaa             116
                                              Met Val Leu Leu Glu
                                                1               5 gac tct gga tct gct gac ttc aga aga cat ttt gtc aac ctg agt ccc               164
Asp Ser Gly Ser Ala Asp Phe Arg Arg His Phe Val Asn Leu Ser Pro
             10                  15                  20 ttc acc att act gtg gtc tta ctt ctc agt gcc tgt ttt gtc acc agt               212
Phe Thr Ile Thr Val Val Leu Leu Leu Ser Ala Cys Phe Val Thr Ser
         25                  30                  35 tct ctt gga gga aca gac aag gag ctg agg cta gtg gat ggt gaa aac               260
Ser Leu Gly Gly Thr Asp Lys Glu Leu Arg Leu Val Asp Gly Glu Asn
     40                  45                  50 aag tgt agc ggg aga gtg gaa gtg aaa gtc cag gag gag tgg gga acg               308
Lys Cys Ser Gly Arg Val Glu Val Lys Val Gln Glu Glu Trp Gly Thr
 55                  60                  65 gtg tgt aat aat ggc tgg agc atg gaa gcg gtc tct gtg att tgt aac               356
Val Cys Asn Asn Gly Trp Ser Met Glu Ala Val Ser Val Ile Cys Asn
 70                  75                  80                  85 cag ctg gga tgt cca act gct atc aaa gcc cct gga tgg gct aat tcc               404
Gln Leu Gly Cys Pro Thr Ala Ile Lys Ala Pro Gly Trp Ala Asn Ser
             90                  95                 100 agt gca ggt tct gga cgc att tgg atg gat cat gtt tct tgt cgt ggg               452
Ser Ala Gly Ser Gly Arg Ile Trp Met Asp His Val Ser Cys Arg Gly
        105                 110                 115 aat gag tca gct ctt tgg gat tgc aaa cat gat gga tgg gga aag cat               500
Asn Glu Ser Ala Leu Trp Asp Cys Lys His Asp Gly Trp Gly Lys His
    120                 125                 130
```

```
agt aac tgt act cac caa caa gat gct gga gtg acc tgc tca gat gga    548
Ser Asn Cys Thr His Gln Gln Asp Ala Gly Val Thr Cys Ser Asp Gly
        135                 140                 145 tcc aat ttg gaa atg agg ctg acg cgt gga ggg aat atg tgt tct gga    596
Ser Asn Leu Glu Met Arg Leu Thr Arg Gly Gly Asn Met Cys Ser Gly
150                 155                 160                 165 aga ata gag atc aaa ttc caa gga cgg tgg gga aca gtg tgt gat gat    644
Arg Ile Glu Ile Lys Phe Gln Gly Arg Trp Gly Thr Val Cys Asp Asp
                170                 175                 180 aac ttc aac ata gat cat gca tct gtc att tgt aga caa ctt gaa tgt    692
Asn Phe Asn Ile Asp His Ala Ser Val Ile Cys Arg Gln Leu Glu Cys
            185                 190                 195 gga agt gct gtc agt ttc tct ggt tca tct aat ttt gga gaa ggc tct    740
Gly Ser Ala Val Ser Phe Ser Gly Ser Ser Asn Phe Gly Glu Gly Ser
        200                 205                 210 gga cca atc tgg ttt gat gat ctt ata tgc aac gga aat gag tca gct    788
Gly Pro Ile Trp Phe Asp Asp Leu Ile Cys Asn Gly Asn Glu Ser Ala
215                 220                 225 ctc tgg aac tgc aaa cat caa gga tgg gga aag cat aac tgt gat cat    836
Leu Trp Asn Cys Lys His Gln Gly Trp Gly Lys His Asn Cys Asp His
230                 235                 240                 245 gct gag gat gct gga gtg att tgc tca aag gga gca gat ctg agc ctg    884
Ala Glu Asp Ala Gly Val Ile Cys Ser Lys Gly Ala Asp Leu Ser Leu
                250                 255                 260 aga ctg gta gat gga gtc act gaa tgt tca gga aga tta gaa gtg aga    932
Arg Leu Val Asp Gly Val Thr Glu Cys Ser Gly Arg Leu Glu Val Arg
            265                 270                 275 ttc caa gga gaa tgg ggg aca ata tgt gat gac ggc tgg gac agt tac    980
Phe Gln Gly Glu Trp Gly Thr Ile Cys Asp Asp Gly Trp Asp Ser Tyr
        280                 285                 290 gat gct gct gtg gca tgc aag caa ctg gga tgt cca act gcc gtc aca   1028
Asp Ala Ala Val Ala Cys Lys Gln Leu Gly Cys Pro Thr Ala Val Thr
295                 300                 305 gcc att ggt cga gtt aac gcc agt aag gga ttt gga cac atc tgg ctt   1076
Ala Ile Gly Arg Val Asn Ala Ser Lys Gly Phe Gly His Ile Trp Leu
310                 315                 320                 325 gac agc gtt tct tgc cag gga cat gaa cct gct gtc tgg caa tgt aaa   1124
Asp Ser Val Ser Cys Gln Gly His Glu Pro Ala Val Trp Gln Cys Lys
                330                 335                 340 cac cat gaa tgg gga aag cat tat tgc aat cac aat gaa gat gct ggc   1172
His His Glu Trp Gly Lys His Tyr Cys Asn His Asn Glu Asp Ala Gly
            345                 350                 355 gtg aca tgt tct gat gga tca gat ctg gag cta aga ctt aga ggt gga   1220
Val Thr Cys Ser Asp Gly Ser Asp Leu Glu Leu Arg Leu Arg Gly Gly
        360                 365                 370 ggc agc cgc tgt gct ggg aca gtt gag gtg gag att cag aga ctg tta   1268
Gly Ser Arg Cys Ala Gly Thr Val Glu Val Glu Ile Gln Arg Leu Leu
375                 380                 385 ggg aag gtg tgt gac aga ggc tgg gga ctg aaa gaa gct gat gtg gtt   1316
Gly Lys Val Cys Asp Arg Gly Trp Gly Leu Lys Glu Ala Asp Val Val
390                 395                 400                 405 tgc agg cag ctg gga tgt gga tct gca ctc aaa aca tct tat caa gtg   1364
Cys Arg Gln Leu Gly Cys Gly Ser Ala Leu Lys Thr Ser Tyr Gln Val
                410                 415                 420 tac tcc aaa atc cag gca aca aac aca tgg ctg ttt cta agt agc tgt   1412
Tyr Ser Lys Ile Gln Ala Thr Asn Thr Trp Leu Phe Leu Ser Ser Cys
            425                 430                 435 aac gga aat gaa act tct ctt tgg gac tgc aag aac tgg caa tgg ggt   1460
Asn Gly Asn Glu Thr Ser Leu Trp Asp Cys Lys Asn Trp Gln Trp Gly
        440                 445                 450
```

```
gga ctt acc tgt gat cac tat gaa gaa gcc aaa att acc tgc tca gcc      1508
Gly Leu Thr Cys Asp His Tyr Glu Glu Ala Lys Ile Thr Cys Ser Ala
        455                 460                 465 cac agg gaa ccc aga ctg gtt gga ggg gac att ccc tgt tct gga cgt      1556
His Arg Glu Pro Arg Leu Val Gly Gly Asp Ile Pro Cys Ser Gly Arg
470                 475                 480                 485 gtt gaa gtg aag cat ggt gac acg tgg ggc tcc atc tgt gat tcg gac      1604
Val Glu Val Lys His Gly Asp Thr Trp Gly Ser Ile Cys Asp Ser Asp
                490                 495                 500 ttc tct ctg gaa gct gcc agc gtt cta tgc agg gaa tta cag tgt ggc      1652
Phe Ser Leu Glu Ala Ala Ser Val Leu Cys Arg Glu Leu Gln Cys Gly
        505                 510                 515 aca gtt gtc tct atc ctg ggg gga gct cac ttt gga gag gga aat gga      1700
Thr Val Val Ser Ile Leu Gly Gly Ala His Phe Gly Glu Gly Asn Gly
                520                 525                 530 cag atc tgg gct gaa gaa ttc cag tgt gag gga cat gag tcc cat ctt      1748
Gln Ile Trp Ala Glu Glu Phe Gln Cys Glu Gly His Glu Ser His Leu
    535                 540                 545 tca ctc tgc cca gta gca ccc cgc cca gaa gga act tgt agc cac agc      1796
Ser Leu Cys Pro Val Ala Pro Arg Pro Glu Gly Thr Cys Ser His Ser
550                 555                 560                 565 agg gat gtt gga gta gtc tgc tca aga tac aca gaa att cgc ttg gtg      1844
Arg Asp Val Gly Val Val Cys Ser Arg Tyr Thr Glu Ile Arg Leu Val
                570                 575                 580 aat ggc aag acc ccg tgt gag ggc aga gtg gag ctc aaa acg ctt ggt      1892
Asn Gly Lys Thr Pro Cys Glu Gly Arg Val Glu Leu Lys Thr Leu Gly
        585                 590                 595 gcc tgg gga tcc ctc tgt aac tct cac tgg gac ata gaa gat gcc cat      1940
Ala Trp Gly Ser Leu Cys Asn Ser His Trp Asp Ile Glu Asp Ala His
                600                 605                 610 gtt ctt tgc cag cag ctt aaa tgt gga gtt gcc ctt tct acc cca gga      1988
Val Leu Cys Gln Gln Leu Lys Cys Gly Val Ala Leu Ser Thr Pro Gly
    615                 620                 625 gga gca cgt ttt gga aaa gga aat ggt cag atc tgg agg cat atg ttt      2036
Gly Ala Arg Phe Gly Lys Gly Asn Gly Gln Ile Trp Arg His Met Phe
630                 635                 640                 645 cac tgc act ggg act gag cag cac atg gga gat tgt cct gta act gct      2084
His Cys Thr Gly Thr Glu Gln His Met Gly Asp Cys Pro Val Thr Ala
                650                 655                 660 cta ggt gct tca tta tgt cct tca gag caa gtg gcc tct gta atc tgc      2132
Leu Gly Ala Ser Leu Cys Pro Ser Glu Gln Val Ala Ser Val Ile Cys
        665                 670                 675 tca gga aac cag tcc caa aca ctg tcc tcg tgc aat tca tcg tct ttg      2180
Ser Gly Asn Gln Ser Gln Thr Leu Ser Ser Cys Asn Ser Ser Ser Leu
                680                 685                 690 ggc cca aca agg cct acc att cca gaa gaa agt gct gtg gcc tgc ata      2228
Gly Pro Thr Arg Pro Thr Ile Pro Glu Glu Ser Ala Val Ala Cys Ile
    695                 700                 705 gag agt ggt caa ctt cgc ctg gta aat gga gga ggt cgc tgt gct ggg      2276
Glu Ser Gly Gln Leu Arg Leu Val Asn Gly Gly Gly Arg Cys Ala Gly
710                 715                 720                 725 aga gta gag atc tat cat gag ggc tcc tgg ggc acc atc tgt gat gac      2324
Arg Val Glu Ile Tyr His Glu Gly Ser Trp Gly Thr Ile Cys Asp Asp
                730                 735                 740 agc tgg gac ctg agt gat gcc cac gtg gtt tgc aga cag ctg ggc tgt      2372
Ser Trp Asp Leu Ser Asp Ala His Val Val Cys Arg Gln Leu Gly Cys
        745                 750                 755 gga gag gcc att aat gcc act ggt tct gct cat ttt ggg gaa gga aca      2420
Gly Glu Ala Ile Asn Ala Thr Gly Ser Ala His Phe Gly Glu Gly Thr
```

|  |  |
|---|---:|
| ggg ccc atc tgg ctg gat gag atg aaa tgc aat gga aaa gaa tcc cgc<br>Gly Pro Ile Trp Leu Asp Glu Met Lys Cys Asn Gly Lys Glu Ser Arg<br>775                        780                        785 | 2468 |
| att tgg cag tgc cat tca cac ggc tgg ggg cag caa aat tgc agg cac<br>Ile Trp Gln Cys His Ser His Gly Trp Gly Gln Gln Asn Cys Arg His<br>790                        795                        800                805 | 2516 |
| aag gag gat gcg gga gtt atc tgc tca gaa ttc atg tct ctg aga ctg<br>Lys Glu Asp Ala Gly Val Ile Cys Ser Glu Phe Met Ser Leu Arg Leu<br>                    810                        815                        820 | 2564 |
| acc agt gaa gcc agc aga gag gcc tgt gca ggg cgt ctg gaa gtt ttt<br>Thr Ser Glu Ala Ser Arg Glu Ala Cys Ala Gly Arg Leu Glu Val Phe<br>        825                        830                        835 | 2612 |
| tac aat gga gct tgg ggc act gtt ggc aag agt agc atg tct gaa acc<br>Tyr Asn Gly Ala Trp Gly Thr Val Gly Lys Ser Ser Met Ser Glu Thr<br>                840                        845                        850 | 2660 |
| act gtg ggt gtg gtg tgc agg cag ctg ggc tgt gca gac aaa ggg aaa<br>Thr Val Gly Val Val Cys Arg Gln Leu Gly Cys Ala Asp Lys Gly Lys<br>855                        860                        865 | 2708 |
| atc aac cct gca tct tta gac aag gcc atg tcc att ccc atg tgg gtg<br>Ile Asn Pro Ala Ser Leu Asp Lys Ala Met Ser Ile Pro Met Trp Val<br>870                        875                        880                885 | 2756 |
| gac aat gtt cag tgt cca aaa gga cct gac acg ctg tgg cag tgc cca<br>Asp Asn Val Gln Cys Pro Lys Gly Pro Asp Thr Leu Trp Gln Cys Pro<br>                    890                        895                        900 | 2804 |
| tca tct cca tgg gag aag aga ctg gcc agc ccc tcg gag gag acc tgg<br>Ser Ser Pro Trp Glu Lys Arg Leu Ala Ser Pro Ser Glu Glu Thr Trp<br>        905                        910                        915 | 2852 |
| atc aca tgt gac aac aag ata aga ctt cag gaa gga ccc act tcc tgt<br>Ile Thr Cys Asp Asn Lys Ile Arg Leu Gln Glu Gly Pro Thr Ser Cys<br>                920                        925                        930 | 2900 |
| tct gga cgt gtg gag atc tgg cat gga ggt tcc tgg ggg aca gtg tgt<br>Ser Gly Arg Val Glu Ile Trp His Gly Gly Ser Trp Gly Thr Val Cys<br>935                        940                        945 | 2948 |
| gat gac tct tgg gac ttg gac gat gct cag gtg gtg tgt caa caa ctt<br>Asp Asp Ser Trp Asp Leu Asp Asp Ala Gln Val Val Cys Gln Gln Leu<br>950                        955                        960                965 | 2996 |
| ggc tgt ggt cca gct ttg aaa gca ttc aaa gaa gca gag ttt ggt cag<br>Gly Cys Gly Pro Ala Leu Lys Ala Phe Lys Glu Ala Glu Phe Gly Gln<br>                    970                        975                        980 | 3044 |
| ggg act gga ccg ata tgg ctc aat gaa gtg aag tgc aaa ggg aat gag<br>Gly Thr Gly Pro Ile Trp Leu Asn Glu Val Lys Cys Lys Gly Asn Glu<br>                985                        990                        995 | 3092 |
| tct tcc ttg tgg gat tgt cct gcc aga cgc tgg ggc cat agt gag<br>Ser Ser Leu Trp Asp Cys Pro Ala Arg Arg Trp Gly His Ser Glu<br>        1000                      1005                    1010 | 3137 |
| tgt ggg cac aag gaa gac gct gca gtg aat tgc aca gat att tca<br>Cys Gly His Lys Glu Asp Ala Ala Val Asn Cys Thr Asp Ile Ser<br>        1015                      1020                    1025 | 3182 |
| gtg cag aaa acc cca caa aaa gcc aca aca ggt cgc tca tcc cgt<br>Val Gln Lys Thr Pro Gln Lys Ala Thr Thr Gly Arg Ser Ser Arg<br>        1030                      1035                    1040 | 3227 |
| cag tca tcc ttt att gca gtc ggg atc ctt ggg gtt gtt ctg ttg<br>Gln Ser Ser Phe Ile Ala Val Gly Ile Leu Gly Val Val Leu Leu<br>        1045                      1050                    1055 | 3272 |
| gcc att ttc gtc gca tta ttc ttc ttg act aaa aag cga aga cag<br>Ala Ile Phe Val Ala Leu Phe Phe Leu Thr Lys Lys Arg Arg Gln<br>        1060                      1065                    1070 | 3317 |
| aga cag cgg ctt gca gtt tcc tca aga gga gag aac tta gtc cac | 3362 |

```
Arg Gln Arg  Leu Ala Val Ser Ser  Arg Gly Glu Asn  Leu Val His
    1075             1080              1085 caa att caa  tac cgg gag atg aat  tct tgc ctg aat  gca gat gat        3407
Gln Ile Gln  Tyr Arg Glu Met Asn  Ser Cys Leu Asn  Ala Asp Asp
    1090             1095              1100 ctg gac cta  atg aat tcc tca gga  ggc cat tct gag  cca cac tga        3452
Leu Asp Leu  Met Asn Ser Ser Gly  Gly His Ser Glu  Pro His
    1105             1110              1115 aaaggaaaat gggaatttat aacccagtga gttcagcctt taagatacct tgatgaagac     3512
ctggactatt gaatggagca gaaattcacc tctctcactg actattacag ttgcattttt     3572
atggagttct tcttctccta ggattcctaa gactgctgct gaatttataa aaattaagtt     3632
tgtgaatgtg actacttagt ggtgtatatg agactttcaa gggaattaaa taaataaata    3692
agaatgttaa a                                                          3703

<210> SEQ ID NO 27
<211> LENGTH: 1116
<212> TYPE: PRT
<213> ORGANISM: Homo sapiens

<400> SEQUENCE: 27

Met Val Leu Leu Glu Asp Ser Gly Ser Ala Asp Phe Arg Arg His Phe
1               5                   10                  15

Val Asn Leu Ser Pro Phe Thr Ile Thr Val Val Leu Leu Leu Ser Ala
            20                  25                  30

Cys Phe Val Thr Ser Ser Leu Gly Gly Thr Asp Lys Glu Leu Arg Leu
        35                  40                  45

Val Asp Gly Glu Asn Lys Cys Ser Gly Arg Val Glu Val Lys Val Gln
    50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
            100                 105                 110

Val Ser Cys Arg Gly Asn Glu Ser Ala Leu Trp Asp Cys Lys His Asp
        115                 120                 125

Gly Trp Gly Lys His Ser Asn Cys Thr His Gln Gln Asp Ala Gly Val
    130                 135                 140

Thr Cys Ser Asp Gly Ser Asn Leu Glu Met Arg Leu Thr Arg Gly Gly
145                 150                 155                 160

Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
        195                 200                 205

Phe Gly Glu Gly Ser Gly Pro Ile Trp Phe Asp Leu Ile Cys Asn
    210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270
```

```
Arg Leu Glu Val Arg Phe Gln Gly Glu Trp Gly Thr Ile Cys Asp Asp
        275                 280                 285

Gly Trp Asp Ser Tyr Asp Ala Val Ala Cys Lys Gln Leu Gly Cys
    290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
                340                 345                 350

Asn Glu Asp Ala Gly Val Thr Cys Ser Asp Gly Ser Asp Leu Glu Leu
            355                 360                 365

Arg Leu Arg Gly Gly Gly Ser Arg Cys Ala Gly Thr Val Glu Val Glu
    370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
    435                 440                 445

Asn Trp Gln Trp Gly Gly Leu Thr Cys Asp His Tyr Glu Glu Ala Lys
    450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
                500                 505                 510

Glu Leu Gln Cys Gly Thr Val Val Ser Ile Leu Gly Gly Ala His Phe
    515                 520                 525

Gly Glu Gly Asn Gly Gln Ile Trp Ala Glu Glu Phe Gln Cys Glu Gly
    530                 535                 540

His Glu Ser His Leu Ser Leu Cys Pro Val Ala Pro Arg Pro Glu Gly
545                 550                 555                 560

Thr Cys Ser His Ser Arg Asp Val Gly Val Val Cys Ser Arg Tyr Thr
                565                 570                 575

Glu Ile Arg Leu Val Asn Gly Lys Thr Pro Cys Glu Gly Arg Val Glu
                580                 585                 590

Leu Lys Thr Leu Gly Ala Trp Gly Ser Leu Cys Asn Ser His Trp Asp
    595                 600                 605

Ile Glu Asp Ala His Val Leu Cys Gln Gln Leu Lys Cys Gly Val Ala
    610                 615                 620

Leu Ser Thr Pro Gly Gly Ala Arg Phe Gly Lys Gly Asn Gly Gln Ile
625                 630                 635                 640

Trp Arg His Met Phe His Cys Thr Gly Thr Glu Gln His Met Gly Asp
                645                 650                 655

Cys Pro Val Thr Ala Leu Gly Ala Ser Leu Cys Pro Ser Glu Gln Val
            660                 665                 670

Ala Ser Val Ile Cys Ser Gly Asn Gln Ser Gln Thr Leu Ser Ser Cys
            675                 680                 685
```

```
Asn Ser Ser Ser Leu Gly Pro Thr Arg Pro Thr Ile Pro Glu Glu Ser
690                 695                 700

Ala Val Ala Cys Ile Glu Ser Gly Gln Leu Arg Leu Val Asn Gly Gly
705                 710                 715                 720

Gly Arg Cys Ala Gly Arg Val Glu Ile Tyr His Glu Gly Ser Trp Gly
                725                 730                 735

Thr Ile Cys Asp Asp Ser Trp Asp Leu Ser Asp Ala His Val Val Cys
            740                 745                 750

Arg Gln Leu Gly Cys Gly Glu Ala Ile Asn Ala Thr Gly Ser Ala His
        755                 760                 765

Phe Gly Glu Gly Thr Gly Pro Ile Trp Leu Asp Glu Met Lys Cys Asn
770                 775                 780

Gly Lys Glu Ser Arg Ile Trp Gln Cys His Ser His Gly Trp Gly Gln
785                 790                 795                 800

Gln Asn Cys Arg His Lys Glu Asp Ala Gly Val Ile Cys Ser Glu Phe
                805                 810                 815

Met Ser Leu Arg Leu Thr Ser Glu Ala Ser Arg Glu Ala Cys Ala Gly
            820                 825                 830

Arg Leu Glu Val Phe Tyr Asn Gly Ala Trp Gly Thr Val Gly Lys Ser
        835                 840                 845

Ser Met Ser Glu Thr Thr Val Gly Val Val Cys Arg Gln Leu Gly Cys
850                 855                 860

Ala Asp Lys Gly Lys Ile Asn Pro Ala Ser Leu Asp Lys Ala Met Ser
865                 870                 875                 880

Ile Pro Met Trp Val Asp Asn Val Gln Cys Pro Lys Gly Pro Asp Thr
                885                 890                 895

Leu Trp Gln Cys Pro Ser Ser Pro Trp Glu Lys Arg Leu Ala Ser Pro
            900                 905                 910

Ser Glu Glu Thr Trp Ile Thr Cys Asp Asn Lys Ile Arg Leu Gln Glu
        915                 920                 925

Gly Pro Thr Ser Cys Ser Gly Arg Val Glu Ile Trp His Gly Gly Ser
930                 935                 940

Trp Gly Thr Val Cys Asp Asp Ser Trp Asp Leu Asp Asp Ala Gln Val
945                 950                 955                 960

Val Cys Gln Gln Leu Gly Cys Gly Pro Ala Leu Lys Ala Phe Lys Glu
                965                 970                 975

Ala Glu Phe Gly Gln Gly Thr Gly Pro Ile Trp Leu Asn Glu Val Lys
            980                 985                 990

Cys Lys Gly Asn Glu Ser Ser Leu  Trp Asp Cys Pro Ala Arg Arg Trp
        995                 1000                1005

Gly His  Ser Glu Cys Gly His  Lys Glu Asp Ala Ala  Val Asn Cys
        1010                1015                1020

Thr Asp  Ile Ser Val Gln Lys  Thr Pro Gln Lys Ala  Thr Thr Gly
        1025                1030                1035

Arg Ser  Ser Arg Gln Ser Ser  Phe Ile Ala Val Gly  Ile Leu Gly
        1040                1045                1050

Val Val  Leu Leu Ala Ile Phe  Val Ala Leu Phe Phe  Leu Thr Lys
        1055                1060                1065

Lys Arg  Arg Gln Arg Gln Arg  Leu Ala Val Ser Ser  Arg Gly Glu
        1070                1075                1080

Asn Leu  Val His Gln Ile Gln  Tyr Arg Glu Met Asn  Ser Cys Leu
        1085                1090                1095
```

```
Asn Ala Asp Asp Leu Asp Leu  Met Asn Ser Ser Gly  Gly His Ser
    1100                1105               1110

Glu Pro His
    1115
```

CD163-BINDING CONJUGATES

The present invention relates to haptoglobin-haemoglobin (Hp-Hb) complex or a part thereof or a mimic thereof being operably linked to a substance and capable of binding a CD163 receptor. Furthermore, the invention relates to a CD163 variant, membrane bound or soluble, capable of binding at least one haptoglobin-haemoglobin (Hp-Hb) complex, and the use of the Hp-Hb complex and the CD163 receptor for therapy.

BACKGROUND OF THE INVENTION

Normal adult haemoglobin consists of a tetramer of four haemoglobin chains, two α-chains and two β-chains. $O_2$ binds to the tetrameric form of haemoglobin and is transported in the blood. Fetal blood comprises fetal haemoglobin, a tetramer consisting of two α-chains and two γ-chains. Further haemoglobin chains have been identified, such as δ-chains, ε-chains, zeta-chains, τ-chains or the S form known to be the mutation seen in haemoglobin of individuals suffering from sickle cell disease.

Intravascular lysis of red blood cells (haemolysis) leads to the release of haemoglobin into plasma. This phenomenon occurs during physiological as well as pathological conditions. Pathological complications are severe when accelerated in infectious e.g. malaria), inherited (e.g. side cell anemia), or autoimmune diseases. The haemoglobin tetramers are converted to haemoglobin dimers capable of binding haptoglobin. In the plasma haemoglobin is captured by the acute phase protein haptoglobin. Haptoglobin is a blood plasma protein having a molecular weight of approximately 86,000 to 400,000 and plays an important role in the metabolism of haemoglobin liberated into the blood stream. When liberated excessively in the blood the haemoglobin is excreted into the urine through the renal tubules, resulting in not only an iron loss but also disorders of the renal tubules. Because haptoglobin binds selectively and firmly to haemoglobin in vivo and thereby forms a haemoglobin-haptoglobin complex, it has important functions in the recovery of iron and in the prevention of renal disorders.

Hp is synthesised as a single chain, which is post-translationally cleaved into an amino-terminal α chain and a carboxy-terminal β chain. The basic structure of Hp, as found in most mammals, is a homodimer (FIG. 2a), in which the two Hp molecules are linked by a single disulfide bond via their respective ~9 kDa α chains. In man, a variant with a long α chain is also present in all populations. This variant arose apparently by an early intragenic duplication, presumably originating from an unequal crossover of two basic alleles, resulting in an Hp with an α chain of ~14 kDa. The short and long α chains are designated as $\alpha^1$ and $\alpha^2$ respectively. Since the cysteine forming the intermolecular disulfide bond between the α chains is also duplicated, humans carrying the long variant allele exhibit a multimeric Hp phenotype (FIG. 2a).

Conventional human haptoglobins have been well studied; they were discovered over 40 years ago and their role is thought to be in the plasma transport of free haemoglobin. Additionally, haptoglobin is believed to have anti-inflammatory activities, such as its decreasing effect on neutrophil metabolism, and an effect on the immune system by possibly modulating B cell proliferation and decrease antibody production. The mechanisms of the influence of haptoglobin on immune function is unknown. The potential signalling pathways by which haptoglobin is mediating its effects, and the existence of a haptoglobin receptor have not been disclosed in the prior art.

However, Ghmati et al., 1996 describe a study in which haptoglobin is an alternative low-affinity ligand for CD11b/CD18 on monocyte cell lines. CD11b/CD18 is part of the integrin family and is involved in inflammatory and immunological functions.

Yet another receptor molecule present on monocytes is CD163. It is identified as a member of the scavenger receptor cystein-rich superfamily (SRCR) present on cells of the monocytic family, such as most macrophages. Ritter et al., 1999 discuss the regulation, promoter structure and genomic organisation of the CD163 receptor. The precise function of CD163 is not disclosed. Furthermore, previous work on the biological function of CD163 is limited to a study on the effect of antibody-mediated crosslinking of CD163 on cultured monocytes (Van den Heuvel, M. M. et al. Regulation of CD163 on human macrophages: cross-linking of CD163 induces signalling and activation. J. Leukoc.Bil. 66, 858-866 (1999). The CD163 surface ligation induces a tyrosine kinase dependent signal resulting in intracellular calcium mobilisation, inositol triphosphate production, and increased secretion of anti-inflammatory cytokines.

SUMMARY

The present inventors have identified CD163 as the high-affinity macrophage receptor for haptoglobin-haemoglobin complexes. They also have identified a soluble form of CD163 in plasma of normal human subjects and found a correlation between membrane bound and soluble receptor. Under normal conditions approx. 100-500 μg/l soluble CD163 is present in plasma. The present invention relates to the use of the CD163 receptor, membrane bound or soluble and/or a CD163 variant, and/or the use of haptoglobin-haemoglobin complexes in the diagnosis, prevention and/or treatment of various diseases and disorders.

Accordingly, the invention describes a Hp-Hb complex, or a part thereof or a mimic thereof being operably linked to a substance, wherein the Hp-Hb complex is capable of binding CD163 and/or a CD163 variant. In the present context the term Hp-Hb complex includes a functional equivalent thereof unless expressively otherwise stated.

In the present context the term "substance" means a component heterologous to the Hp-Hb complex, such as a drug, a gene, a vesicle, a vector, or the like.

Further, the invention concerns the use of at least one Hp-Hb complex for the delivery of at least one drug, or at least one gene to a cell expressing a CD163 receptor and/or a CD163 receptor variant. The invention also relates to the use of at least one Hp-Hb complex, further comprising a CD163 receptor variant for the identification of at least one Hp-Hb complex in serum and/or plasma of an individual.

In the present context the term CD163 receptor covers both the conventional scavenger receptor CD163 of monocytes and most tissue macrophages as well as the soluble form of CD163, sHbSR unless otherwise specified. The term CD163 is used synonymously with the term CD163 receptor. The term sHbSR is used interchangeably with soluble CD163 receptor.

The term a CD163 receptor variant is used synonymously with the term CD163 variant.

In another aspect, the present invention relates to a CD163 variant capable of binding at least one haptoglobin-haemoglobin (Hp-Hb) complex.

In a further aspect of the invention the use of at least one CD163 variant in the manufacture of a medicament for treatment of disorders/complications related to haemolysis in an individual in need of such treatment is disclosed.

Also, the invention describes the use of at least one CD163 variant for the removal of at least one Hp-Hb complex in serum and/or plasma of an individual, and the use for the determination of the haemolysis rate of an individual. Further, the use of at least one complex comprising haemoglobin and haptoglobin as a marker for a cell expressing a CD163 variant, wherein at least one of the haemoglobin or haptoglobin molecules are labelled is also described in the present invention.

An object of the invention is to provide a CD163 molecule for the use as a medicament. The areas of use of a CD163 molecule according to the invention are identical to the areas of use described above for the CD163 variant.

Further, a Hp-Hb complex, or a part thereof or a mimic thereof being operably linked to a substance, wherein the Hp-Hb complex is capable of binding said CD163 molecule is also within the scope of the invention.

In the present context the word medicament is used in its normal meaning as a composition to be administered to an individual for prophylactic, therapeutic and/or diagnostic purposes.

FIGURES

FIG. 1: is an illustration of the steps involved in the Hp-Hb/CD163 binding.

Figure 2:
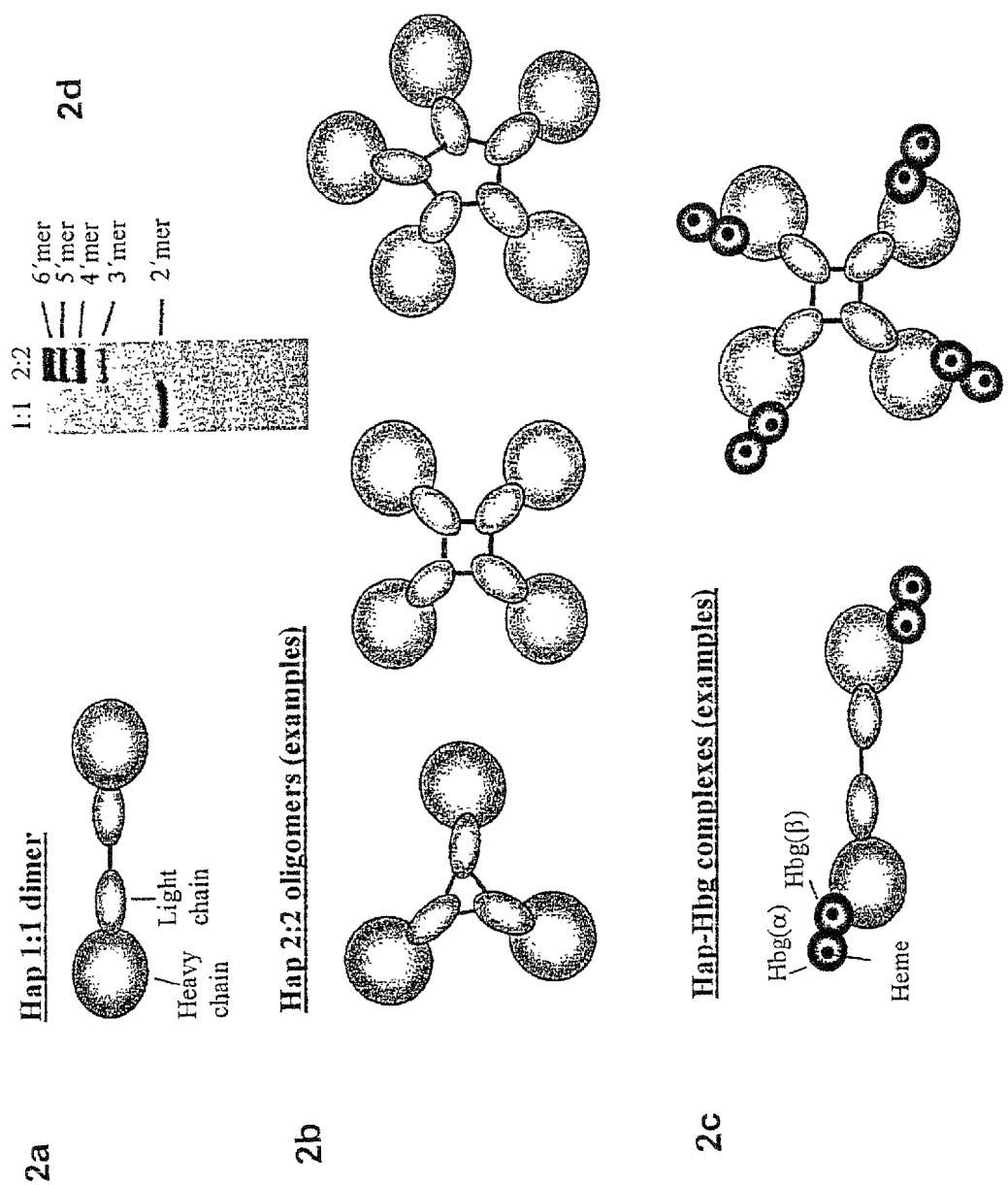

FIG. 2: shows examples of 2a) a haptoglobin dimer, 2b) haptoglobin multimers, 2c) Hp-Hb complexes, and 2d) a SDS-PAGE gel of mono- and multimers of haptoglobin.

Figure 3:
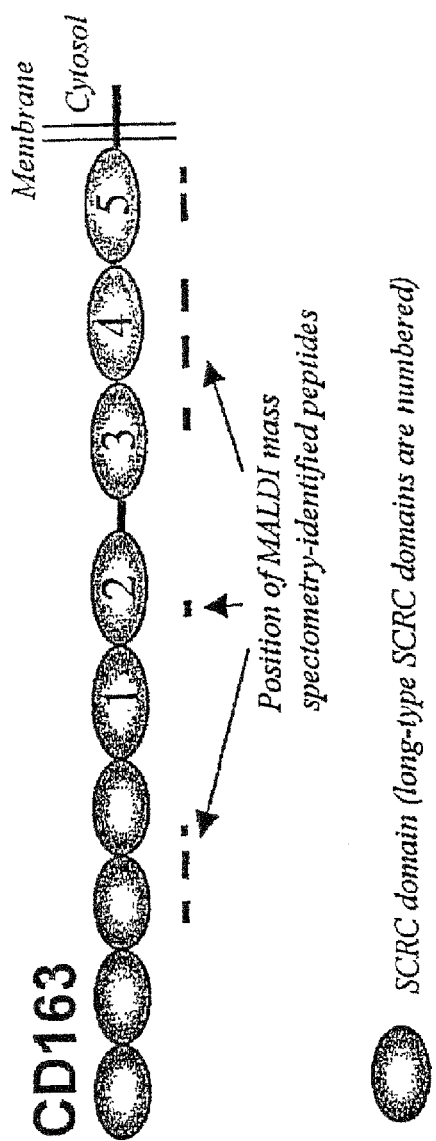

FIG. 3: shows a CD163 molecule.

FIG. 4: shows 9 different haptoglobin sequences (SEQ ID NOs:1-9)

FIG. 5: shows 4 different CD163 sequences (SEQ ID NOs:10-13)

FIG. 6: Binding of Hp-Hb to CD163. a, Illustration of the subunit organisation and disulfide bridging of the various Hp and Hp-Hb complexes. The inset shows non-reducing SDS-PAGE of the Hp(1-1) dimer and Hp(2-2) multimers. b, Surface plasmon resonance analysis of the binding of Hp-Hb to CD163. The measurements were carried out at Hb concentrations ranging from zero to 100 μg/ml in the absence of Hp (left panel), or in the presence of 50 μg/ml of Hp(1-1) (middle panel), and 50 μg/ml Hp(2-2) (right panel). No binding was observed with either Hb or Hp alone, and saturation of the binding was obtained at 50 μg/ml Hb for both Hp phenotypes. c, Inhibition of CD163-binding of $^{125}$I-labelled Hp(1-1)-Hb (left panels) and Hp(2-2)-Hb (right panels) by polyclonal anti-CD163 IgG, non-immune rabbit IgG, EDTA (5 mM) and by various concentrations of unlabelled Hp(1-1)-Hb and Hp(2-2)-Hb complexes. CD163 was immobilised in microtiter plate wells.

FIG. 7: CD163-mediated endocytosis of $^{125}$I-Hp-Hb. a, Cell-association and degradation of $^{125}$I-Hp(2-2)-Hb in mock-transfected (left panel) and CD163 cDNA-transfected CHO cells (middle panel). Addition of the lysosomal inhibitors chloroquine and leupeptin (both 100 μM) inhibited degradation leading to cellular accumulation of radioactivity (right panel). b, Inhibition of $^{125}$I-Hp-Hb uptake in CD163 cDNA-transfected CHO cells (left panel) and in CD163-expressing histiocytic lymphoma-derived SU-DHL-1 cells (right panel). Both cell types displayed a saturable uptake inhibited by anti-CD163 polyclonal IgG. The insets in a and b show anti-CD163 immunoblotting of the cells.

Figure 8:
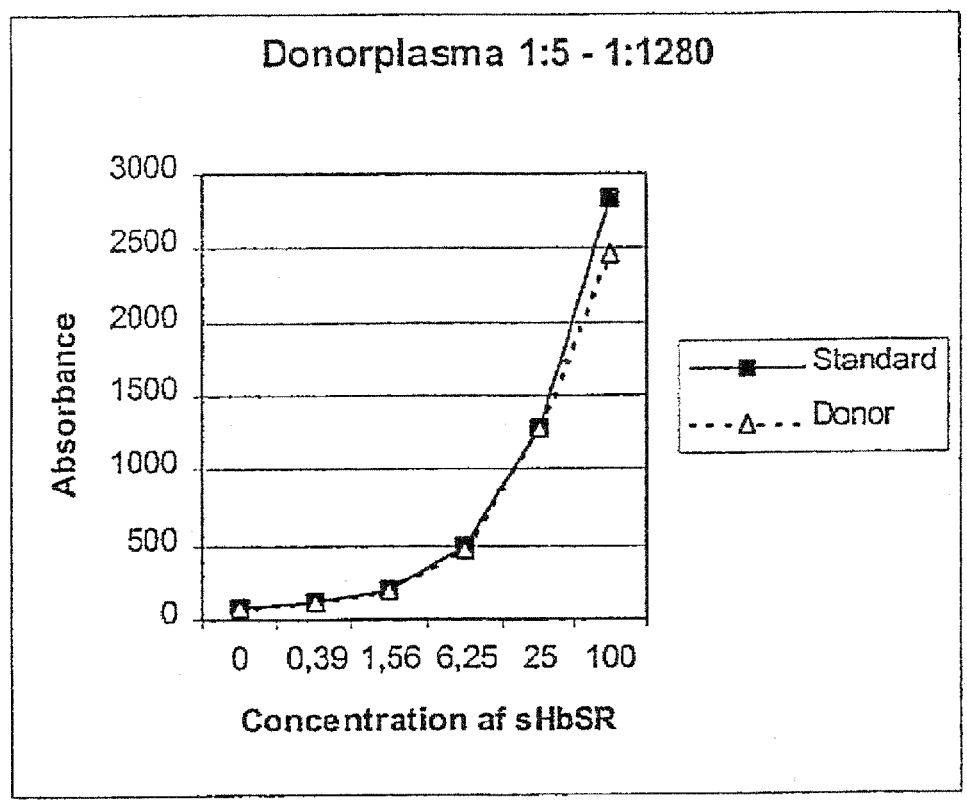

FIG. 8: Determination of the concentration of sCD163 in the blood of a human donor.

FIG. 9: Fluorescence studied in confocal microscope (example 6).

Figure 10:
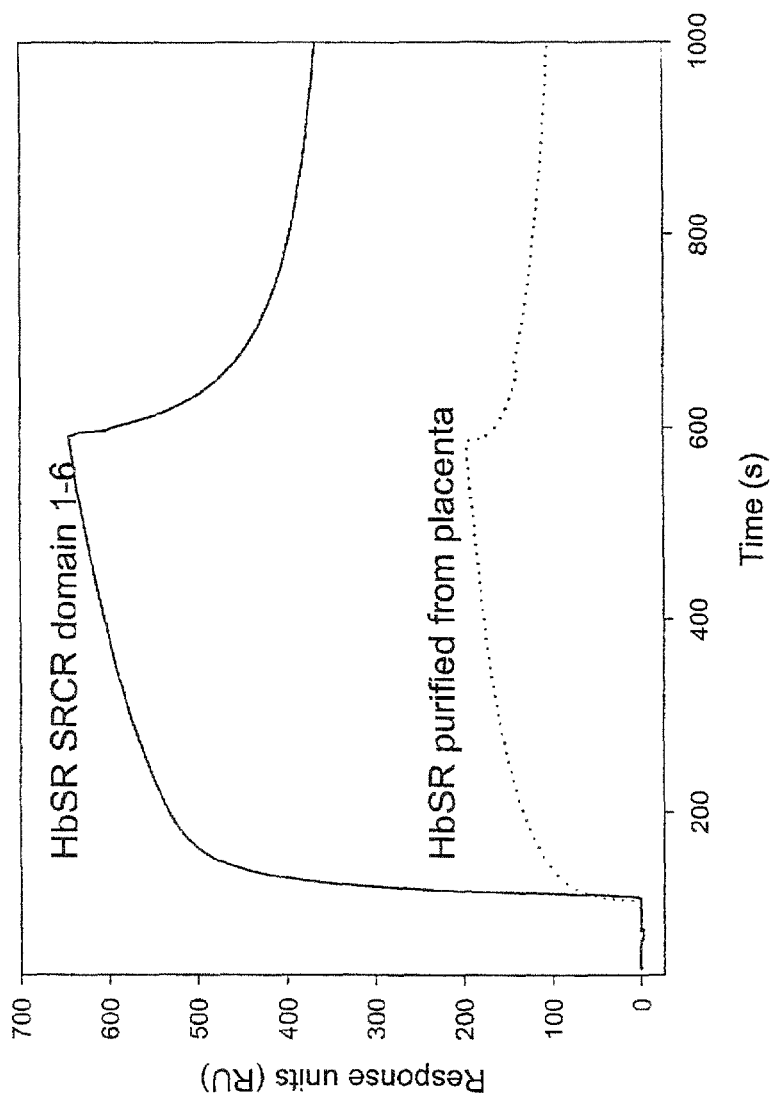

FIG. 10: Sensogram of the destiny of HbSR and HbSR SRCR domain 1-6.

Figure 11:
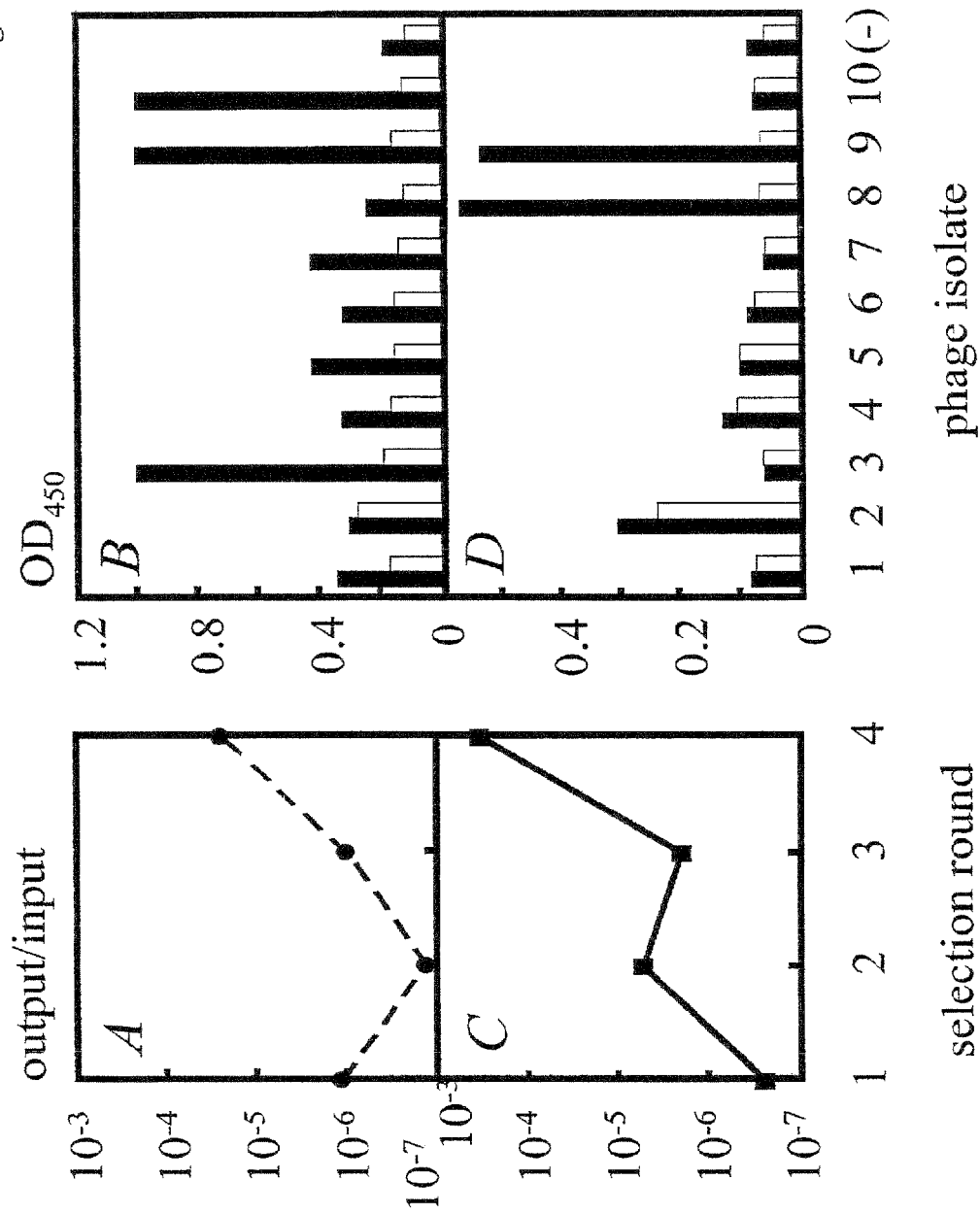

FIG. 11: Selection of Fab antibody phage to Hp-Hb complexes and CD163. The output over input ratio, indicative of selection of clones, is depicted in panels A and C for the selections on coated Hp-Hb complexes and CD163, respectively. In the panels B and D, two representative phage ELISAs are shown in which 10 random clones from the third round of selection have been tested. Clones 3, 9 and 10 in panel B represent the Fab1 clone isolated from the Hp-Hb complex-selections and clones 8 and 9 in panel D represent the Fab18 clone isolated from the CD163 selections. In total, 50 clones from each round were screened.

Figure 12A:
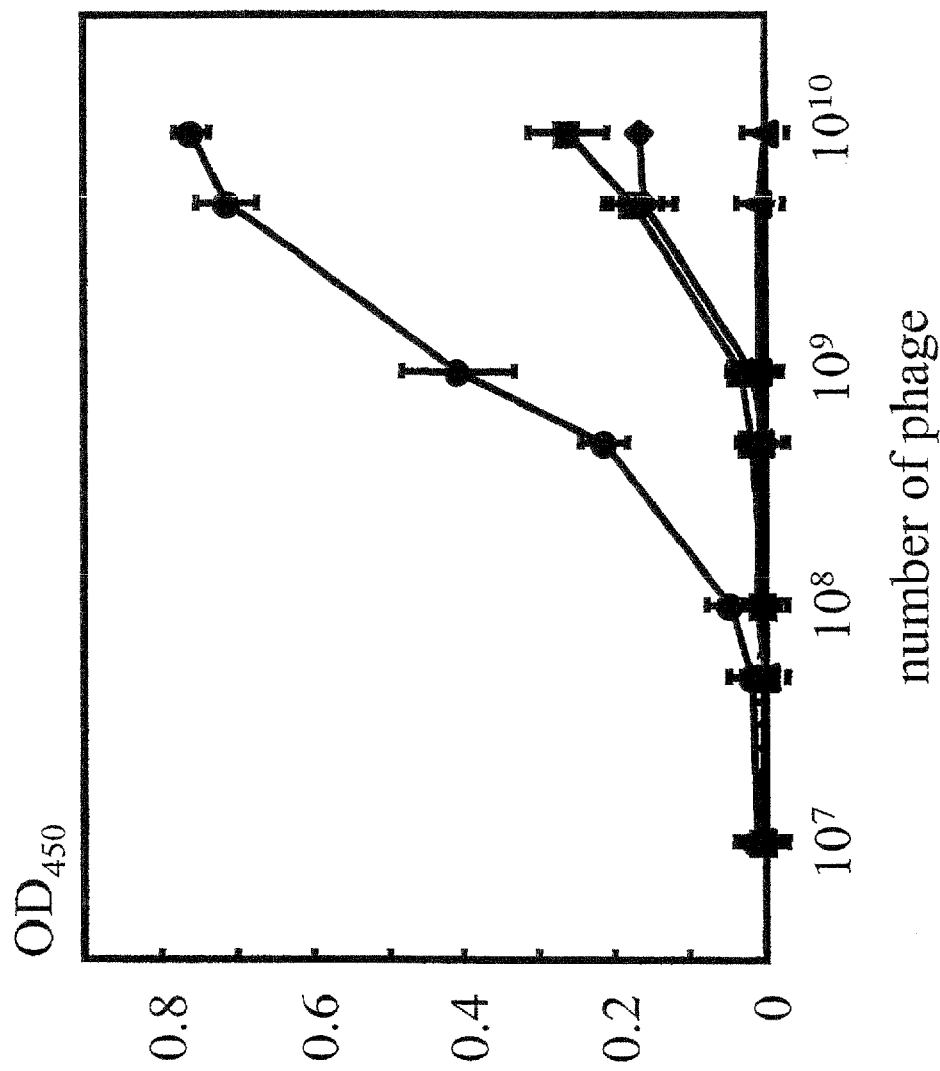

FIG. 12a: Binding of anti-Hp-Hb Fab1-phage to Hp-Hb complexes, Hp and Hb. The binding to Hp-Hb complexes is represented by the circles, to Hp by the squares, to Hb by the diamonds and to BSA by the triangles. The experiment was performed in duplicate. An irrelevant Fab phage did not show binding to any of the tested antigens under these conditions (not shown).

Figure 12B:
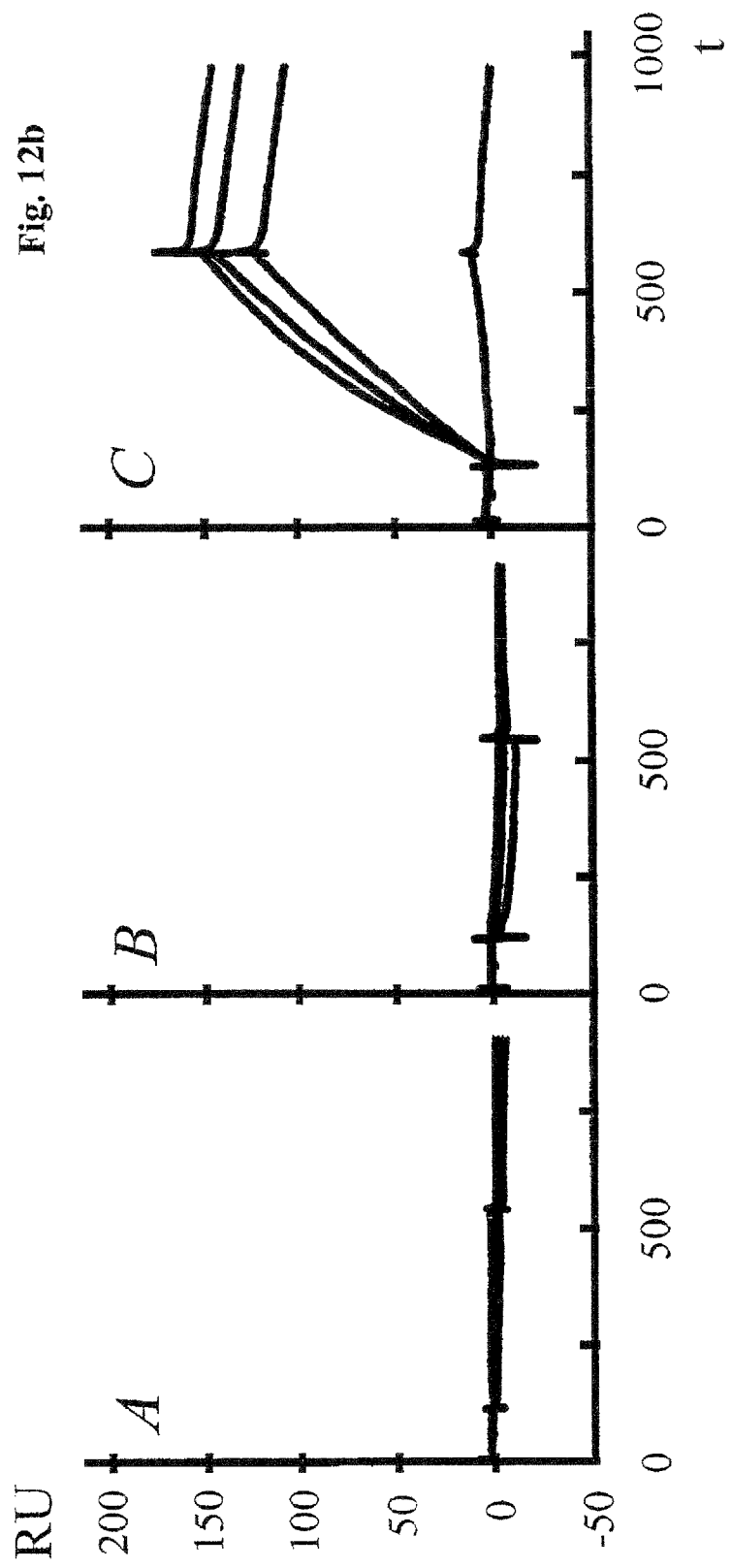

FIG. 12b: Binding of Fab1 to Hp-Hb complexes, Hp and Hb immobilized on a BIAcore® sensor-chip. Binding to Fab1 to Hb is depicted in panel A, to Hp in panel B and to Hp-Hb complexes in panel C. In each case a concentration range of 0 to 200 nM Fab1 was used.

FIG. 13: Fab inhibition of $^{125}$I-Hp-Hb (2:2) complex-binding to coated CD163. Curves represent the effects of increasing concentrations of anti-Hp-Hb Fab1 (diamonds), anti-CD163 Fab18 (squares) and irrelevant FabA8 (triangles) on binding of a trace amount of $^{125}$I-Hp-Hb complexes to CD163.

DETAILED DESCRIPTION OF THE INVENTION

In a first aspect the present invention relates to a Hp-Hb complex or a functional equivalent thereof being operably linked to a substance, said complex and/or functional equivalent thereof being capable of binding to a CD163 receptor and/or a CD163 variant. A functional equivalent of a Hp-Hb complex is to be understood as any part (or fragment) or any mimic capable of binding to a CD163 receptor.

"Functional equivalency" as used in the present invention is according to one preferred embodiment established by means of reference to the corresponding functionality of a predetermined Hp-Hb fragment.

In the present context the term "Hp-Hb complex" means a complex of at least one haptoglobin chain and at least one haemoglobin chain called a monomeric Hp-Hb complex. Preferably the complex comprises at least one haptoglobin chain and at least one dimeric form of haemoglobin chains. In a further preferred embodiment the complex comprises a multimeric form of haptoglobin chains such as a dimeric form, each haptoglobin chain binding at least one haemoglobin chain, preferably a dimer of haemoglobin chains.

The fragment thereof should be understood to be any part of the Hp-Hb complex capable of binding to the CD163 receptor or to a variant thereof and through said binding activate uptake of the fragment and/or the substance into the CD163 presenting cell.

The mimic thereof should be understood to be any modification of the Hp-Hb complex (in the present context also called a variant of the complex) or any other molecule capable of binding to the CD163 receptor or to a variant thereof and through said binding activating uptake of the fragment and/or the substance into the CD163 presenting cell. Mimics may be peptides, peptide derivatives, antibodies, as well as non-peptide compounds, such as small organic compounds, sugars and fats.

In a preferred embodiment mimics may be antibodies capable of binding to the CD163 receptor, for example in order to elicit uptake of a substance linked to the antibody.

Fragments and/or mimics may be identified by combinatorial chemistry using the CD163 receptor, phase display technique or other techniques known to the person skilled in the art.

The Hp-Hb complex fragment or mimic is preferably, capable of binding to a region in the SRCR domains I-IX of the CD163 receptor, such as capable of binding to a region in the SRCR domains I-VIII of the CD163 receptor, capable of binding to a region in the SRCR domains I-VII of the CD163 receptor, capable of binding to a region in the SRCR domains I-VI of the CD163 receptor, capable of binding to a region in the SRCR domains I-V of the CD163 receptor, capable of binding to a region in the SRCR domains I-IV of the CD163 receptor, capable of binding to a region in the SRCR domains I-III of the CD163 receptor, capable of binding to a region in the SRCR domains I-II of the CD163 receptor, or a variant thereof.

It is preferred that the Hp-Hb complex or a part thereof or a mimic thereof is available in a purified and/or isolated form.

According to the invention the term "Hp-Hb complex" is meant to include functional equivalents of the Hp-Hb complex comprising a predetermined amino acid sequence. In the present context the term "predetermined amino acid sequence of Hp-Hb complex" relates to both the haptoglobin sequence and the haemoglobin sequence.

The predetermined sequence of a haptoglobin chain may be any of the sequences shown in FIGS. 4a and 4b, i.e. any of the sequences having the sequence identification in the sequence database SWISS-PROT (sp) or trEMBL (tr).

| | |
|---|---|
| sp\|P00737\|HPT1_HUMAN | (SEQ ID NO: 1) |
| sp\|P00738\|HPT2_HUMAN | (SEQ ID NO: 2) |
| sp\|P50417\|HPT_ATEGE | (SEQ ID NO: 3) |
| tr\|Q60574\|Q60574 | (SEQ ID NO: 4) |
| tr\|Q61646\|Q61646 | (SEQ ID NO: 5) |
| sp\|Q62558\|HPT_MUSSA | (SEQ ID NO: 6) |
| sp\|P06866\|HPT_RAT | (SEQ ID NO: 7) |
| tr\|O35086\|O35086 | (SEQ ID NO: 8) |
| sp\|P19006\|HPT_CANFA | (SEQ ID NO: 9) |

A predetermined amino acid sequence for a heamoglobin chain may be any of the sequences mentioned below together with accession No. in the sequence database SWISSPROT:

sp|P01922|HBA_HUMAN HEMOGLOBIN ALPHA CHAIN—*Homo sapiens* (Human), *Pan troglodytes* (Chimpanzee), and *Pan paniscus* (Pygmy chimpanzee) (Bonobo).

(SEQ ID NO: 14)
VLSPADKTNVKAAWGKVGAHAGEYGAEALERMFLSFPTTKTYFPHFDLSH

GSAQVKGHGKKVADALTNAVAHVDDMPNALSALSDLHAHKLRVDPVNFKL

LSHCLLVTLAAHLPAEFTPAVHASLDKFLASVSTVLTSKYR sp|P02023|HBB_HUMAN HEMOGLOBIN BETA CHAIN—*Homo sapiens* (Human), *Pan troglodytes* (Chimpanzee), and *Pan paniscus* (Pygmy chimpanzee) (Bonobo).

(SEQ ID NO: 14)
VHLTPEEKSAVTALWGKVNVDEVGGEALGRLLVVYPWTQRFFESFGDLST

PDAVMGNPKVKAHGKKVLGAFSDGLAHLDNLKGTFATLSELHCDKLHVDP

ENFRLLGNVLVCVLAHHFGKEFTPPVQAAYQKVVAGVANALAHKYH sp|P02042|HBD_HUMAN HEMOGLOBIN DELTA CHAIN—*Homo sapiens* (Human).

(SEQ ID NO: 16)
VHLTPEEKTAVNALWGKVNVDAVGGEALGRLLVVYPWTQRFFESFGDLSS

PDAVMGNPKVKAHGKKVLGAFSDGLAHLDNLKGTFSQLSELHCDKLHVDP

ENFRLLGNVLVCVLARNFGKEFTPQMQAAYQKVVAGVANALAHKYH sp-P02096|HBG_HUMAN HEMOGLOBIN GAMMA-A AND GAMMA-G CHAINS—*Homo sapiens* (Human), and *Pan troglodytes* (Chimpanzee).

(SEQ ID NO: 17)
GHFTEEDKATITSLWGKVNVEDAGGETLGRLLVVYPWTQRFFDSFGNLSS

ASAIMGNPKVKAHGKKVLTSLGDAIKHLDDLKGTFAQLSELHCDKLHVDP

ENFKLLGNVLVTVLAIHFGKEFTPEVQASWQKMVTAVASALSSRYH sp|P09105|HBAT_HUMAN HEMOGLOBIN THETA-1 CHAIN—*Homo sapiens* (Human).

(SEQ ID NO: 18)
ALSAEDRALVRALWKKLGSNVGVYTTEALERTFLAFPATKTYFSHLDLSP

GSSQVRAHGQKVADALSLAVERLDDLPHALSALSHLACQLRVDPASFQL

LGHCLLVTLARHYPGDFSPALQASLDKFLSHVISALVSEYR sp|P02008|HBAZ_HUMAN HEMOGLOBIN ZETA CHAIN—*Homo sapiens* (Human).

(SEQ ID NO: 19)
SLTKTERTIIVSMWAKISTQADTIGTETLERLFLSHPQTKTYFPHFDLHP

GSAQLRAHGSKVVAAVGDAVKSIDDIGGALSKLSELHAYILRVDPVNFKL

LSHCLLVTLAARFPADFTAEAHAAWDKFLSVVSSVLTEKYR sp|P02100|HBE_HUMAN HEMOGLOBIN EPSILON CHAIN—*Homo sapiens* (Human).

(SEQ ID NO: 20)
VHFTAEEKAAVTSLWSKMNVEEAGGEALGRLLVVYPWTQRFFDSFGNLSS

PSAILGNPKVKAHGKKVLTSFGDAIKNMDNLKPAFAKLSELHCDKLHVDP

ENFKLLGNVMVIILATHFGKEFTPEVQAAWQKLVSAVAIALAHKYH tr|Q14510|Q14510 SICKLE BETA-HEMOGLOBIN MRNA—*Homo sapiens* (Human).

(SEQ ID NO: 21)
MVHLTPVEKSAVTAXWGKVNVDEVGGEALGRLLVVYPWTQRFFESFGDLS

TPDAVMGNPKVKAHGKKVLGAFSDGLAHLDNLKGTFATLSELHCDKLHVD

PENFRLLGNVLVCVLAHHFGKEFTPPVQAAYQKVVAGVANALAHKYH

A "functional equivalent" is defined as:

i) equivalents comprising an amino acid sequence capable of being recognised by an antibody also capable of recognising the predetermined amino acid sequence, and/or ii) equivalents comprising an amino acid sequence capable of binding to a receptor moiety also capable of binding the predetermined amino acid sequence, and/or iii) equivalents having at least a substantially similar or higher binding affinity to CD163 as at least a monomeric Hp-Hb complex comprising said predetermined amino acid sequence.

According to the present invention a functional equivalent of a Hp-Hb complex or fragments thereof may be obtained by addition, substitution or deletion of at least one amino acid in either or both of the haptoglobin sequence and the haemoglobin sequence. Thus, a functional equivalent of the Hp-Hb complex may comprise a modification of either of the components of the complex or both.

When the amino acid sequence comprises a substitution of one amino acid for another, such a substitution may be a conservative amino acid substitution. Fragments of the complex according to the present invention may comprise more than one such substitution, such as e.g. two conservative amino acid substitutions, for example three or four conservative amino acid substitutions, such as five or six conservative amino acid substitutions, for example seven or eight conservative amino acid substitutions, such as from 10 to 15 conservative amino acid substitutions, for example from 15 to 25 conservative amino acid substitution. Substitutions can be made within any one or more groups of predetermined amino acids.

Examples of equivalents comprising one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids.

Accordingly, mimics of the complex, or fragments thereof according to the invention may comprise, within the same mimic, or fragments thereof or among different mimics, or fragments thereof, at least one substitution, such as a plurality of substitutions introduced independently of one another. Mimics of the complex, or fragments thereof may thus comprise conservative substitutions independently of one another, wherein at least one glycine (Gly) of said mimic, or fragments thereof is substituted with an amino acid selected from the group of amino acids consisting of Ala, Val, Leu, and Ile, and independently thereof, mimics, or fragments thereof, wherein at least one of said alanines (Ala) of said mimics, or fragments thereof is substituted with an amino acid selected from the group of amino acids consisting of Gly, Val, Leu, and Ile, and independently thereof, mimics, or fragments thereof, wherein at least one valine (Val) of said mimic, or fragments thereof is substituted with an amino acid selected from the group of amino acids consisting of Gly, Ala, Leu, and Ile, and independently thereof, mimics, or fragments thereof, wherein at least one of said leucines (Leu) of said mimic, or fragments thereof is substituted with an amino acid selected from the group of amino acids consisting of Gly, Ala, Val, and Ile, and independently thereof, mimics, or fragments thereof, wherein at least one isoleucine (Ile) of said mimics, or fragments thereof is substituted with an amino acid selected from the group of amino acids consisting of Gly, Ala, Val and Leu, and independently thereof, mimics, or fragments thereof wherein at least one of said aspartic acids (Asp) of said mimic, or fragments thereof is substituted with an amino acid selected from the group of amino acids consisting of Glu, Asn, and Gln, and independently thereof, mimics, or fragments thereof, wherein at least one of said phenylalanines (Phe) of said mimics, or fragments thereof is substituted with an amino acid selected from the group of amino acids consisting of Tyr, Trp, His, Pro, and preferably selected from the group of amino acids consisting of Tyr and Trp, and independently thereof, mimics, or fragments thereof, wherein at least one of said tyrosines (Tyr) of said mimics, or fragments thereof is substituted with an amino acid selected from the group of amino acids consisting of Phe, Trp, His, Pro, preferably an amino acid selected from the group of amino acids consisting of Phe and Trp, and independently thereof, mimics, or fragments thereof, wherein at least one of said arginines (Arg) of said fragment is substituted with an amino acid selected from the group of amino acids consisting of Lys and His, and independently thereof, mimics, or fragments thereof, wherein at least one lysine (Lys) of said mimics, or fragments thereof is substituted with an amino acid selected from the group of amino acids consisting of Arg and His, and independently thereof, mimics, or fragments thereof, wherein at least one of said aspargines (Asn) of said mimics, or fragments thereof is substituted with an amino acid selected from the group of amino acids consisting of Asp, Glu, and Gln, and independently thereof, mimics, or fragments thereof, wherein at least one glutamine (Gln) of said mimics, or fragments thereof is substituted with an amino acid selected from the group of amino acids consisting of Asp, Glu, and Asn, and independently thereof, mimics, or fragments thereof, wherein at least one proline (Pro) of said mimics, or fragments thereof is substituted with an amino acid selected from the group of amino acids consisting of Phe, Tyr, Trp, and His, and independently thereof, mimics, or fragments thereof, wherein at least one of said cysteines (Cys) of said mimics, or fragments thereof is substituted with an amino acid selected from the group of amino acids consisting of Asp, Glu, Lys, Arg, His, Asn, Gln, Ser, Thr, and Tyr.

It is clear from the above outline that the same equivalent or fragment thereof may comprise more than one conservative amino acid substitution from more than one group of conservative amino acids as defined herein above.

Conservative substitutions may be introduced in any position of a preferred predetermined Hp-Hb complex of fragment thereof. It may however also be desirable to introduce non-conservative substitutions, particularly, but not limited to, a non-conservative substitution in any one or more positions.

A non-conservative substitution leading to the formation of a functionally equivalent fragment of the sequences in FIG. 1 or 2 would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The addition or deletion of an amino acid may be an addition or deletion of from 2 to preferably 10 amino acids, such as from 2 to 8 amino acids, for example from 2 to 6 amino acids, such as from 2 to 4 amino acids. However, additions of more than 10 amino acids, such as additions from 10 to 200 amino acids, are also comprised within the present invention. In the discussion of deletions and additions reference is made to a monomeric form of the complex, i.e. two haemoglobin chains and one haptoglobin chain. In the multimeric forms additions/deletions may be made individually in each monomer of the multimer.

It will thus be understood that the invention concerns Hp-Hb complexes comprising at least one fragment capable of binding at least one CD163 receptor or a variant thereof, including any variants and functional equivalents of such at least one fragment.

The Hp-Hb complex according to the present invention, including any functional equivalents and fragments thereof, may in one embodiment comprise less than 300 amino acid residues, such as less than 275 amino acid residues, such as less than 250 amino acid residues, such as less than 225 amino acid residues, such as less than 200 amino acid residues, such as less than 175 amino acid residues, such as less than 150 amino acid residues, such as less than 125 amino acid residues, such as less than 100 amino acid residues, such as less than 95 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues, such as less than 45 amino acid residues, for example less than 40 amino acid residues, such as less than 38 amino acid residues, for example less than 37 amino acid residues, such as less than 36 amino acid residues, for example less than 35 amino acid residues, such as less than 34 amino acid residues, for example less than 33 amino acid residues, such as less than 32 amino acid residues, for example less than 31 amino acid residues, such as about 30 amino acid residues, for example less than 30 amino acid residues, such as about 29 amino acid residues. The number of amino acid residues relate to the total number of amino acid residues in the complex independent of the complex being a linear amino acid sequence or a non-linear complex of amino acid sequences.

A fragment comprising the CD163 binding region of native Hp-Hb complex is particularly preferred. However, the invention is not limited to fragments comprising the CD163 receptor binding region. Deletions of such fragments generating functionally equivalent fragments of the complex comprising less than the CD163 receptor binding region are also comprised in the present invention. Functionally equivalent complex peptides, and fragments thereof according to the present invention, may comprise less or more amino acid residues than CD163 receptor binding region.

Fragments comprising the CD163 receptor binding region of HP-Hb complex preferably comprises regions capable of binding to the SRCR domains I-IX of the CD163 receptor, such as capable of binding to a region in the SRCR domains I-VIII of the CD163 receptor, capable of binding to a region in the SRCR domains I-VII of the CD163 receptor, capable of binding to a region in the SRCR domains I-VI of the CD163 receptor, capable of binding to a region in the SRCR domains I-V of the CD163 receptor, capable of binding to a region in the SRCR domains I-IV of the CD163 receptor, capable of binding to a region in the SRCR domains I-III of the CD163 receptor, capable of binding to a region in the SRCR domains I-II of the CD163 receptor.

Fragments of the complex preferably comprises at least the heavy chain (β) of haptoglobin or a part of said chain capable of forming complex with haemoglobin.

In particular the fragments may comprise a sequence corresponding to aa 103-347 of sp|P00737 (SEQ ID NO:1) in FIG. 4 or to aa 162-406 of sp|P00738 (SEQ ID NO:2).

In one embodiment mimics may be understood to exhibit amino acid sequences gradually differing from the preferred predetermined sequence, as the number and scope of insertions, deletions and substitutions including conservative substitutions increases. This difference is measured as a reduction in homology between the predetermined sequence and the mimic.

All functional equivalents of Hp-Hb complexes are included within the scope of this invention, regardless of the degree of homology that they show to a predetermined sequence of Hp-Hb complexes. The reason for this is that some regions of the complex are most likely readily mutatable, or capable of being completely deleted, without any significant effect on the binding activity of the resulting fragment.

A functional equivalent obtained by substitution may well exhibit some form or degree of native Hp-Hb activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity between i) a given complex equivalent capable of effect and ii) a preferred predetermined fragment, is not a principal measure of the fragment as a variant or functional equivalent of a preferred predetermined complex fragment according to the present invention.

Fragments sharing at least some homology with a preferred predetermined complex fragment of at least 50 amino acids, more preferably at least 100 amino acids, are to be considered as falling within the scope of the present invention when they are at least about 40 percent homologous with the preferred predetermined Hp-Hb complex or fragment thereof, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous homologous with the predetermined complex fragment. In a preferred embodiment the above percentages for homology also relates to percentage identity.

The Hp-Hb complex is preferably constituted of at least two different chains (sequences) wherein one chain constitutes the haptoglobin part of the complex and the other chain constitutes the haemoglobin part. A mimic of the Hp-Hb complex may however be constituted by one chain (sequence) or multimers of said chain, wherein the chain is a steric equivalent of the Hp-Hb complex.

In addition to the mimics described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In one embodiment the Hp-Hb complex or parts thereof or mimics thereof is synthesised by automated synthesis. Any of the commercially available solid-phase techniques may be employed, such as the Merrifield solid phase synthesis method, in which amino acids are sequentially added to a growing amino acid chain. Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any Hp-Hb complex according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Hp-Hb complexes according to the invention may be synthesised both in vitro and in vivo. Methods for in vitro synthesis are well known. When synthesized in vivo, a host cell is transformed with vectors containing DNA encoding various parts of the Hp-Hb complex. A vector is defined as a replicable nucleic acid construct. Vectors are used to mediate expression of the Hp-Hb complex. An expression vector is a replicable DNA construct in which a nucleic acid sequence encoding the predetermined Hp-Hb complex, or any functional equivalent thereof that can be expressed in vivo, is operably linked to suitable control sequences capable of effecting the expression of the variant, or equivalent in a suitable host. Such control sequences are well known in the art.

A DNA sequence encoding the various parts of the Hp-Hb complex is meaning a DNA sequence encoding the haptoglobin part and a DNA sequence encoding the haemoglobin part. In another embodiment the DNA sequence may be one sequence encoding one peptide sequence which post-translationally is cleaved into the haptoglobin part and the haemoglobin part. In yet another embodiment one peptide constituting both parts is not cleaved, but due to post-translationally folding and/or processing functions as the complex.

Accordingly, one aspect of the invention relates to a DNA sequence encoding a Hp-Hb complex as defined above, the DNA sequence may be a genomic DNA sequence, a cDNA sequence or a mixture of a genomic and a cDNA sequence.

Furthermore, the invention relates to a vector comprising the DNA sequence, as well as to a cell comprising said vector, said cell being capable of expressing the DNA sequence, either as a Hp-Hb complex released into the cell culturing media, or a Hp-Hb complex anchored to the cell membrane.

Cultures of cells may be derived from prokaryotic and eukaryotic cells. In principle, any higher eukaryotic cell culture is workable, whether from vertebrate or invertebrate culture but human cells are preferred. Examples of useful host cell lines $E.$ $coli$, yeast, or human cell lines. Preferred host cells are eukaryotic cells known to synthesize endogenous haptoglobin and/or haemoglobin. Cultures of such host cells may be isolated and used as a source of the variant, or used in therapeutic methods of treatment, including therapeutic methods aimed at diagnostic methods carried out on the human or animal body.

In order to increase the binding affinity the Hp-Hb complex or part thereof or mimic thereof is preferably dimeric. In a more preferred embodiment the Hp-Hb complex or a part thereof or a mimic thereof is multimeric. Dimeric and multimeric relates to the number of haptoglobin monomers. The haemoglobin may be monomeric or dimeric for each haptoglobin chain. There is a correlation between the type of multimeric forms of the Hp-Hb complex and the degree of binding to a CD163 receptor or a CD163 variant of the invention. A multimeric form of a Hp-Hb complex will due to its size have an increased exposure of encountering CD163 variants as when compared to a monomeric, or even a dimeric form, and thus an increased functional affinity to CD163 variants is observed. Furthermore, the multimeric form of the complex may bind to more than one receptor on the CD163 presenting cell leading to increased avidity of the binding.

The multimers may be created by a common linker moiety, such as S—S bridges as in the naturally occurring haptoglobin. The common linker moiety, is preferably located so that complex-forming with haemoglobin is not disturbed. It is preferred that the common linker moiety is located in the light chain of haptoglobin.

According to the invention the Hp-Hb complex, or a part thereof being operably linked to a substance as described above may be for the use as a medicament. Such medicament may operate through a method, wherein the Hp-Hb complex or a part thereof is used in a method of treatment of an individual, comprising the steps of:

i) providing a Hp-Hb complex, or a part thereof or a mimic thereof capable of binding to the CD163 receptor and/or the CD163 variant, ii) operably linking a substance as defined above to the Hp-Hb complex or a part thereof or mimic thereof, iii) administering the medicament comprising the substance operably linked to the Hp-Hb complex to an individual in need thereof.

The term operably linked means that the substance is coupled or bound to the complex in a manner so that the substance is transported to the cell presenting a CD163 receptor or a CD163 variant, whereafter the substance may be released from the complex if appropriate.

Due to the binding of the complex or fragment or mimic thereof to the CD163 receptor and/or a CD163 variant the substance comprised in or bound to the Hp-Hb complex is either taken up by the CD163 presenting cells or at least located in the environment close to the cells. Thereby it is possible to concentrate the substance in or around the cell presenting the CD163 receptor. A test for analysing optional uptake is described below in Example 4.

In one embodiment of the invention the Hp-Hb complex, or a part thereof may be operably linked to a substance, such as a medicament, a gene, a vesicle, vector or the like.

The medicament may be any medicament for which it is desirable to target the drug to a particular tissue or particular cells. In particular the medicament is an antimicrobial agent or a cancer drug.

The medicament is preferably a medicament against diseases in relation to monocytes, such as macrophages. In particular the invention relates to a complex being operably linked to a anti-HIV drug.

In another embodiment the substance is a medicament against lymphomas, such as histiocytic lymphomas.

In yet another embodiment the substance may stimulate the macrophages to produce inter-leukin 6.

In a further embodiment the substance is an antigen for vaccine purposes.

In another embodiment the substance of the Hp-Hb complex, or a functional equivalent thereof comprises a gene, i.e. a gene construct. The gene may be any gene encoding a particular biological function. For example the gene may comprise a nucleic acid, such as PNA, LNA, DNA or RNA, or the gene may comprise cDNA. The gene may also comprise less than full length genes or cDNAs, such as fragment thereof. The Hp-Hb complex comprising a gene may be used in gene-delivery therapy, whereby the gene is taken up by the cell presenting the CD163 receptor or a variant thereof.

The constructs can be introduced as one or more DNA molecules or constructs. The constructs are prepared in conventional ways, where the genes and regulatory regions may be isolated, as appropriate, ligated, cloned in an appropriate cloning host, analyzed by restriction or sequencing, or other convenient means. Using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into host cells by any convenient means, as discussed in more detail below.

The constructs may be introduced as a single DNA molecule encoding all of the genes, or different DNA molecules having one or more genes. The constructs may be introduced simultaneously or consecutively, each with the same or different markers.

The gene may be linked to the complex as such or protected by any suitable system normally used for transfection such as viral vectors or artificial viral envelope, liposomes or micellas, wherein the system is linked to the complex.

Numerous techniques for introducing DNA into eukaryotic cells are known to the skilled artisan. Often this is done by means of vectors, and often in the form of nucleic acid encapsidated by a (frequently virus-like) proteinaceous coat. Gene delivery systems may be applied to a wide range of clinical as well as experimental applications.

Vectors containing useful elements such as selectable and/or amplifiable markers, promoter/enhancer elements for expression in mammalian, particularly human, cells, and which may be used to prepare stocks of construct DNAs and for carrying out transfections are well known in the art. Many are commercially available.

Various techniques have been developed for modification of target tissue and cells in vivo. A number of virus vectors, discussed below, are known which allow transfection and random integration of the virus into the host. See, for example, Dubensky et al. (1984) Proc. Natl. Acad. Sci. USA 81:7529-7533; Kaneda et al., (1989) Science 243:375-378; Hiebert et al. (1989) Proc. Natl. Acad. Sci. USA 86:3594-3598; Hatzoglu et al., (1990) J. Biol. Chem. 265:17285-17293; Ferry et al. (1991) Proc. Natl. Acad. Sci. USA 88:8377-8381. Routes and modes of administering the vector include injection, e.g intravascularly or intramuscularly, inhalation, or other parenteral administration.

Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms.

Another vector which can express the DNA molecule of the present invention, and is useful in gene therapy, particularly in humans, is vaccinia virus, which can be rendered non-replicating (U.S. Pat. Nos. 5,225,336; 5,204,243; 5,155,020; 4,769,330).

Based on the concept of viral mimicry, artificial viral envelopes (AVE) are designed based on the structure and composition of a viral membrane, such as HIV-1 or RSV and used to deliver genes into cells in vitro and in vivo. See, for example, U.S. Pat. No. 5,252,348, Schreier H. et al., J. Mol. Recognit., 1995, 8:59-62; Schreier H et al., J. Biol. Chem., 1994, 269:9090-9098; Schreier, H., Pharm. Acta Helv. 1994, 68:145-159; Chander, R et al. Life Sci., 1992, 50:481-489, which references are hereby incorporated by reference in their entirety. The envelope is preferably produced in a two-step dialysis procedure where the "naked" envelope is formed initially, followed by unidirectional insertion of the viral surface glycoprotein of interest. This process and the physical characteristics of the resulting AVE are described in detail by Chander et al., (supra). Examples of AVE systems are (a) an AVE containing the HIV-1 surface glycoprotein gp160 (Chander et al., supra; Schreier et al., 1995, supra) or glycosyl phosphatidylinositol (GPI)-linked gp120 (Schreier et al., 1994, supra), respectively, and (b) an AVE containing the respiratory syncytial virus (RSV) attachment (G) and fusion (F) glycoproteins (Stecenko, A. A. et al., Pharm. Pharmacol. Lett. 1:127-129 (1992)). Thus, vesicles are constructed which mimic the natural membranes of enveloped viruses in their ability to bind to and deliver materials to cells bearing corresponding surface receptors.

AVEs are used to deliver genes both by intravenous injection and by instillation in the lungs. For example, AVEs are manufactured to mimic RSV, exhibiting the RSV F surface glycoprotein which provides selective entry into epithelial cells. F-AVE are loaded with a plasmid coding for the gene of interest, (or a reporter gene such as CAT not present in mammalian tissue).

The AVE system described herein in physically and chemically essentially identical to the natural virus yet is entirely "artificial", as it is constructed from phospholipids, cholesterol, and recombinant viral surface glycoproteins. Hence, there is no carry-over of viral genetic information and no danger of inadvertant viral infection. Construction of the AVEs in two independent steps allows for bulk production of the plain lipid envelopes which, in a separate second step, can then be marked with the desired viral glycoprotein, also allowing for the preparation of protein cocktail formulations if desired.

Another delivery vehicle for use in the present invention are based on the recent description of attenuated Shigella as a DNA delivery system (Sizemore, D. R. et al., Science 270:299-302 (1995), which reference is incorporated by reference in its entirety). This approach exploits the ability of Shigellae to enter epithelial cells and escape the phagocytic vacuole as a method for delivering the gene construct into the cytoplasm of the target cell. Invasion with as few as one to five bacteria can result in expression of the foreign plasmid DNA delivered by these bacteria.

A preferred type of mediator of nonviral transfection in vitro and in vivo is cationic (ammonium derivatized) lipids. These positively charged lipids form complexes with negatively charged DNA, resulting in DNA charged neutralization and compaction. The complexes endocytosed upon association with the cell membrane, and the DNA somehow escapes the endosome, gaining access to the cytoplasm. Cationic lipid:DNA complexes appear highly stable under normal conditions. Studies of the cationic lipid DOTAP suggest the complex dissociates when the inner layer of the cell membrane is destabilized and anionic lipids from the inner layer displace DNA from the cationic lipid. Several cationic lipids are available commercially. Two of these, DMRI and DC-cholesterol, have been used in human clinical trials. First generation cationic lipids are less efficient than viral vectors. For delivery to lung, any inflammatory responses accompanying the liposome administration are reduced by changing the delivery mode to aerosol administration which distributes the dose more evenly.

The gene may be any gene appropriately expressed by the CD163 presenting cells. In one embodiment the gene may be a gene for CD163 as a gene therapy for individuals having reduced CD-163 expression.

In another embodiment the gene encodes an antigen for as a gene vaccination. In any situation it may be an advantage that macrophages do not multiply whereby this kind of gene therapy is an appropriate form of temporary gene therapy.

The gene therapy approach can be utilized in a site specific manner to deliver a retroviral vector to the tissue or organ of choice. Thus, for example, a catheter delivery system can be used (Nabel, E. G. et al., Science 244:1342 (1989)). Such methods, using either a retroviral vector or a liposome vector, is particularly useful to deliver the gene to a blood vessel wall.

Other virus vectors may also be used, in particular for human gene therapy, including recombinant adenovirus vectors.

A nontoxic and efficient method has recently been reported based on the Sendai virus, also known as hemagglutinating virus of Japan (HVJ). HVJ-liposome-mediated gene transfer is performed Morishita R et al., Hypertension (1993) 21:894-89.

Further, the substance of the Hp-Hb complex, or a part thereof may also comprise a tracer or a marker, such as chromophores, fluorphores, biotin, isotopes, enzymes, for identifying the cells presenting the CD163 receptor or a variant thereof. Thereby Hp-Hb complex may be used for diagnostic purposes as well.

In one embodiment the Hp-Hb complex or fragment thereof or mimic thereof being operably linked to a substance is capable of binding a CD163 variant only, in order to avoid binding to the naturally occurring CD163 receptor on macrophages. Thereby it is possible to direct a substance to a subgroup of cells presenting the CD163 variant only.

It is another object of the present invention to use a CD163 molecule as a medicament. Use of a CD163 molecule in the manufacture of a medicament for treatment of haemolysis in an individual in need of such treatment. There are a number of application fields, wherein one is the use of a CD163 molecule for the removal of at least one Hp-Hb complex in serum and/or plasma of an individual. A second application is the use of a CD163 molecule for the determination of the haemolysis rate of an individual. Further, the use of at least one complex comprising haemoglobin and haptoglobin as a marker for a cell, such as a macrophage expressing a CD163 molecule, wherein at least one of the haemoglobin or haptoglobin molecules are labelled is yet another application area.

According to the invention the term "CD163 variant" is meant to include functional equivalents of CD163, or a fragment of CD163, said CD163 comprising a predetermined amino acid sequence. Thus, a CD163 variant is different from native CD163. A "variant" is defined as:

iv) variants comprising an amino acid sequence capable of being recognised by an antibody also capable of recognising the predetermined amino acid sequence, and/or v) variants comprising an amino acid sequence capable of binding to a Hp-Hb complex also capable of binding the predetermined amino acid sequence, and/or vi) variants having at least a substantially similar binding affinity to at least one Hp-Hb complex as said predetermined amino acid sequence.

By the term "predetermined amino acid sequence" is meant any of the amino acid sequences depicted in FIGS. 5a and 5b, i.e. any of the sequences for CD163 having the following sequence identification in sequence database trEMBL:

| tr\|Q07898\|Q07898 | (SEQ ID NO: 10) |
| tr\|Q07901\|Q07901 | (SEQ ID NO: 11) |
| tr\|Q07900\|Q07900 | (SEQ ID NO: 12) |
| tr\|Q07899\|Q07899 | (SEQ ID NO: 13) |

"Functional equivalency" as used in the present invention is according to one preferred embodiment established by means of reference to the corresponding functionality of a predetermined CD163 fragment.

According to the present invention a functional equivalent of a CD163 variant or fragments thereof may be obtained by addition, substitution or deletion of at least one amino acid. When the amino acid sequence comprises a substitution of one amino acid for another, such a substitution may be a conservative amino acid substitution. Fragments of CD163 according to the present invention may comprise more than one such substitution, such as e.g. two conservative amino acid substitutions, for example three or four conservative amino acid substitutions, such as five or six conservative amino acid substitutions, for example seven or eight conservative amino acid substitutions, such as from 10 to 15 conservative amino acid substitutions, for example from 15 to 25 conservative amino acid substitution. Substitutions can be made within any one or more groups of predetermined amino acids.

Examples of fragments comprising one or more conservative amino acid substitutions including one or more conservative amino acid substitutions within the same group of predetermined amino acids, or a plurality of conservative amino acid substitutions, wherein each conservative substitution is generated by substitution within a different group of predetermined amino acids.

One naturally occurring CD163 variant is the soluble CD163, that may be full length or truncated, such as shortened with the cytoplasmic tail and/or transmembrane segment Accordingly, variant of CD163, or fragments thereof according to the invention may comprise, within the same variant of CD163, or fragments thereof, at least one substitution, such as a plurality of substitutions introduced independently of one another. Variants of CD163, or fragments thereof may thus comprise conservative substitutions independently of one another, wherein at least one glycine (Gly) of said variants of CD163, or fragments thereof of CD163 is substituted with an amino acid selected from the group of amino acids consisting of Ala, Val, Leu, and Ile, and independently thereof, variant of CD163, or fragments thereof, wherein at least one of said alanines (Ala) of said variant of CD163, or fragments thereof is substituted with an amino acid selected from the group of amino acids consisting of Gly, Val, Leu, and Ile, and independently thereof, variant of CD163, or fragments thereof, wherein at least one valine (Val) of said variant of CD163, or fragments thereof is substituted with an amino acid selected from the group of amino acids consisting of Gly, Ala, Leu, and Ile, and independently thereof, variants of CD163, or fragments thereof, wherein at least one of said leucines (Leu) of said variant of CD163, or fragments thereof is substituted with an amino acid selected from the group of amino acids consisting of Gly, Ala, Val, and Ile, and independently thereof, variants of CD163, or fragments thereof, wherein at least one isoleucine (Ile) of said variants of CD163, or fragments thereof is substituted with an amino acid selected from the group of amino acids consisting of Gly, Ala, Val and Leu, and independently thereof, variants of CD163, or fragments thereof wherein at least one of said aspartic acids (Asp) of said variants of CD163, or fragments thereof is substituted with an amino acid selected from the group of amino acids consisting of Glu, Asn, and Gln, and independently thereof, variants of CD163, or fragments thereof, wherein at least one of said phenylalanines (Phe) of said variants of CD163, or fragments thereof is substituted with an amino acid selected from the group of amino acids consisting of Tyr, Trp, His, Pro, and preferably selected from the group of amino acids consisting of Tyr and Trp, and independently thereof, variants of CD163, or fragments thereof, wherein at least one of said tyrosines (Tyr) of said variants of CD163, or fragments thereof of CD163 is substituted with an amino acid selected from the group of amino acids consisting of Phe, Trp, His, Pro, preferably an amino acid selected from the group of amino acids consisting of Phe and Trp, and independently thereof, variants of CD163, or fragments thereof, wherein at least one of said arginines (Arg) of said fragment of CD163 is substituted with an amino acid selected from the group of amino acids consisting of Lys and His, and independently thereof, variants of CD163, or fragments thereof, wherein at least one lysine (Lys) of said variants of CD163, or fragments thereof is substituted with an amino acid selected from the group of amino acids consisting of Arg and His, and independently thereof, variants of CD163, or fragments thereof, wherein at least one of said asparagines (Asn) of said variants of CD163, or fragments thereof is substituted with an amino acid selected from the group of amino acids consisting of Asp, Glu, and Gln, and independently thereof, variants of CD163, or fragments thereof, wherein at least one glutamine (Gln) of said variants of CD163, or fragments thereof is substituted with an amino acid selected from the group of amino acids consisting of Asp, Glu, and Asn, and independently thereof, variants of CD163, or fragments thereof, wherein at least one proline (Pro) of said variants of CD163, or fragments thereof is substituted with an amino acid selected from the group of amino acids consisting of Phe, Tyr, Trp, and His, and independently thereof, variants of CD163, or fragments thereof, wherein at least one of said cysteines (Cys) of said variants of CD163, or fragments thereof is substituted with an amino acid selected from the group of amino acids consisting of Asp, Glu, Lys, Arg, His, Asn, Gln, Ser, Thr, and Tyr.

It is clear from the above outline that the same variant or fragment thereof may comprise more than one conservative amino acid substitution from more than one group of conservative amino acids as defined herein above.

Conservative substitutions may be introduced in any position of a preferred predetermined CD163 variant of fragment thereof. It may however also be desirable to introduce non-conservative substitutions, particularly, but not limited to, a non-conservative substitution in any one or more positions.

A non-conservative substitution leading to the formation of a functionally equivalent fragment of CD163 would for example i) differ substantially in hydrophobicity, for example a hydrophobic residue (Val, Ile, Leu, Phe or Met) substituted for a hydrophilic residue such as Arg, Lys, Trp or Asn, or a hydrophilic residue such as Thr, Ser, His, Gln, Asn, Lys, Asp, Glu or Trp substituted for a hydrophobic residue; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The addition or deletion of an amino acid may be an addition or deletion of from 2 to preferably 10 amino acids, such as from 2 to 8 amino acids, for example from 2 to 6 amino acids, such as from 2 to 4 amino acids. However, additions of more than 10 amino acids, such as additions from 10 to 200 amino acids, are also comprised within the present invention.

It will thus be understood that the invention concerns CD163 variants comprising at least one fragment of CD163 capable of binding at least one Hp-Hb complex, including any variants and functional equivalents of such at least one fragment.

The CD163 variant according to the present invention, including any functional equivalents and fragments thereof, may in one embodiment comprise less than 1000 amino acid residues, such as less than 950 amino acid residues, for example less than 900 amino acid residues, such as less than 850 amino acid residues, for example less than 800 amino acid residues, such as less than 750 amino acid residues, for example less than 700 amino acid residues, such as less than 650 amino acid residues, for example less than 600 amino acid residues, such as less than 550 amino acid residues, for example less than 500 amino acid residues, such as less than 450 amino acid residues, for example less than 400 amino acid residues, such as less than 380 amino acid residues, for example less than 370 amino acid residues, such as less than 360 amino acid residues, for example less than 350 amino acid residues, such as less than 340 amino acid residues, for example less than 330 amino acid residues, such as less than 320 amino acid residues, for example less than 310 amino acid residues, such as about 300 amino acid residues, for example less than 300 amino acid residues, such as about 290 amino acid residues, for example 290 amino acid residues.

A fragment comprising the Hp-Hb binding region of native CD163 is particularly preferred. However, the invention is not limited to fragments comprising the Hp-Hb binding region. Deletions of such fragments generating functionally equivalent fragments of CD163 comprising less than the Hp-Hb binding region are also comprised in the present invention. Functionally equivalent CD163 peptides, and fragments thereof according to the present invention, may comprise less or more amino acid residues than the Hp-Hb binding region.

Fragments comprising the Hp-Hb binding region preferably comprises the SRCR domains I-IX of the CD163 receptor, such as capable of binding to a region in the SRCR domains I-VIII of the CD163 receptor, capable of binding to a region in the SRCR domains I-VII of the CD163 receptor, capable of binding to a region in the SRCR domains I-VI of the CD163 receptor, capable of binding to a region in the SRCR domains I-V of the CD163 receptor, capable of binding to a region in the SRCR domains I-IV of the CD163 receptor, capable of binding to a region in the SRCR domains I-III of the CD163 receptor, capable of binding to a region in the SRCR domains I-II of the CD163 receptor, or a variant thereof.

In a preferred embodiment the fragments comprising the Hp-Hb binding region preferably comprises the SRCR domains I-IX of the CD163 receptor, such as capable of binding to a region in the SRCR domains III-IX of the CD163 receptor, capable of binding to a region in the SRCR domains III-VIII of the CD163 receptor, capable of binding to a region in the SRCR domains III-VII of the CD163 receptor, capable of binding to a region in the SRCR domains III-VI of the CD163 receptor, capable of binding to a region in the SRCR domains III-V of the CD163 receptor, capable of binding to a region in the SRCR domains III-IV of the CD163 receptor, capable of binding to a region in the SRCR domains III or IV of the CD163 receptor, or a variant thereof.

The domains are in one embodiment arranged as follows with respect to the CD163 sequence (SEQ ID NO:10):

Domains defined by position of cystein residues corresponds to
D1: aa 46-146
D2: aa 154-253
D3: aa 261-360
D4: aa 368-467
D5: aa 473-572
D6: aa 578-677
D7: aa 714-814
D8: aa 819-920
D9: aa 924-1023

Numbering according to translated cDNA sequence (Genbank accession no Z22968).

Functional equivalents of variants of CD163 will be understood to exhibit amino acid sequences gradually differing from the preferred predetermined sequence, as the number and scope of insertions, deletions and substitutions including conservative substitutions increases. This difference is measured as a reduction in homology and/or identify between the preferred predetermined sequence and the fragment or functional equivalent.

All fragments or functional equivalents of CD163 variants are included within the scope of this invention, regardless of the degree of homology that they show to a preferred predetermined sequence of CD163 variants. The reason for this is that some regions of CD163 are most likely readily mutatable, or capable of being completely deleted, without any significant effect on the binding activity of the resulting fragment.

A functional variant obtained by substitution may well exhibit some form or degree of native CD163 activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity between i) a given CD163 fragment capable of effect and ii) a preferred predetermined fragment, is not a principal measure of the fragment as a variant or functional equivalent of a preferred predetermined CD163 fragment according to the present invention.

Fragments sharing at least some homology with a preferred predetermined CD163 fragment of at 50 amino acids, preferably at least 100 amino acids, are to be considered as falling within the scope of the present invention when they are at least about 40 percent homologous with the predetermined CD163 variant or fragment thereof, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous homologous with the predetermined CD163 fragment. In a preferred embodiment the percentages mentioned above also relates to identify percentages.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In one embodiment the CD163 variant is synthesised by automated synthesis. Any of the commercially available solid-phase techniques may be employed, such as the Merrifield solid phase synthesis method, in which amino acids are sequentially added to a growing amino acid chain. Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any CD163 variant according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

CD163 variants according to the invention may be synthesised both in vitro and in vivo. Method for in vitro synthesis are well known. When synthesized in vivo, a host cell is transformed with vectors containing DNA encoding the CD163 variant. A vector is defined as a replicable nucleic acid construct. Vectors are used to mediate expression of the CD163 variant. An expression vector is a replicable DNA construct in which a nucleic acid sequence encoding the predetermined CD163 variant, or any functional equivalent thereof that can be expressed in vivo, is operably linked to suitable control sequences capable of effecting the expression of the variant, or equivalent in a suitable host. Such control sequences are well known in the art.

Accordingly, one aspect of the invention relates to a DNA sequence encoding a CD163 variant as defined above, the DNA sequence may be a genomic DNA sequence, a cDNA sequence or a mixture of a genomic and a cDNA sequence.

Furthermore, the invention relates to a vector comprising the DNA sequence, as well as to a cell comprising said vector, said cell being capable of expressing the DNA sequence, either as a CD163 variant released into the cell culturing media, or a CD163 variant anchored to the cell membrane.

Cultures of cells derived from multicellular organisms represent preferred host cells. In principle, any higher eukaryotic cell culture is workable, whether from vertebrate or invertebrate culture. Examples of useful host cell lines are E-coli, yeast or human cell lines. Preferred host cells are eukaryotic cells known to synthesize endogenous CD163. Cultures of such host cells may be isolated and used as a source of the variant, or used in therapeutic methods of treatment, including therapeutic methods aimed at diagnostic methods carried out on the human or animal body.

Multimers and dimers, including homodimers and heterodimers of variants of CD163 according to the invention, are also provided and fall under the scope of the invention. CD163 functional equivalents and fragments can be produced as homodimers or heterodimers with other amino acid sequences or with native CD163 sequences. Heterodimers include dimers containing a CD163 variant binding at least one Hp-Hb complex when present in a homodimer, and a CD163 fragment that need not have or exert any biologically activity.

The binding affinity of the CD163 variant of the invention and a dimeric Hp-Hb complex preferably has a kD value of between 10-100 nM, such as between 20-80 nM, for example between 40-60 nM, such as between 45-55 nM.

The CD163 variant of the invention preferably has a Kd binding affinity for a multimeric Hp-Hb complex of the invention of between 2-10 nM.

A dimeric Hp-Hb complex preferably has a binding affinity to two CD163 receptors on a cell in the range of from 0.05 to 1.0 nM.

The binding affinity may be determined as discussed in Example 2 and 3 below.

One aspect of the invention relates to a composition comprising at least one purified CD163 receptor and/or at least one purified CD163 receptor variant as defined above.

Another aspect of the invention relates to a composition comprising a Hp-Hb complex or a part thereof or a mimic thereof as defined above.

The composition(s) is(are) particularly useful in the manufacture of a medicament for any of the uses discussed below.

The medicament is preferably suitable for parenteral administration, such as intravenous, intramuscular, subcutaneous, or intravenous administration. Thus, the medicament may further comprise any suitable carriers, adjuvants, and/or additives conventionally used for the preparation of medicaments, in particular medicaments for parenteral administration. Another suitable administration route is via inhalation.

The present invention further relates to the following applications of Hp-Hb complexes and/or a variant thereof. One such use is in the manufacture of a medicament for treatment of conditions related to haemolysis in an individual in need of such treatment. Another such use of at least one CD163 or a variant thereof is for the removal of at least one Hp-Hb complex in serum and/or plasma of an individual. The invention may also be used for the determination of the haemolysis rate of an individual. This may be done by determining the level of the binding activity between the CD163 variant and the Hp-Hb complexes, as an indication of the rate with which red blood cells are lysed.

The invention also relates to the use of at least one CD163 molecule for the identification of at least one Hp-Hb complex in serum and/or plasma of an individual.

In yet another aspect the invention relates to the uses of at least one complex comprising haemoglobin and haptoglobin. For example the complex may be used as a marker for a cell expressing CD163 or a CD163 variant, wherein at least one of the haemoglobin or haptoglobin molecules are labelled. Such cell may be a macrophage. Another use is for the delivery of at least one drug/medicament or at least one gene to a cell expressing CD163 or a CD163 variant. The processes of drug and gene-delivery are mentioned above.

The purpose of drug or gene delivery is to localize the drug to the target site. Such targeted delivery systems often take the form of injectables composed of liposomes and microspheres made of proteins. Polymeric systems share some of the advantages of liposomal systems such as altered pharmacokinetics and biodistribution. While liposomes might have better prospects of biocompatibility and potential for fusion with cells, polymeric microspheres have more controllable release kinetics, better stability in storage, and higher drug-loading levels for some classes of compounds. The delivery system is targetted through a linkage to at least one Hp-Hb complex capable of binding to CD163 or a variant thereof.

The delivery may made in vivo or in vitro, the latter in particular being for experimental purposes.

In particular the drugs and genes delivered may be selected from the medicaments discussed above.

The deliberate introduction of DNA encoding a desired gene, under conditions where the gene may be expressed within the cell and leads to the production of RNA and/or protein, can be desirable in order to provoke any of a wide range of useful biological responses. The Hp-Hb complex can carry heterologous genes under the control of promoters able to cause their expression in vectors.

In another aspect of the invention the gene therapy comprises introducing a nucleic acid sequence to up-regulate or down-regulate expression of a target gene in the host cell, either by means of a protein encoded by the introduced nucleic acid sequence or by means of an anti-sense relation between RNA encoded by the introduced nucleic acid and a target nucleic acid molecule corresponding to an endogenous gene product.

An example of anti-atherosclerotic drugs to be delivered to macrophages by complex formation with Hp-Hb and subsequent uptake via HbSR/CD163:

Specific or non-specific Peroxisome proliferator-activated receptor (PPAR) agonists such as polyunsaturated fatty acid (FA), modified Fas, conjugated Fas, oxidized Fas, FA-derived eicosanoids, fibrate normolipidaemic agents (e.g. phenofibrate), antidiabetic gliazones.

One effect of these drugs might be to stimulate PPAR activity and thereby the efflux of cholesterol in macrophage-derived foam cells in atherosclerotic lesions.

In yet another embodiment the substance linked to the Hp-Hb complex or a part thereof or a mimic thereof may also be an antibody directed to a target desired to be cleared from plasma, which is accomplished when the antibody binds the target and the Hp-Hb complex or a part thereof or a mimic thereof linked to the antibody binds a CD163 receptor on for example a macrophage followed by cellular uptake and optional degradation of the target. This embodiment may for example be used for clearing myoglobin from plasma after muscle injuries, using an antibody directed to myoglobin.

In yet another embodiment the Hp-Hb complex mimic linked to a substance may be a fusion protein of an antibody directed to Hp-Hb complex or CD163 receptor and an antibody directed to a target desired to be cleared from the plasma as discussed above.

It is a further object of the present invention that the CD163 or CD163 variant is applied in a method comprising the treatment of haemolysis in an individual in need of such treatment. Lysis of red blood cells may occur in a number of physiological and pathological conditions. The release of haemoglobin to the plasma presents a serious physiological threat. Administration of CD163 or the CD163 variant leads to a binding between the Hp-Hb complexes formed due the haemolysis and CD163, whereby fewer Hp-Hb complexes are taken up by the macrophages leading to a less severe hemosiderosis.

In another embodiment the same effect may be obtained by administrating antibodies directed to the CD163 receptor. The antibodies may be monoclonal, such as those mentioned below in the examples or polyclonal. Production of antibodies is known to the skilled person.

In a further embodiment Hp-Hb complexes are administered to inhibit uptake of native Hp-Hb complexes again leading to a less severe hemosiderosis.

In yet a further aspect of the invention the CD163 variant is used in a method for the removal of at least one Hp-Hb complex in serum and/or plasma of an individual. Since the present inventors have now established CD163 and CD163 variants as the acute phase-regulated capture protein for Hp-Hb complexes the CD163 variant may be applied to an individual in need of plasma haemaglobin clearance.

This may also be accomplished by gene therapy, by administration of genes encoding CD163 or a variant thereof, in order to produce cells capable of assisting the macrophages in case of plasma haemoglobin clearance.

In another embodiment of the invention the CD 163 variant is used in a diagnostic method. One such diagnostic method is for marking a cell expressing a CD163 variant, wherein at least one of the haemoglobin or haptoglobin molecules or parts thereof are labelled. It is possible to identify CD163 variants in vitro as well as in vivo by bringing into contact at least one Hp-Hb complex with an environment comprising CD163 variants. The individual haemoglobin or haptoglobin molecules may be labelled with a marker as discussed above. In one aspect of the invention the CD163 variant is used in a diagnostic method for identifying monocytes and/or macrophages in an individual or in vitro.

In another aspect the CD163 variant is used in a method for the identification of at least one Hp-Hb complex in serum and/or plasma of an individual.

In this aspect the CD163 variant may be used for determination of the haemolysis rate of an individual.

Furthermore, the Hp-Hb complex linked to a marker may be used for identification of monocytes, such as macrophages, in tissues, such as sections of tissues for example for microscopic examinations.

In another embodiment the Hp-Hb complex linked to a marker may be used for detection of CD163, either membrane bound CD163 and/or soluble CD 163. In particular the Hp-Hb complex linked to a marker may be used for detection soluble CD 163 in a sample, such as a blood sample. This could also be detection using labelled Hp-Hb complex. The label could be a chromophore, a fluorochrome, a radioactive isotope, biotin or an enzyme The invention also relates to the following applications of detection of soluble CD163. CD163 may be detected by any of the methods described above in relation to Hp-Hb complex. Furthermore CD163 may be detected by any other method known to the person skilled in the art, such as through the use of antibodies, monoclonal and/or polyclonal, directed to CD163. This could also be detection using labelled antibodies. The label could be a chromophore, a fluorochrome, a radioactive isotope, biotin or an enzyme.

Furthermore, CD163 may be detected using labelled Hemoglobin (Hb) and/or haptoglobin, labelled as discussed above for antibodies.

The detection of soluble CD163 may be used as tools in diagnosis, monitoring and control of patients.

For example, one use of soluble CD163 is as a diagnostic marker in diagnosis, monitoring, and control of patients with hemolysis and/or other hematological conditions (e.g. aplastic anemia, iron-deficiency anemia, megaloblastic anemia, sickle-cell anemia, polycytemia, malaria, leucemia, myelodysplasia, lymfoma, leukopenia, splenectomia).

Another use of CD163 is as an acute phase marker, because soluble CD163 is upregulated during acute phase response. Hence Soluble CD163 can be used in diagnosis, monitoring, and control of patients with inflammation (infection, cancer, autoimmunity) as well as in diagnosis, monitoring, and control of patients with immunodeficiency.

Still another use is in monitoring, and control of patients treated with glucocorticoids and/or cytostatics and/or other medications.

The concentration of soluble CD163 may be determined using any suitable methods. One of the following techniques are particularly suitable.

One assay could be Sandwich-ELISA and/or competitive-ELISA using a detection system, which could be peroxidase-labeled antibody/OPD system, other enzymes than peroxidase, chemiluminiscense, fluorescense, biotin-avidin-systems.

Another assay could be nefelometric- or turbidimetric assays, radio-immuno-assays (RIA), purification of CD163 by e.g. chromatography or electrophoresis and detection by e.g. photometry, chromatography combined with mass-spectophotometry.

The CD163 concentration could be determined in serum and plasma, which could be stabilised with EDTA, citrate or heparin, as well as in blood, urine, cerebrospinal fluid, and other body-fluids of human and/or animal origin. Furthermore the assays can be used for measuring the concentration of CD163 in artificial media e.g. cell-culture-media.

EXPERIMENTALS

Example 1

Purification and Identification of the Hp-Hb Receptor

Human Hp (1-1, 2-2, and mixed phenotypes) and human Hb ($A_0$, $A_2$ and S forms) were from Sigma. A five ml Hp-Hb SEPHAROSE® CL-4B agarose (Pharmacia-Amersham) column was prepared by coupling complexes of Hp (5 mg, mixed phenotypes) and Hb (4 mg, type $A_o$). The column was loaded with 100 ml ~1% TRITON® X-100 detergent-solubilised membranes (from human spleen, placenta, and liver), prepared as previously described (Moestrup, S. K., Kaltoft, K., Sottrup-Jensen, L. & Gliemann, J. The human $\alpha_2$-macroglobulin receptor contains high affinity calcium binding sites important for receptor conformation and ligand recognition. *J. Biol. Chem.* 265, 12623-12628 (1990). The purified 130 kDa protein binding Hp-Hb was eluted in 10 mM $NaH_2PO_4$ (pH 6), 150 mM NaCl, 5 mM EDTA and 0.5% CHAPS (Aldrich). SDS-gel separated protein was processed for tryptic digestion and MALDI mass spectrometry by Protana (Odense, Denmark). The difference in calculated and measured masses was for all peptides less than 0.042 kDa. The murine monoclonal CD163 antibodies EDHu-1 (Serotec) and GHI/61 (Research Diagnostics) were used for western blotting. A polyclonal CD163 antibody was raised by immunisation of a rabbit with ligand-affinity purified receptor.

Example 2

Ligand-Receptor Binding Analysis

Surface plasmon resonance analysis was carried out as described Moestrup, S. K. et al. $\beta_2$-glycoprotein-I (apolipoprotein H) and $\beta_2$-glycoprotein-I-phospholipid complex harbor a recognition site for the endocytic receptor megalin. *J. Clin. Invest* 102, 902-909 (1998). Purified CD163 was immobilised at the BIAcore® sensor CM5 chip (BIAcore AB) at a concentration of up to 50 µg/ml in 10 mM sodium acetate, pH 4.0, and the remaining binding sites were blocked with 1 M ethanolamine pH 8.5. The surface plasmon resonance signal generated from immobilised CD163 corresponded to 55-66 fmol receptor/$mm^2$. The sample and flow buffer was 10 mM Hepes, 150 mM NaCl, 0.5 mM $CaCl_2$, pH 7.4. The sensor chips were regenerated with 1.6 M glycine-HCl, pH 3. The binding assay for measuring binding of $^{125}$I-Hp-Hb to human CD163 immobilised in microtiter plate wells (Nunc) was carried out as de-scribed Birn, H. et al. Characterization of an epithelial approximately 460-kDa protein that facilitates endocytosis of intrinsic factor-vitamin B12 and binds receptor-associated protein. *J. Biol. Chem.* 272, 26497-26504 (1997).

The microtiter plates were coated at 4° C. for 20 h with purified CD163 in 50 mM $NaHCO_3$ containing 250 ng CD163 per well (for binding $^{125}$I-Hp(1-1)-Hb) or 125 ng CD163 per well (for binding $^{125}$I-Hp(2-2)-Hb). Iodination of Hp-Hb was performed with the chloramine-T-method. Ligand blotting was carried out as described using $10^6$ cpm radioligand/ml (Moestrup, S. K. & Gliemann, J. Analysis of ligand recognition by the purified $\alpha_2$-macroglobulin receptor (low density lipoprotein receptor-related protein). Evidence that high affinity of $\alpha_2$-macroglobulin-proteinase complex is achieved by binding to adjacent receptors. *J. Biol. Chem.* 266, 14011-14017 (1991).$\alpha$ Hp is synthesised as a single chain, which is post-translationally cleaved into an amino-terminal $\alpha$ chain and a carboxy-terminal $\beta$ chain. The basic structure of Hp, as found in most mammals, is a homodimer (FIG. 2a), in which the two Hp molecules are linked by a single disulfide bond via their respective ~9 kDa $\alpha$ chains[14]. In man, a variant with a long $\alpha$ chain is also present in all populations. This variant arose apparently by an early intragenic duplication, presumably originating from an unequal crossover of two basic alleles, resulting in an Hp with an $\alpha$ chain of ~14 kDa. The short and long $\alpha$ chains are designated as $\alpha$1 and $\alpha^2$, respectively. Since the cysteine forming the intermolecular disulfide bond between the $\alpha$ chains is also duplicated, humans carrying the long variant allele exhibit a multimeric Hp phenotype (FIG. 2a).

Analysis of the binding of Hp-Hb complexes (FIG. 2a) to immobilised CD163 revealed a high-affinity binding of both dimeric and multimeric Hp-Hb complexes (FIGS. 2b and c). FIG. 2b shows a surface plasmon resonance analysis of CD163 binding of the dimeric Hp(1-1)-Hb complex and the multimeric Hp(2-2)-Hb complex. No binding of non-complexed Hb (FIG. 2b, left panel) nor Hp(1-1) or Hp(2-2) (FIG. 2b, middle and right panels) was detected thus indicating that a neoepitope for receptor binding is expressed in the Hp-Hb complex. Accordingly, maximal receptor binding was measured, when the Hb binding capacity of Hp reached saturation (FIG. 2b, middle and right panels) at equimolar concentrations of Hb and Hp. The Hp(2-2)-Hb complex yielded a higher response and the dissociation was slower as compared to the Hp(1-1)-Hb complex. The results shown were obtained using the $A_0$ ($\alpha_2\beta_2$) form of Hb. Similar results were obtained using the $A_2$ ($\alpha_2\delta_2$) form or the S form (Hb with the mutation for sickle cell disease)[15] (data not shown).

Example 3

Binding Affinity

A solid phase assay with immobilised CD163 in microtiter wells was used for various inhibition experiments (FIG. 6c). This analysis revealed that the removal of $Ca^{2+}$ with EDTA or the addition of polyclonal anti-CD163 IgG completely abolished the binding of Hp-Hb to CD163. Measuring the true affinity of the one-site interaction of Hp-Hb binding to CD163 was hampered by the suggested divalency (Hp(1-1)) and multivalency (Hp(2-2)) of the ligand in terms of receptor-recognition sites. However, competition for CD163-binding of $^{125}$I-labelled Hp-Hb by unlabelled Hp(1-1)-Hb and Hp(2-2)-Hb complexes showed, as anticipated from the surface plasmon resonance experiments, an ~10 fold higher functional affinity (avidity) of the multimeric Hp(2-2)-Hb complexes (FIG. 6c). The concentration of unlabelled Hp(1-1)-Hb complex causing 50% inhibition of the binding of $^{125}$I-labelled Hp(1-1)-Hb was ~0.3 µg/ml, giving an 'apparent $K_d$' of ~2 nM of the dimeric Hp(1-1)-Hb complex. In contrast, the 50% inhibition point for Hp(2-2)-Hb was at ~0.1 µg/ml giving an 'apparent $K_d$' of ~0.2 nM (on assumption of the 2-2 multimer distribution previously calculated Wejman, J. C., Hovsepian, D., Wall, J. S., Hainfeld, J. F. & Greer, J. Structure and assembly of haptoglobin polymers by electron microscopy. *J. Mol. Biol.* 174, 343-368 (1984).). The higher functional affinity of the 2-2 type complex is probably accounted for by its higher valency. Similar 'bonus effect of multivalency' is well known in other biological systems, e.g. the binding of the pentameric IgM molecule to several identical surface antigens.

Example 4

Endocytosis Analysis in CD163-Transfected CHO Cells and in SU-DHL Cells

The cDNA encoding the most abundant variant of CD163 (Genbank/EMBL accession no Z22968) Law, S. K. et al. A new macrophage differentiation antigen which is a member of the scavenger receptor superfamily. *Eur. J. Immunol.* 23, 2320-2325 (1993) was ligated into the KpnI and NotI sites of the mammalian expression vector pcDNA3.1/Zeo(+) (Invitrogen). Stable transfected CHO clones expressing CD163 were established by limited dilution and selection with 500 µg/ml ZEOCIN™ antibiotic (Invitrogen). Expression products were analysed by immunoblotting of growth medium and cell lysate using the rabbit polyclonal antibody against the ligand-affinity purified human CD163.

Endocytosis of $^{125}$I-Hp-Hb in CD163-tranfected and mock-transfected CHO cells growing as confluent adherent monolayers in 24-well plates was analysed as previously described Moestrup, S. K. & Gliemann, J. Analysis of ligand recognition by the purified $\alpha_2$-macroglobulin receptor (low density lipoprotein receptor-related protein). Evidence that high affinity of $\alpha_2$-macroglobulin-proteinase complex is achieved by binding to adjacent receptors. *J. Biol. Chem.* 266, 14011-14017 (1991). Endocytosis in the soluble SU-DHL-1 histiocytic lymphoma cells ($2 \times 10^6$ cell/ml) was analysed as described Moestrup, S. K., Christensen, E. I., Sottrup-Jensen, L. & Gliemann, J. Binding and receptor-mediated endocytosis of pregnancy zone protein-proteinase complex in rat macrophages. *Biochim. Biophys. Acta* 930, 297-303 (1987).

CD163-mediated endocytosis of $^{125}$I-Hp-Hb complexes was studied in Chinese Hamster Ovary (CHO) cells transfected with CD163 cDNA (the abundant CD163 form, Genbank/EMBL accession no Z22968). FIG. 7a (middle panel) shows the time course of cell-associated radioactivity and trichloroacetic acid (TCA)-soluble radioactivity (representing degraded ligand) in the medium. The cell-associated radioactivity reached a plateau after one hour of incubation, and about this time, the TCA-soluble radioactivity significantly increased in the medium. Consistent with an endocytic uptake of Hp-Hb, a similar experiment conducted in the presence of the lysosomal inhibitors, chloroquine and leupeptin, showed a continual increase in cell-bound radioactivity for 3 hours with essentially no TCA-soluble radioactivity detected (FIG. 7a, right panel).

The endocytosis of Hp-Hb complexes was mediated by CD163, since no uptake, and consequently no TCA-soluble radioactivity, was detected in incubations with CHO cells not expressing the CD163 antigen (FIG. 7a, left panel). Furthermore, uptake and degradation of $^{125}$I-labelled Hp(2-2)-Hb can be inhibited by purified IgG from anti-CD163 serum and by unlabelled Hp(2-2)-Hb complexes (FIG. 7b, left panel). Similar results (FIG. 7b, right panel) were obtained with the myelo-monocytic SU-DHL-1 cell line (Epstein, A. L. et al. Biology of the human malignant lymphomas. IV. Functional characterization of ten diffuse histiocytic lymphoma cell lines. *Cancer* 42, 2379-2391 (1978), the only cell line Pulford, K., Micklem, K., Law, S. K. & Mason, D. Y. in Leukocyte Typing VI. (eds. Kishimoto, T. et al.) 1089-1091 (Garland Publishing Inc, New York, 1997) known to express the CD163 antigen, and with $^{125}$I-labelled Hp(1-1)-Hb complexes although a lower rate of uptake was observed in comparison with the $^{125}$I-labelled Hp(2-2)-Hb complexes (data not shown). The SU-DHL cell line expresses, in addition to the most abundant CD163 variant, also two less abundant variants Law, S. K. et al. A new macrophage differentiation antigen which is a member of the scavenger receptor superfamily. *Eur. J. Immunol.* 23, 2320-2325 (1993) with different cytoplasmic tails.

Example 5

Methods of Detection and Measuring of Soluble CD163 (sHbSR) in Plasma and Serum

Soluble CD163 has been detected in plasma in normal human subjects by ELISA and Western blotting. The western blot shows a protein of identical electrophoretic mobility as full length HbSR/CD163 indicating that the protein in plasma either represents the full length protein or only a slightly truncated protein. Because the protein is soluble in plasma we designate it soluble CD163 (sHbSR)

The following Sandwich-ELISA-type assay for measuring the concentration of sHbSR has been developed:

Polyclonal antibody (Rabbit-antiCD163, produced by DAKO for S. K. Moestrup) is coated onto micro-titer wells (concentration in buffer 4 mg/l). Plates are kept at 4° C. until use.

The wells are washed 3 times in phosphate-buffered saline (PBS), and 100 microliter (µl) of each sample (e.g. plasma or serum, diluted 50 times in PBS with albumin) is subsequently added to the wells. The samples incubate for 1 hour at 22° C. with agitation.

The wells are washed again 3 times in PBS, and 100 µl of monoclonal antiCD163 (GHi/6, produced by PharMingen, diluted 500 times in PBS with albumin) is added to each well. The antibody incubates for 1 hour at 22° C. with agitation.

The wells are washed again 3 times in PBS, and 100 µl of polyclonal, peroxidase-labeled antibody (Goat-antirabbit (P447) produced by DAKO, diluted 8000 times in PBS with albumin) is added to each well. The antibody incubates for 1 hour at 22° C. with agitation.

The wells are washed again 3 times in PBS, and 100 µl of a substrate-solution (OPD, orthophenyldiamine, with $H_2O_2$ added) is added to each well, and the colour-development is subsequently stopped after 15-30 min by addition of 50 µl of 1 M $H_2SO_4$.

The intensity of the colour is proportional to the concentration of sHbSR in the sample, and is measured in a micro-plate reader at a wavelength of 495 nm (using 620 nm as a reference). Standards with known concentrations of sHbSR are analysed in the same way on the same plate, and a standard curve can be produced. The colour-intensity of the sample, therefore can be transformed into concentration by comparing with the standard curve (FIG. 8).

Assay-Characteristics

Assay precision: Coefficient of variation=2-4% in the measuring range (intraserial) Detection limit (the minimum measurable concentration): approximately 0.2 µg/l Bias: no matrix effect has been observed in plasma samples of different dilution Specificity: In western-blots (of serum after affinity-purification with polyclonal anti-CD163, and subsequent blotting with monoclonal antiCD163) one single band is observed, with a molecular size corresponding to soluble HbSR. For Western blotting, sHbSR in 100 µl plasma is initially captured by a polyclonal anti-human HbSR/CD163 antibody linked to Sepharose. The beads are washed and subjected to traditional non-reducing SDS-gelelectrophoresis and western blotting with a monoclonal anti-human HbSR/CD163 antibody. The capturing reagent and detecting reagent may be modified as in the ELISA assay described above.

Concentration of sCD163 in Blood Donors and Patients

The mean concentration of sHbSR in plasma from 31 blood donors was 265 µg/l.

The concentration in 31 paired serum samples was not different 264 µg/l), indicating that both sample types can by used in the assay.

In preliminary experiments, randomly assayed samples from patients from a hematological department, have shown values ranging from the normal values found in blood donors to values 5-10 times higher.

Example 6

Uptake in HbSR Expressing Cells of a Heterogeneous Moiety Covalently Linked to Hb-Hp The uptake was tested on transfected CHO-cells recombinantly expressing wt HbSR (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201), CHO-cells expressing the human receptor cubilin (Kristiansen, M., Kozyraki, R., Jacobsen, C., Nexo, E., Verroust, P. J., and Moestrup, S. K. (1999) Molecular dissection of the intrinsic factor-vitamin B12 receptor, cubilin, discloses regions important for membrane association and ligand binding, J. Biol. Chem. 274, 20540-20544) was used as control. Cells were grown on chamber slides (LAB TEK® system, PERMANEX™ slide Nalge Nunc International) at 37° C. and 5% $CO_2$, for 20 hours. Each well was incubated for 1 hour at 37° C. and 5% $CO_2$ with 300 µL of CHO-media (hyQ-CCM5, HyClone (Utah, USA)) added ALEXA FLUOR® 488 labeled Hp(2-2)-Hb (labeled using the ALEXA FLUOR® 488 Protein Labeling Kit (Molecular Probes, Oregon)) to a final concentration of 0.1 µM. The wells were washed twice with PBS pH 7.4 and incubated for 30 min. at room temperature with Ellis buffer (PBS pH 7.4 and 4% formaldehyde). Washed three times with PBS pH 7.4, 0.05% TRITON® X-100 and incubated for 1 hour at room temperature with PBS pH 7.4, 0.05% TRITON® X-100 added rabbit derived polyclonal antibody recognizing either HbSR or cubilin (control cells), with a final concentration of antibody of 10 µg/ml. Wells were washed trice in PBS pH 7.4, 0.05% TRITON® X-100 and incubated for 1 hour at room temperature with PBS pH 7.4, 0.05% TRITON® X-100 added ALEXA FLUOR® 594-labeled goat anti-rabbit IgG (Molecular Probes, Oregon) at a concentration of 5 µg/ml. Finally the wells were washed three times with PBS pH 7.4, 0.05% TRITON® X-100 and overlaid with a cover plate and the fluorescence studied in the confocal micro-scope, see FIG. 9.

As can be seen both receptors react positively with their respectively antibody; red color. Only the cells expressing HbSR also take up ALEXA FLUOR® 488 labeled Hp-Hb; green color, whereas the mock cells, expressing cubilin, do not take up Hp-Hb. The distinct coloring pat-tern of ALEXA FLUOR® 488 in CHO cells expressing HbSR indicates that the complex is degraded in the lysomes of the cell. This result shows that a heterogeneous moiety can be coupled to Hp-Hb and selectively taken up by cells expressing HbSR, which in vivo natively will be macrophages.

Example 7

Localization of the Hp-Hb Binding Region of HbSR

Expression of Recombinant Soluble HbSR

A recombinant soluble HbSR derivative consisting of the extracellular domain (SRCR 1-9) without transmembrane segment and cytoplasmic tail was expressed in Chinese Hamster Ovary (CHO) cells stably tranfected with a HbSR cDNA fragment encoding amino acid 1-1045 of human HbSR. The cDNA plasmid was generated by the following procedure: Initially, a cDNA fragment corresponding to the bases 3045 to 3135 with the addition of a stop codon and a Not I site was created by PCR using the primers: 5'caa gga aga cgc tgc agt gaa ttg c3' and 5'tca gcg gcc gcc tag gat gac tga cgg gat gag c3' with full-length HbSR cDNA (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201) as template. The PCR generated DNA fragment was ligated into the internal Pst I site (position 3056-3061) and the Not cloning site of the previously described full-length HbSR pcDNA(+) plasmid (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201). This procedure substituted bases 3136 to 3351, encoding the transmembrane region and the cytoplasmatic tail of HbSR, with a stop codon. The expression product from the transfected CHO cells was as expected secreted into the medium as a soluble protein. Minor amounts were purified from the medium by haptoglobin-hemoglobin affinity chromatography as described previously (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201).

Expression of Recombinant Fragments of HbSR Corresponding to SRCR 1-6 and SRCR 5-9 cDNA encoding SRCR domain 1-6 and SRCR domain 5-9 extended with Hind III and Xho I restriction sites were amplified by polymerase chain reactions (PCR) using full-length HbSR cDNA (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201) as template. The PCR products were subcloned into the expression vector pSecTag2B (Invitrogen, Groningen, The Netherlands) by use of the restriction sites HindIII and XhoI. Plasmids were transformed into E. coli DH5α cells (Clontech, Palo Alto, Calif., USA), and plasmid DNA isolated and sequenced prior to transfection. The following primers were used for construction of the fragments: SRCR domain 1-6: forward 5'-caagct-tggaacagacaaggagctg-3' (SEQ ID NO:22) and reverse 5'-cctcgagtcctgagcagattacagag-3' (SEQ ID NO:23). SRCR domain 5-9: forward 5'-caagcttcacagggaacccagactg-3' (SEQ ID NO:24) and reverse 5'-cctcgagatctgtgcaattcactgc-3' (SEQ ID NO:25).

CHO-K1 cells were transfected with plasmids and expression products detected by Western blotting using a rabbit polyclonal antibody against human HbSR, as described (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201). Recombinant HbSR SRCR 1-6 was purified by Hp-Hb-affinty chromatography as described for full length recombinant HbSR, while HbSR SRCR domain 5-9 failed to bind to Hp-Hb-SEPHAROSE®. Binding of Hp-Hb to the HbSR derivative corresponding to SRCR domain 1-6 immobilized on a BIACore® CM5 chip was confirmed by BIACore® binding analysis (Biacore International AB, Uppsala, Sweden) as described (Kristiansen, M., Graversen, J. H., Jacobsen, C., Sonne, O., Hoffman, H., Law, A. S. K., and K., M. S. K. (2001) Identification of the hemoglobin scavenger receptor, Nature 409, 198-201). For the sensorgram shown on FIG. 10 the density of HbSR and HbSR SRCR domain 1-6 coupled on the chip was 0.0659 and 0.0370 pmol/mm$^2$, respectively, the concentration of Hp(1-1)-Hb used was 280 nM or 0.04 mg/ml, and the buffer used was CaHBS from BIACore.

Purification and Characterization of an Autoproteolytic HbSR Fragment

In the process of purifying HbSR an autoproteolytic product of HbSR co-purified on Hp-Hb-sepharose. N-terminal sequencing of the fragment revealed the following sequence for the major form: DGVTE, corresponding to amino acid residues 265-269 of HbSR. Estimated by the mobility in SDS-PAGE analysis the fragment correspond to HbSR amino acid residues 265-1116, thus all of HbSR except SRCR domain 1 and 2.

Conclusion

Fragments of HbSR containing SRCR domains 1-6 and 3-9 bound Hp-Hb, while a fragment containing HbSR domain 5-9 failed to bind Hp-Hb. Thus SRCR domain 3 and 4 are necessary for HbSR binding to Hp-Hb.

Example 8

Production of Antibodies Directed to Hp-Hb Complex and CD163 Receptor.

Two Fab antibody libraries expressed on phage to isolate Fab antibodies for structure-function analysis on the Hp-Hb complex-CD163 interaction.

Proteins and chemicals—Human CD163 was purified as described (Kristiansen, M., Graversen, J. H., Jacobsen, C., Sonne, O., Hoffman, H. J., Law, S. K., and Moestrup, S. K. (2001) Nature 409(6817), 198-201.). Hb and Hp (mixed phenotypes, 1:1 or 2:2 forms) purchased from Sigma, were mixed on ice in equal molar amounts to allow for complex formation and dialyzed against HEPES-containing buffer at pH 7.4 before use. Anti-Hb and anti-Hp antibodies were purchased from Sigma. An anti-M13-peroxidase coupled antibody and mixed deoxy-nucleotides were purchased from Amersham-Pharmacia Biotech. DNA modifying enzymes were purchased from Invitrogen and New England Biolabs. Oligonucleotides were obtained from DNAtechnology, Taq polymerase was from Promega. Proteins were labeled using the chloramine-T method. All other reagents and chemicals were reagent grade (Sigma and Merck).

Construction of phage-displayed Fab libraries—Phage display libraries were constructed using the pCOMB3X system (Andris-Widhopf, J., Rader, C., Steinberger, P., Fuller, R., and Barbas, C. F., 3rd. (2000) J Immunol Methods 242(1-2), 159-81.). The pCOMB3X phagemid which was kindly supplied by Dr. C. F. Barbas (the Scripps Research Institute in La Jolla, USA). Two Balb/C mice were immunized three times with 10 µg purified Hp-Hb complexes diluted in incomplete Freund's adjuvans during a period of 6 weeks. Subsequently, mice were sacrificed and spleens were isolated. Using a filter, single cell suspensions were obtained which were suspended in TRIzol® reagent (Invitrogen, the Netherlands) and RNA was isolated following the instructions of the supplier. Using approximately 10 µg total RNA, first strand synthesis was carried out using the SuperScript® II first strand synthesis system (Invitrogen, the Netherlands) and 3' end primers specific for the mouse first constant domain of the heavy chain or for the mouse kappa light chain constant domain (Kang, A. S., Burton, D. R., and Lerner, R. A. (1991) Methods: A Companion to Methods in Enzymology 2(2), 111-118) exactly following the procedure from the supplier. In an extensive set of polymerase chain reactions using well-described primers (Kang, A. S., Burton, D. R., and Lerner, R. A. (1991) Methods: A Companion to Methods in Enzymology 2(2), 111-118), specific cDNA's encoding variable and first constant domains of the IgG1 and IgG2a heavy chains and complete IgG1 and IgG2a kappa light chains were amplified. Optimal temperature conditions were sorted out using a Stratagene ROBOCYCLER® temperature cycler. Amplified products were subsequently purified, digested and ligated into the restriction sites of cleaved pCOMB3X as described in (Kang, A. S., Burton, D. R., and Lerner, R. A. (1991) Methods: A Companion to Methods in Enzymology 2(2), 111-118). Electrocompetent *Escherichia coli* XL1-BLUE® cells (Stratagene) were transformed using an Eppendorf electroporator and ligation efficiency and size of the library determined. Upon infection with VCS M13 helper phage (Stratagene) phage-antibody libraries were obtained that on average consisted of 5×10$^5$ individual colonies.

Selections of anti-Hb-Hp and anti-CD163 antibody phage—Phage selections were performed in 96-well plates (NUNC, Denmark) coated with 1 µg of purified Hp-Hb complexes or CD163 and blocked with BSA. Pannings were done essentially as described (Horn, I. R., Moestrup, S. K., van den Berg, B. M., Pannekoek, H., Nielsen, M. S., and van Zonneveld, A. J. (1995) J Biol Chem 270(20), 11770-5.). During the biopanning phage were eluted using glycine-adjusted 50 mM hydrochloric acid, pH 2.1. Selection rounds were repeated another 3 times and the output/input ratio was calculated after titration of phage. These ratios indicate the phage enrichment values during the procedure. In FIG. 11 the output/input ratios per selection round are shown as well as the results of a phage ELISA. As can be seen in the figure, in both selections a strong enrichment for binding Fab phage has occurred, mounting to approximately 100-fold for the Hp-Hb complex-selection and to 1000-fold for the anti-CD163 selection. Upon testing randomly picked clones from the four consequetive rounds of selections, we found binding clones in the third round of selection for both antigens. The results of two ELISA assays are shown in FIG. 11, panels B and D. In total, a hundred clones were screened from the second and third round of selection. Postive clones were not further enriched in the fourth round of selection. To investigate if selected clones were different, PCR fingerprinting with different restriction enzymes were performed on all positive clones. The experiment showed that in both selections one type of Fab antibody (fingerprinting data not shown) was isolated. Fab1 was selected from the Hp-Hb complex-selections and Fab18 from the CD163 selection.

Screening of the selected anti-Hp-Hb complex and anti-CD163 repertoires—To identify Hp-Hb complex- and CD163 binding Fab antibody phage, an ELISA was performed in which Hp-Hb complexes or CD163 were coated and approximately 10$^{10}$ phage expressed by single colonies were incubated. Bound phage were subsequently detected using an anti-M13 phage conjugate. The procedure was performed as described (Horn, I. R., Moestrup, S. K., van den Berg, B. M., Pannekoek, H., Nielsen, M. S., and van Zonneveld, A. J. (1995) J Biol Chem 270(20), 11770-5.). The number of unique Fabs was determined by PCR fingerprinting with two different fine-cutting restriction enzymes (Marks, J. D., Hoogenboom, H. R., Bonnert, T. P., McCafferty, J., Griffiths, A. D., and Winter, G. (1991) J Mol Biol 222(3), 581-97.). The results of the binding of Fab1-phage to these antigens are shown in FIG. 2A. As can be concluded from the figure, Fab1-phage strongly reacts with the Hp-Hb complex, whereas low binding to Hb and Hp is measured. Binding of Fab2-phage could not be detected to any of the antigens, indicating that the phage itself does not aspecifically interacts with any of the antigens (not shown). The observed differences can neither be accounted for by different coating efficiencies, since in a control experiment polyclonal sera against the different antigens react with the uncomplexed and the complexed proteins to the same extent (data not shown).

Preparation of Soluble Fabs and SPR analysis—The pCOMB3X vector allows for expression of soluble Fab by changing bacterial strains because of the presence of an amber codon in between the heavy chain first constant domain and the sequence encoding the M13 gene III product (13. Andris-Widhopf, J., Rader, C., Steinberger, P., Fuller, R., and Barbas, C. F., 3rd. (2000) J Immunol Methods 242(1-2), 159-81.). We have used the non-suppressor *E. coli* strain HB2151, which was kindly supplied by dr. P. Kristensen (department of Molecular Biology, University of Aarhus). Anti-Hp-Hb complex antibody Fab1 was purified from the bacterial supernatant upon overnight expression in super broth medium containing 1 mM isopropyl-β-D-thio-galactopyranoside. The anti-CD163 antibody Fab18 was purified from the bacterial cells after sonication in phenyl-methyl-sulfonyl fluoride-containing Tris-buffered saline. Both antibodies were purified to homogeneity after filtration in a single step affinity chromatography method using an anti-mouse kappa light chain SEPHAROSE®-coupled antibody from Zymed Laboratories (AH Diagnostics, Denmark). Preparations were concentrated on AMICON® concentrators and amounts were determined using the bicinchoninic acid method from Pierce. Purity was checked by SDS-polyacrylamide gel electrophoresis (SDS-PAGE) in combination with silverstaining. Fab activity was determined in an ELISA using an anti-HA-biotin conjugate (Hoffman-La Roche).

SPR analyses were performed in a BIAcore™2000 instrument (BIAcore AB, Sweden) as described (1,16). CM5 sensorchips were immobilized with approximately 55-66 fmoles per mm$^2$ of CD163, Hp, Hb or Hp-Hb complex. As a running buffer we used 10 mM HEPES-buffer containing 150 mM and 0.5 mM CaCl$_2$ at pH 7.4. The data were plotted and subsequently fitted using the BIAevaluation 3.0 software. To further establish the binding characteristics of the isolated Fab phage. This procedure yielded approximately 0.5 mg pure Fab per liter of bacterial culture. The purity of Fabs has been determined by a silverstained polyacrylamide gel. Exact amounts of recombinant proteins were determined by applying the bicinchoninic acid method. After reassessing the binding activity of the pure Fab antibodies by ELISA, the binding of Fab1 to Hp-Hb complexes was further investigated with surface plasmon resonance. Using a sensorchip immobilized with both Hb, Hp and Hp-Hb complexes which allows for kinetic measurements, we derived a K$_D$ constant of 3.9 nM for binding of Fab1 to Hp-Hb complexes. No binding to the other antigens could be detected at all, thereby demonstrating the complex-specificity of Fab1. These results are in line with the (phage) ELISA data. The binding curves are depicted in FIG. 2B. Anti-CD163 Fab18 demonstrates a low affinity for CD163 which is in the micromolar range (not shown).

CD163-$^{125}$I-Hp-Hb complex-binding assays—Assays for measuring $^{125}$Iodine-labeled Hp-Hb complex-binding to CD163 in the presence or absence of competing antibodies were performed essentially as described ((Kristiansen, M., Graversen, J. H., Jacobsen, C., Sonne, O., Hoffman, H. J., Law, S. K., and Moestrup, S. K. (2001) *Nature* 409(6817), 198-201.) (Birn, H., Verroust, P. J., Nexo, E., Hager, H., Jacobsen, C., Christensen, E. I., and Moestrup, S. K. (1997) *J Biol Chem* 272(42), 26497-504.)) Optimal coating conditions were first determined by using serial receptor dilutions followed by incubation with Hp-Hb complexes [(1:1) and (2:2) types)], labeled with $^{125}$Iodine using the chloramine-T method. Binding assays were done using approximately 3000 counts per minute/well. Radioactivity was counted using a Packard gamma counter.

Cellular uptake and degradation experiments using $^{125}$Iodine-labeled Hp-Hb complexes—Internalization and subsequent degradation in COS1 cells were described previously (Kozyraki, R., Fyfe, J., Kristiansen, M., Gerdes, C., Jacobsen, C., Cui, S., Christensen, E. I., Aminoff, M., de la Chapelle, A., Krahe, R., Verroust, P. J., and Moestrup, S. K. (1999) Nat Med 5(6), 656-61.). In brief, confluent cells were treated with 3000 counts per minute of $^{125}$I-labeled Hp-Hb complexes and incubated concommitantly with a range of Fab antibody concentrations up to micromolar amounts. Supernatant was counted each 30 minutes to assess the degradation rate and after 4 hours cells were stringently washed followed by counting of internalized radioactivity. As can be seen in FIG. 13, already at nanomolar concentrations a 50% inhibition of binding is measured. The anti-CD163 Fab18 antibody also inhibits the binding, albeit at micromolar concentrations. In the presence of micromolar amounts of an irrelevant Fab antibody (FabA8, (Horn, I. R., Moestrup, S. K., van den Berg, B. M., Pannekoek, H., Nielsen, M. S., and van Zonneveld, A. J. (1995) J Biol Chem 270(20), 11770-5.)) at least 80% tracer is still bound. The data were obtained using the (2:2) Hp form, however, in a set of experiments using the (1:1) form similar results were obtained, consistent with the competition data described previously (1. Kristiansen, M., Graversen, J. H., Jacobsen, C., Sonne, O., Hoffman, H. J., Law, S. K., and Moestrup, S. K. (2001) Nature 409(6817), 198-201.). Using ELISA and SPR methods, we were also able to demonstrate the inhibition of Hp-Hb complex binding to CD163 by Fab1 (data not shown).

The invention claimed is:

1. An antibody operably linked to a substance, wherein the antibody is capable of binding CD163 and wherein the substance is a prophylactic or therapeutic medicament, wherein the antibody is capable of activating uptake into a CD163-presenting cell, and wherein the antibody is capable of binding to a region in one or more of the SRCR domains D1-D9 of CD163.

2. An antibody according to claim 1 wherein the antibody is a Fab antibody.

3. An antibody according to claim 1 wherein binding of the antibody to CD163 elicits uptake of the antibody-linked substance into a CD163-presenting cell.

4. An antibody according to claim 1, wherein said antibody is capable of binding to a region in one or more of the SRCR domains D1-D9 of CD163, wherein said domains corresponds to the following amino acids in a translated cDNA sequence with Genbank accession no Z22968 (SEQ ID NO:26 and 27): D1: aa 46-146, D2: aa 154-253, D3: aa 261-360, D4: aa 368-467, D5: aa 473-572, D6: aa 578-677, D7: aa 714-814, D8: aa 819-920 and D9: aa 924-1023.

5. The antibody of claim 1 wherein the substance is a therapeutic medicament.

6. The antibody of claim 1 wherein the substance is an anti-inflammatory medicament.

7. An antibody according to claim 1, wherein the prophylactic or therapeutic medicament is selected from the group consisting of an antimicrobial agent, an anti-cancer drug, an anti-HIV drug, a medicament against lymphomas and an antigen.

8. An antibody according to claim 1, wherein the prophylactic or therapeutic medicament is an antibody.

9. An antibody according to claim 1, wherein the prophylactic or therapeutic medicament binds a target desired to be cleared from plasma.

10. An antibody according to claim 9, wherein the target desired to be cleared from plasma is myoglobin.

11. The antibody according to claim 4 wherein the antibody is capable of binding to a region in SRCR domains I-IV of CD163.

12. The antibody of claim 1, which is capable of binding to SRCR domain D3 or D4 of CD163.

13. The antibody of claim 1 wherein the antibody is a monoclonal antibody.

14. The antibody of claim 1 which is capable of inhibiting the binding of the Hp-Hb complex to CD163.

* * * * *